US010092527B2

(12) United States Patent
Turano et al.

(10) Patent No.: US 10,092,527 B2
(45) Date of Patent: Oct. 9, 2018

(54) METHODS FOR THE BIOSYNTHESIS OF TAURINE OR HYPOTAURINE IN CELLS

(71) Applicant: PLANT SENSORY SYSTEMS LLC, Baltimore, MD (US)

(72) Inventors: Frank J. Turano, Baltimore, MD (US); Kathleen A. Turano, Baltimore, MD (US); Peter S. Carlson, Baltimore, MD (US); Alan M. Kinnersley, Baltimore, MD (US)

(73) Assignee: PLANT SENSORY SYSTEMS, LLC, Baltimore, MD (US)

( * ) Notice: Subject to any disclaimer, the term of this patent is extended or adjusted under 35 U.S.C. 154(b) by 85 days.

(21) Appl. No.: 14/993,519

(22) Filed: Jan. 12, 2016

(65) Prior Publication Data

US 2016/0158168 A1 Jun. 9, 2016

Related U.S. Application Data

(63) Continuation of application No. 13/505,415, filed as application No. PCT/US2010/054664 on Oct. 29, 2010, now Pat. No. 9,267,148.

(60) Provisional application No. 61/263,548, filed on Nov. 23, 2009, provisional application No. 61/257,240, filed on Nov. 2, 2009.

(51) Int. Cl.

| | |
|---|---|
| ***A61K 31/145*** | (2006.01) |
| ***A61K 31/185*** | (2006.01) |
| ***C12N 15/82*** | (2006.01) |
| ***C12N 9/02*** | (2006.01) |
| ***C12P 13/00*** | (2006.01) |
| ***A23L 33/10*** | (2016.01) |
| ***A23K 10/12*** | (2016.01) |
| ***A23K 20/10*** | (2016.01) |

(52) U.S. Cl.

CPC ............ *A61K 31/145* (2013.01); *A23K 10/12* (2016.05); *A23K 20/10* (2016.05); *A23L 33/10* (2016.08); *A61K 31/185* (2013.01); *C12N 9/0069* (2013.01); *C12N 15/8243* (2013.01); *C12N 15/8253* (2013.01); *C12N 15/8261* (2013.01); *C12N 15/8271* (2013.01); *C12N 15/8273* (2013.01); *C12N 15/8279* (2013.01); *C12P 13/001* (2013.01); *A23V 2002/00* (2013.01); *C12Y 113/1102* (2013.01); *Y02A 40/146* (2018.01)

(58) Field of Classification Search

CPC .......................... A61K 31/145; C12N 15/8243

See application file for complete search history.

(56) References Cited

U.S. PATENT DOCUMENTS 6,998,422 B2 * 2/2006 Ohsawa ................. A61K 31/16 514/548
2009/0183270 A1 7/2009 Adams et al.

FOREIGN PATENT DOCUMENTS

| | | | |
|---|---|---|---|
| WO | 02/38736 | A2 | 5/2002 |
| WO | 2007044043 | A2 | 4/2007 |
| WO | 2009009142 | A2 | 1/2009 |

OTHER PUBLICATIONS

Honjoh, K. et al. Amino Acids (published online Jul. 26, 2009) vol. 38, pp. 1173-1183.*
Gaylord, T.G. et al. Aquaculture (2007) vol. 269, pp. 514-524.*
Agnello, G et al. ACS Chem. Biol., Oct. 2013; vol. 8, No. 10, pp. 1-17.*
Tevatia, R. et al., Algal Research 2015, vol. 9, pp. 21-26.*
Agnello, G. et al., ACS Chem Biol. Oct. 18, 2013; vol. 8, No. 10 pp. 1-17.*
Honjoh, K. et al., "Enhancement of Menadione Stress Tolerance in Yeast by Accumulation of Hypotaurine and Taurine: Co-expression of cDNA Clones, from Cyprinus Carpio, for Cysteine Dioxygenase and Cysteine Sulfinate Decarboxlase in *Saccharomyces Cerevisiae*," Amino Acids, 2010, vol. 38, pp. 1173-1183, © Springer-Verlag 2009.
Stipanuk, M.H. et al., "Mammalian Cysteine Metabolism: New Insights into Regulation of Cysteine Metabolism," Journal of Nutrition, vol. 136, No. 6, Suppl. S, Jun. 2006, pp. 1652S-1659S, XP-002626793, © 2006 American Society for Nutrition.
De La Rosa, J. et al., "Evidence for a Rate-Limiting Role of Cysteinesulfinate Decarboxylase Activity in Taurine Biosynthesis In Vivo," Comparative Biochemistry and Physiology, B. Comparative Biochemistry, vol. 81, No. 3, pp. 565-571, © 1985 Pergamon Press Ltd.
Flinn, J.E. et al., "Green Plants as Biofactories for Drugs," Biopharm International, Advanstar Communications, Duluth, MN, US, vol. 17, No. 8, Aug. 1, 2004, pp. 42-49, XP009109706.
Beyer, P., "Golden Rice: Introducing the β-Carotene Biosynthesis Pathway into Rice Endosperm by Genetic Engineering to Defeat Vitamin A Deficiency," Journal of Nutrition, vol. 132, No. 3, Mar. 1, 2002, pp. 506S-510S, XP001069128, © 2002 American Society for Nutritional Services.

(Continued)

*Primary Examiner* — Russell Kallis

(74) *Attorney, Agent, or Firm* — Rothwell, Figg, Ernst & Manbeck, P.C.

(57) ABSTRACT

The present invention describes an approach to increase taurine or hypotaurine production in prokaryotes. More particularly, the invention relates to genetic transformation of organisms with genes that encode proteins that catalyze the conversion of cysteine to taurine, methionine to taurine, cysteamine to taurine, or alanine to taurine. The invention describes methods for the use of polynucleotides that encode cysteine dioxygenase (CDO) and sulfinoalanine decarboxylase (SAD) polypeptides in prokaryotes to increase taurine, hypotaurine or taurine precursor production. The preferred embodiment of the invention is in plants but other organisms may be used. Increased taurine production in prokaryotes could be used as nutraceutical, pharmaceutical, or therapeutic compounds or as a supplement in animal feed.

11 Claims, 1 Drawing Sheet

Specification includes a Sequence Listing.

(56) References Cited

OTHER PUBLICATIONS

Lahdesmaki, P., "Determination of Taurine and Other Acidic Amino-Acids in Plants," Phytochemistry (Oxford), vol. 25, No. 10, 1986, pp. 2409-2411, XP002626795, Pergamon Journals Ltd.
Stintzing, F.C., "Amino Acid Composition and Betaxanthin Formation in Fruits From Opuntia ficus-Indica," Planta Medica, vol. 65, No. 7, Oct. 1999, pp. 632-635, XP002626796, © Georg Thieme Verlag Stutgart-New York.
Haas, F. et al., Plant Physiology (Oct. 2008) vol. 148, pp. 1055-1067.
Feugang, J.M. et al., Frontiers in Bioscience (Sep. 1, 2006), vol. 11, pp. 2574-2589.

* cited by examiner

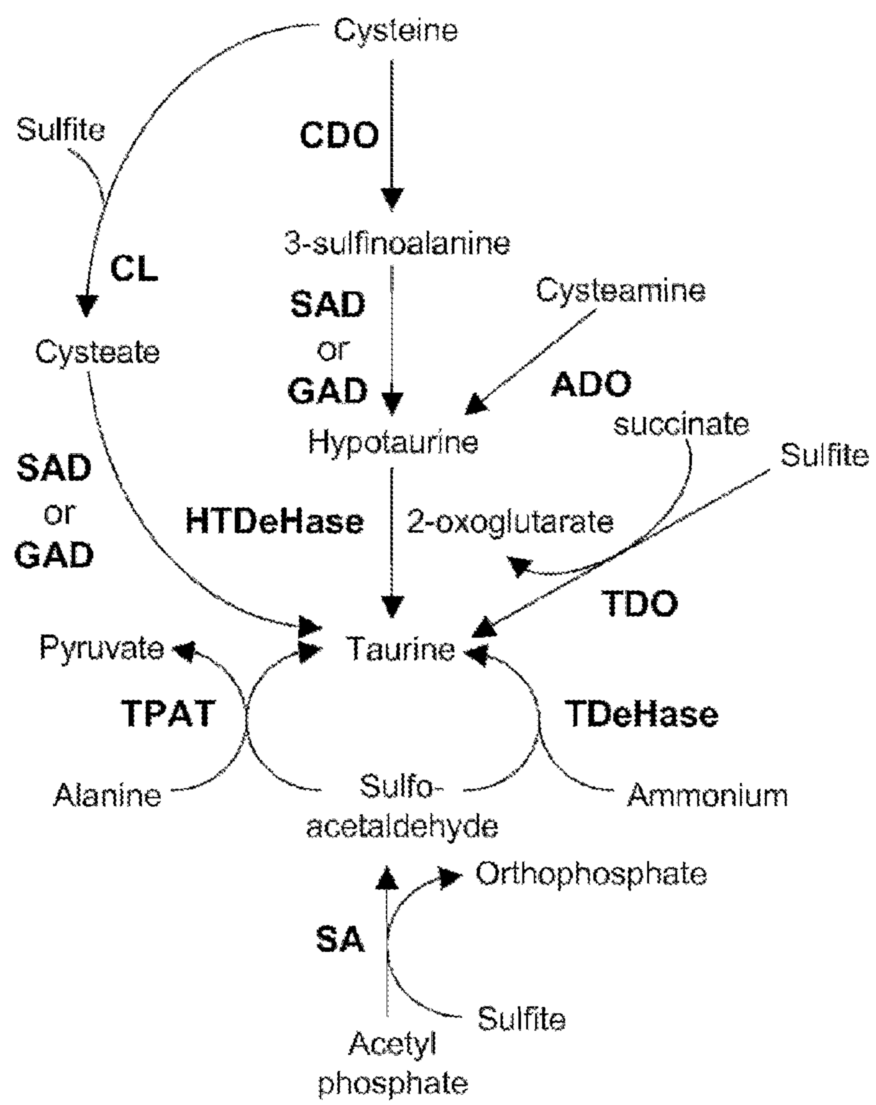
Cysteine
Sulfite
CDO
CL
3-sulfinoalanine
SAD
or
GAD
Cysteamine
Cysteate
ADO
Hypotaurine
succinate
Sulfite
SAD
or
GAD
HTDeHase
2-oxoglutarate
TDO
Pyruvate
Taurine
TPAT
TDeHase
Alanine
Sulfo-
acetaldehyde
Ammonium
Orthophosphate
SA
Sulfite
Acetyl
phosphate

METHODS FOR THE BIOSYNTHESIS OF TAURINE OR HYPOTAURINE IN CELLS

CROSS-REFERENCE TO RELATED APPLICATIONS

This application is continuation of U.S. patent application Ser. No. 13/505,415 filed 1 May 2012, which in turn is a national stage filing under 35 U.S.C. § 371 of PCT/US2010/054664 filed 29 Oct. 2010 which in turn is related to and claims the benefit of and U.S. Patent Application Ser. No. 61/263,548 filed 23 Nov. 2009 and U.S. Patent Application Ser. No. 61/257,240 filed 2 Nov. 2009. Each application is incorporated herein in its entirety by reference.

SEQUENCE LISTING

The present application includes a Sequence Listing in electronic format filed on 9 Feb. 2016. The Sequence Listing is entitled 3834116SequenceListing.txt, created on 3 Dec. 2015 and is 69 kb in size. The information in the electronic format of the Sequence Listing is incorporated herein by reference in its entirety.

FIELD OF THE INVENTION

The present invention is in the field of recombinant production of taurine.

BACKGROUND OF THE INVENTION

Taurine as a plant growth stimulator

Exogenous application of taurine has been reported to increase crop harvest, yield, and biomass (1). Applications of taurine by foliar spray, soil and roots application, and seed immersion increase crop production and seedling growth (1). Exogenous applications of taurine have also been shown to increase photosynthetic capacity of isolated plant cells (protoplasts and chloroplasts) (1). Increased taurine production in plants can enhance plant growth and development, yield, or tolerance to biotic and/or abiotic stresses. Increased yield, growth, or biomass may be a result of increased nitrogen flow, sensing, uptake, storage, transport or nitrogen use efficiency. Increased yield, growth or biomass may also be a result of increased carbon metabolism due to increased photosynthesis or increased carbohydrate metabolism by increased sucrose production and/or transport or increase biosynthesis or mobilization of starch, or oil. Increased yield, growth or biomass may also be associated with increased phosphorus uptake, transport or utilization. Increased yield, growth or biomass may also be associated with increased sulfur or sulfate uptake, transport or utilization. Increased yield, growth or biomass may also be associated with increased water uptake, transport, utilization or water-use-efficiency. Increased yield, growth or biomass may also be due to changes in the cell cycle modifications that improve growth rates and may increase early vigor and accelerate maturation leading to improved yield. Increased yield, growth or biomass may also be due to changes in the production of hormones or signaling molecules that regulate and improve plant growth and development leading to improvements in yield and biotic or abiotic stress tolerance. Increases in carbon, nitrogen, phosphorus, or sulfate flow, sensing, uptake, storage, transport or efficiency may improve seed quality for starch, oil or protein content. Increased yield, growth or biomass may also be a result of increased tolerance to abiotic stress such as changes in osmotic conditions, oxidative damage, drought, salt, cold, freezing, heat, UV light or light intensity. Increased yield, growth or biomass may also be a result of increased tolerance to biotic stress such as challenges, infection or insult from pests, pathogens, bacteria, microbes, viruses, viroids, microorganisms, invertebrates, insects, nematodes, or vertebrate. Increased yield, growth or biomass may be a result of increased tolerance to abiotic stresses such as changes in osmotic conditions or light intensity, oxidative damage, drought, salt, cold, freezing, heat, or UV radiation.

Taurine is an Essential Compound for Animals

Taurine is essential for human neonatal development (2) and plays an important role in brain development (3, 4). Taurine is involved in the modulation of intracellular calcium homeostasis (5, 6) and may balance glutamate activity, protecting neurons against glutamate excitotoxicity (7, 8). Taurine is also an osmoregulator (9). Taurine is essential for heart function (10), protects the integrity of hepatic tissue (11), and plays a role in photoprotection (12).

Taurine as a Pharmaceutical or Therapeutic

Taurine is used as a pharmaceutical and therapeutic. Taurine has been used in the treatment of cardiovascular diseases (13, 14), elevated blood pressure (15), seizure disorders (16), hepatic disorders (17), and alcoholism (18) and may be useful in the treatment of diabetes (19), Alzheimer's disease (20), and ocular disorders (21). Taurine has been shown to prevent obesity (22) and control cholesterol (23, 24). Taurine acts as an antioxidant and protects against toxicity of various substances (25-27). Taurine has been shown to prevent oxidative stress induced by exercise (28), and is used in energy drinks to improve performance (29). Taurine can also be used in topical applications to treat dermatological conditions (30).

Taurine as a Dietary Supplement

Taurine is biosynthesized in most animals and can be found in meat and seafood. Those who do not eat these foods regularly (e.g., vegetarians) or do not produce sufficient levels of taurine, e.g., cats (31), must acquire it through dietary supplement. Trout that are fed all-plant protein diets must acquire dietary taurine for normal growth (32).

Metabolic Pathways that Synthesize Taurine

With few exceptions (33, 34), taurine is found in plants only in low levels (35), and the metabolic pathway for taurine and hypotaurine has not yet been identified in plants. Several metabolic pathways that synthesize taurine and hypotaurine have been identified in animals and bacteria (FIG. 1). In animals, cysteine and oxygen are converted into 3-sulfinoalanine by cysteine dioxygenase (CDO). 3-sulfinoalanine is converted into hypotaurine by sulfinoalanine decarboxylase (SAD) or glutamate decarboxylase (GAD). Hypotaurine is converted into taurine either by the activity of hypotaurine dehydrogenase (HTDeHase) or by a spontaneous conversion. Cysteamine (2-aminoethanethiol) and oxygen are converted into hypotaurine by cysteamine dioxygenase (ADO), and hypotaurine is converted into taurine. Alternatively cysteine and sulfite are converted into cysteate and hydrogen sulfide by cysteine lyase (cysteine sulfite lyase or cysteine hydrogen-sulfide-lyase). Cysteate is converted into taurine by SAD or GAD. In bacteria, the compound 2-sulfoacetaldehyde is synthesized from acetyl phosphate and sulfite by sulfoacetaldehyde acetyltransferase (SA). Alanine and 2-sulfoacetaldehyde are converted into taurine and pyruvate by taurine-pyruvate aminotransferase (TPAT). In addition, sulfoacetaldehyde and ammonia (or ammonium) are converted into taurine and water in the presence of ferrocytochrome C by taurine dehydrogenase. Sulfite, aminoacetaldehyde, carbon dioxide and succinate are converted into taurine, 2-oxoglutarate and oxygen by taurine dioxygenase (TDO).

SUMMARY OF THE INVENTION

The invention provides methods and compositions for taurine or taurine precursor production in organisms. More particularly, the invention encompasses the use of polynucleotides that encode in plants functional (1) cysteine dioxygenase (CDO), (2) CDO and sulfinoalanine decarboxylase (SAD) or glutamate decarboxylase (GAD), (3) cysteamine dioxygenase (ADO), (4) taurine-pyruvate aminotransferase (TPAT), (5) TPAT and sulfoacetaldehyde acetyltransferase (SA), (6) taurine dehydrogenase (TDeHase) or (7) taurine dioxygenase (TDO). The invention provides methods for transforming plants and constructing vector constructs and other nucleic acid molecules for use therein. The transgenic plants will have increased levels of taurine or taurine-precursors for enhanced plant growth and development, yield, or tolerance to biotic and/or abiotic stresses and can be used to provide nutraceuticals or pharmaceuticals for improving physical or mental performance, antioxidative activity, or therapeutic compounds in the treatment of conditions including congestive heart failure, high blood pressure, hepatitis, high cholesterol, diabetes, fibrosis, epilepsy, autism, attention deficit-hyperactivity disorder, retinal disorders, alcoholism, or as a food supplement in animal feed.

The invention provides isolated cells comprising exogenous DNA which expresses enzymes of taurine biosynthetic pathways. In one embodiment, an isolated cell comprises two separate expression cassettes. A first expression cassette comprises a first promoter operably linked to a first polynucleotide, and a second expression cassette comprises a second promoter operably linked to a second polynucleotide. In some embodiments, the first polynucleotide encodes cysteine dioxygenase (CDO) and the second polynucleotide encodes sulfinoalanine decarboxylase (SAD). In other embodiments the first polynucleotide encodes cysteine dioxygenase (CDO) and the second polynucleotide encodes glutamate decarboxylase (GAD). In still other embodiments, the first polynucleotide encodes taurine-pyruvate aminotransferase (TPAT) and the second polynucleotide encodes sulfoacetaldehyde acetyltransferase (SA). In yet other embodiments the first polynucleotide encodes a small subunit of taurine dehydrogenase (ssTDeHase) and the second polynucleotide encodes a large subunit of taurine dehydrogenase (lsTDeHase).

Some isolated cells of the invention comprise exogenous DNA which comprises a single expression cassette. The single expression cassette comprises a promoter operably linked to a polynucleotide which encodes (i) CDO and SAD; (ii) CDO and GAD; (iii) TPAT; (iv) TPAT and SA; or (v) ssTDeHase and lsTDeHase.

Other isolated cells of the invention are plant cells which comprise exogenous DNA which comprises a promoter operably linked to a polynucleotide. The polynucleotide encodes CDO, ADO, or taurine dioxygenase (TDO).

The invention also provides plant storage organs comprising isolated cells of the invention; transgenic seeds with a genome comprising exogenous DNA encoding one or more of CDO, SAD, GAD, ADO, TPAT, SA, TDO, or TDeHase, and transgenic plants grown from the transgenic seeds.

The invention provides methods of altering a property of a transgenic plant of the invention by contacting the transgenic plant with an agent which increases sulfur or nitrogen concentration in cells of the transgenic plant.

The invention also provides pharmaceutical compositions and nutritional supplements comprising an extract of a transgenic plant of the invention, and feeds comprising a component, which can be one or more of the plant storage organs, transgenic seeds, and transgenic plants of the invention.

In one embodiment of the invention polynucleotides encoding functional CDO and SAD or GAD enzymes are used to transform plant cells or to transform plants. Inventive methods produce plants that have advantages of enhanced taurine production, that result in plants with enhanced plant growth characteristics, survival characteristics and/or tolerance to environmental or other plant stresses and increase nutritional, pharmaceutical, or therapeutic value. Plants are genetically modified in accordance with the invention to introduce into the plant a polynucleotide that encodes a CDO enzyme and/or a polynucleotide that encodes a SAD or GAD that functions in the formation of hypotaurine or taurine in the plant.

Another embodiment of the invention describes the use of ADO, TPAT, TDeHase, or TDO to produce hypotaurine or taurine in plants.

Another embodiment of the invention describes the use of TPAT and SA to produce taurine in plants.

Another embodiment of the invention describes the use of polynucleotides that encode polypeptides for functional CDO, CDO and SAD or GAD, ADO, TPAT, SA, TDeHase or TDO expressed in eukaryotes or prokaryotes or in eukaryotic or prokaryotic cells, for hypotaurine or taurine production.

BRIEF DESCRIPTION OF THE FIGURE

FIG. 1 shows taurine biosynthetic pathways.

DETAILED DESCRIPTION OF THE INVENTION

The present invention provides methods and materials for the production of taurine (2-aminoethanesulfonic acid) in cells and living organisms. In preferred embodiments, the invention provides methods for the genetic transformation of organisms, preferably plants, with genes that encode proteins that catalyze the conversion of cysteine to taurine, methionine to taurine, cysteamine to taurine, or alanine to taurine. The invention also provides methods of using plants with increased levels of endogenous taurine or taurine derivatives such as hypotaurine to improve plant growth, development and performance, that is to increase plant size, biomass, yield or tolerance to biotic or abiotic stress. The invention also provides methods of using plants with elevated levels of endogenous taurine or taurine derivatives such as hypotaurine as a food- or feed-supplement, dietary supplement, or as a component of a health supplement or therapy.

The present invention describes the methods for the synthesis of DNA constructs for taurine or taurine precursor production from polynucleotides and vectors and the methods for making transformed organisms including plants, photosynthetic organisms, microbes, invertebrates, and vertebrates. The present invention is unique in that it describes a method to produce plants that have advantages of enhanced taurine production and that result in plants with enhanced plant growth characteristics, survival characteristics and/or tolerance to environmental or other plant stresses and increased nutritional, pharmaceutical, or therapeutic value.

The present invention describes the insertion of the taurine biosynthetic pathway in organisms where the pathway does not exist or has not clearly been identified. The invention describes methods for the use of polynucleotides that encode functional cysteine dioxygenase (CDO) and sulfinoalanine decarboxylase (SAD) or glutamate decarboxylase (GAD), cysteamine dioxygenase (ADO), taurine-pyruvate aminotransferase (TPAT), TPAT and sulfoacetaldehyde acetyltransferase (SA), taurine dehydrogenase (TDeHase) or taurine dioxygenase (TDO) in plants. The preferred embodiment of the invention is in plants but other organisms may be used.

Enzymes of Taurine Biosynthetic Pathways

Examples of amino acid sequences of enzymes of taurine biosynthetic pathways are provided in the sequence listing: SEQ ID NO:3 and SEQ ID NO:4 (CDO); SEQ ID NO:7 and SEQ ID NO:8 (SAD); SEQ ID NO:11 and SEQ ID NO:12 (GAD); SEQ ID NO:18 (TPAT); SEQ ID NO:20 (SA); SEQ ID NO:22 (ssTDeHase); SEQ ID NO:22 (lsTDeHase); SEQ ID NO:13 and SEQ ID NO:14 (ADO); and SEQ ID NO:26 (TDO). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for CDO, SAD, GAD, or ADO from zebra fish (Danio rerio) or TPAT, SA, ssTDeHase or lsTDeHase from *Roseobacter denitrificans* or TDO from Escherichia coli may differ to a certain degree from the amino acid sequences of CDO, SAD, GAD, ADO, TPAT, SA, ssTDeHase, lsTDeHase or TDO in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, CDO, SAD, GAD, ADO, TPAT, SA, ssTDeHase, lsTDeHase or TDO activity is generally at least 40%, 50%, 60%, 70%, 80% or 90%, preferably 60-90% of the native protein for the native substrate. Tables of conserved substitution provide lists of functionally similar amino acids.

The following three groups each contain amino acids that are conserved substitutions for one another: (1) Alanine (A), Serine (S), Threonine (T); (2) Aspartic acid (D), Glutamic acid (E); and (3) Asparagine (N), Glutamine (Q);

Suitable polynucleotides for CDO, SAD, GAD, ADO, TPAT, SA, TDO, ssTDeHase, and lsTDeHase As examples, suitable polynucleotides encoding enzymes of taurine biosynthetic pathways are described below. The invention is not limited to use of these sequences, however. In fact, any nucleotide sequence which encodes an enzyme of a taurine biosynthetic pathway can be used in an expression vector to produce that enzyme recombinantly.

Suitable polynucleotides for CDO are provided in SEQ ID NO:1 and SEQ ID NO:2 Other suitable polynucleotides for use in accordance with the invention may be obtained by the identification of polynucleotides that selectively hybridize to the polynucleotides of SEQ ID NO:1 or SEQ ID NO:2 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1 or SEQ ID NO:2 when it used as a reference for sequence comparison or polynucleotides that encode polypeptides that have substantial identity to amino acid sequence of SEQ ID NO:3 or SEQ ID NO:4 when it used as a reference for sequence comparison.

Suitable polynucleotides for SAD are provided in SEQ ID NO:5 and SEQ ID NO:6. Other suitable polynucleotides for use in accordance with the invention may be obtained by the identification of polynucleotides that selectively hybridize to the polynucleotides of SEQ ID NO:5 or SEQ ID NO:6 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:5 or SEQ ID NO:6 when it used as a reference for sequence comparison or polynucleotides that encode polypeptides that have substantial identity to amino acid sequence of SEQ ID NO:7 or SEQ ID NO:8 when it is used as a reference for sequence comparison.

Suitable polynucleotides for GAD are provided in SEQ ID NO:9 and SEQ ID NO:10. Other suitable polynucleotides for use in accordance with the invention may be obtained by the identification of polynucleotides that selectively hybridize to the polynucleotides of SEQ ID NO:9 or SEQ ID NO:10 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:9 or SEQ ID NO:10 when it used as a reference for sequence comparison or polynucleotides that encode polypeptides that have substantial identity to amino acid sequence of SEQ ID NO:11 or SEQ ID NO:12 when it used as a reference for sequence comparison.

Suitable polynucleotides for ADO are provided in SEQ ID NO:13 and SEQ ID NO:14. Other suitable polynucleotides for use in accordance with the invention may be obtained by the identification of polynucleotides that selectively hybridize to the polynucleotides of SEQ ID NO:13 or SEQ ID NO:14 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:13 or SEQ ID NO:14 when it used as a reference for sequence comparison or polynucleotides that encode polypeptides that have substantial identity to amino acid sequence of SEQ ID NO:15 or SEQ ID NO:16 when it used as a reference for sequence comparison.

A suitable polynucleotide for TPAT is provided in SEQ ID NO:17. Other suitable polynucleotides for use in accordance with the invention may be obtained by the identification of polynucleotides that selectively hybridize to the polynucleotides of SEQ ID NO:17 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:17 when it used as a reference for sequence comparison or polynucleotides that encode polypeptides that have substantial identity to amino acid sequence of SEQ ID NO:18 when it used as a reference for sequence comparison.

A suitable polynucleotide for SA is provided in SEQ ID NO:19. Other suitable polynucleotides for use in accordance with the invention may be obtained by the identification of polynucleotides that selectively hybridize to the polynucleotides of SEQ ID NO:19 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:19 when it used as a reference for sequence comparison or polynucleotides that encode polypeptides that have substantial identity to amino acid sequence of SEQ ID NO:20 when it used as a reference for sequence comparison.

A suitable polynucleotide for ssTDeHase is provided in SEQ ID NO:21. Other suitable polynucleotides for use in accordance with the invention may be obtained by the identification of polynucleotides that selectively hybridize to the polynucleotides of SEQ ID NO:21 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:21 when it used as a reference for sequence comparison or polynucleotides that encode polypeptides that have substantial identity to amino acid sequence of SEQ ID NO:22 when it used as a reference for sequence comparison.

A suitable polynucleotide for lsTDeHase is provided in SEQ ID NO:23. Other suitable polynucleotides for use in accordance with the invention may be obtained by the identification of polynucleotides that selectively hybridize to the polynucleotides of SEQ ID NO:23 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:23 when it used as a reference for sequence comparison or polynucleotides that encode polypeptides that have substantial identity to amino acid sequence of SEQ ID NO:24 when it used as a reference for sequence comparison.

A suitable polynucleotide for TDO is provided in SEQ ID NO:25. Other suitable polynucleotides for use in accordance with the invention may be obtained by the identification of polynucleotides that selectively hybridize to the polynucleotides of SEQ ID NO:25 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:25 when it used as a reference for sequence comparison or polynucleotides that encode polypeptides that have substantial identity to amino acid sequence of SEQ ID NO:26 when it used as a reference for sequence comparison.

Another embodiment of the invention is a polynucleotide (e.g., a DNA construct) that encodes a protein that functions as a CDO, SAD, GAD, ADO, TPAT, SA, ssTDeHase, lsTDeHase or TDO and selectively hybridizes to either SEQ ID NO:1, SEQ ID NO:2, SEQ ID NO:5, SEQ ID NO:6, SEQ ID NO:9, SEQ ID NO:10, SEQ ID NO:13, SEQ ID NO:14, SEQ ID NO:17, SEQ ID NO:19, SEQ ID NO:21, SEQ ID NO:23, or SEQ ID NO:25 respectively. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:3, SEQ ID NO:4, SEQ ID NO:7, SEQ ID NO:8, SEQ ID NO:11, SEQ ID NO:12, SEQ ID NO:15, SEQ ID NO:16, SEQ ID NO:18, SEQ ID NO:20, SEQ ID NO:22, SEQ ID NO:24, or SEQ ID NO:26. Substantial identity of amino acid sequences for these purposes normally means sequence identity of between 50-100%, preferably at least 55%, preferably at least 60%, more preferably at least 70%, 80%, 90%, and most preferably at least 95%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus each silent variation of a nucleic acid, which encodes a polypeptide of the present invention, is implicit in each described polypeptide sequence and incorporated in the descriptions of the invention.

It is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in both monocotyledonous and dicotyledonous plant species, sequences can be modified to account for the specific codon preferences and GC-content preferences of monocotyledonous plants or dicotyledonous plants, as these preferences have been shown to differ (36). An alternative approach to the generation of variants of the sequences is to use random recombination techniques such as "DNA shuffling" (37). An alternative method to modify the sequences is by rapid molecular evolution methods such as a staggered extension process (38).

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, tissue culture, molecular biology, chemistry, biochemistry and recombinant DNA technology, which are within the skill of the art (39-46).

A suitable polynucleotide for use in accordance with the invention may be obtained by cloning techniques using cDNA or genomic libraries, DNA, or cDNA from bacteria which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed or amplified using chemical synthesis. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using fusion-PCR (47), overlap-PCR (48) or chemical (de novo) synthesis (49-53) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are ligated together by recombination.

The recombinant expression cassette or DNA construct includes a promoter that directs transcription in a plant cell, operably linked to the polynucleotide encoding a CDO, SAD, GAD, ADO, TPAT, SA, ssTDeHase or lsTDeHase. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Promoters

A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter is induced by one or more, but not limiting to one of the following, abiotic stresses such as wounding, cold, dessication, ultraviolet-B (54), heat shock (55) or other heat stress, drought stress or water stress. The promoter may further be one induced by biotic stresses including pathogen stress, such as stress induced by a virus (56) or fungi (57, 58), stresses induced as part of the plant defense pathway (59) or by other environmental signals, such as light (60), carbon dioxide (61, 62), hormones or other signaling molecules such as auxin, hydrogen peroxide and salicylic acid (63, 64), sugars and gibberellin (65) or abscissic acid and ethylene (66).

In other embodiments of the invention, tissue-specific promoters are used. Tissue-specific expression patterns as controlled by tissue- or stage-specific promoters that include, but is not limited to, fiber-specific, green tissue-specific, root-specific, stem-specific, and flower-specific. Examples of the utilization of tissue-specific expression includes, but is not limited to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Although many promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize from the phosphenol carboxylase gene (67). There are suitable promoters for root specific expression (68, 69). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or 19S, a figwort mosaic virus promoter (FMV 35S), or the coat protein promoter of tobacco mosaic virus (TMV). The promoter may further be, for example, a promoter for the small subunit of ribulose-1,3-biphosphate carboxylase. Promoters of bacterial origin (microbe promoters) include the octopine synthase promoter, the nopaline synthase promoter and other promoters derived from native Ti plasmids (70).

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term “signal” is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

In another embodiment of the invention, a DNA construct comprising a plant GAD promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate decarboxylase. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). For example, the full-length promoter for the nodule-enhanced PEP carboxylase from alfalfa is 1277 basepairs prior to the start codon (71), the full-length promoter for cytokinin oxidase from orchid is 2189 basepairs prior to the start codon (72), the full-length promoter for ACC oxidase from peach is 2919 basepairs prior to the start codon (73), full-length promoter for cytokinin oxidase from orchid is 2189 basepairs prior to the start codon, full-length promoter for glutathione peroxidase1 from *Citrus sinensis* is 1600 basepairs prior to the start codon (74), and the full-length promoter for glucuronosyltransferase from cotton is 1647 basepairs prior to the start codon (75). Most full-length promoters are 1700 basepairs prior to the start codon. The accepted convention is to describe this region (promoter) as −1700 to −1, where the numbers designate the number of basepairs prior to the "A" in the start codon. In this embodiment of the invention that the region of −2000 to −1 basepairs 5' to a plant GAD is operably linked to a polynucleotide for the said encoded peptide to make a transformed plant that selectively expresses the polynucleotide or increases the level of the said protein where the plant GAD is expressed or accumulates. A plant GAD promoter is the −2000 to −1 basepair region genes that include, but is not limited to, the five *Arabidopsis thaliana* GADs (AtGAD) (76), petunia GAD (77), tomato GAD (78), tobacco GAD (79), rice (80), barely, poplar, soybean, mustard, orange, *Medicago truncatula,* grape and pine. Those of ordinary skill in the art can either digest the desired region using restriction enzymes and ligase to clone the plant GAD promoters or use amplification, such as PCR, techniques with the incorporation of restriction or recombination sites to clone the plant GAD promoters 5' to the desired polynucleotide. A plant GAD promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

In another embodiment of the invention, a DNA construct comprising a plant glutamate receptor promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant glutamate receptor. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). A plant glutamate receptor promoter is the −2000 to −1 basepair region genes that include, but is not limited to, the 20 *Arabidopsis thaliana* glutamate receptors (AtGLRs or AtGluRs) and 23 rice glutamate receptors. The promoters for the following AtGLRs genes, 1.1, 2.1, 3.1 (81), 3.2 (note this is designated as GLR2 in the manuscript; (82), and 3.4 (83) have been shown to control specific cell-type, tissue-type, developmental and environmental expression patterns in plants. Those of ordinary skill in the art can either digest the desired region using restriction enzymes and ligase to clone the plant glutamate promoters or use amplification, such as PCR, techniques with the incorporation of restriction or recombination sites to clone the plant glutamate receptor promoters 5' to the desired polynucleotide. A plant glutamate receptor promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

In another embodiment of the invention, a DNA construct comprising a plant sulphate transporter promoter operably linked to polynucleotides that encode the desired polypeptide of the invention is used to make a transformed plant that selectively increases the transcript or RNA of the desired polypeptide of the invention in the same cells, tissues, and under the environmental conditions that express a plant sulphate transporter. It is understood to those of ordinary skill in the art that the regulatory sequences that comprise a plant promoter driven by RNA polymerase II reside in the region approximately 2900 to 1200 basepairs up-stream (5') of the translation initiation site or start codon (ATG). A plant sulphate transporter promoter is the −2000 to −1 basepair region genes that include, but is not limited to, the *Arabidopsis thaliana* sulphate transporters (SULTR or AtSULTR). The promoters for the following SULTR genes, SULTR1;1, SULTR1;2 (84), SULTR 1;3; (85), SULTR2;1 (86), and SULTR3;5 (87) have been shown to control specific cell-type, tissue-type, developmental and environmental expression patterns in plants. Those of ordinary skill in the art can either digest the desired region using restriction enzymes and ligase to clone the plant glutamate promoters or use amplification, such as PCR, techniques with the incorporation of restriction or recombination sites to clone the plant sulphate transporter promoters 5' to the desired polynucleotide. A plant sulphate transporter promoter for these purposes normally means the following regions upstream (5') to the start codon between −200 to −1 basepairs, preferably at least between −500 to −1 basepairs, preferably at least between −1000 to −1 basepairs, more preferably at least between −1500 to −1 basepairs, and most preferably at −2000 to −1 basepairs.

Suitable Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (70, 88) and numerous expression cassettes and vectors and in vitro culture methods for plant cell or tissue transformation and regeneration of plants are known and available (89). The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, microbes, invertebrates or vertebrates.

It is known by those of ordinary skill in the art that there exist numerous expression systems available for expression of a nucleic acid encoding a protein of the present invention. There are many commercially available recombinant vectors to transform a host plant or plant cell. Standard molecular and cloning techniques (43, 46, 90) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter, such as ubiquitin, to direct transcription, a ribosome-binding site for translational initiation, and a transcription/translation terminator.

One of ordinary skill to the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs requires an appropriate transcriptional terminator to be attached downstream of the desired gene of the invention for proper expression in plants. Several such terminators are available and known to persons of ordinary skill in the art. These include, but are not limited to, the tml from CaMV and E9 from rbcS. Another example of a terminator sequence is the polyadenlyation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. An example of specific polyadenylation sequence in higher eukaryotes is ATTTA. Examples of plant polyadenylation signal sequences are AATAAA or AATAAT. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA (91, 92).

In addition, polynucleotides that encode a CDO, SAD, GAD, ADO, TPAT, SA, ssTDeHase, lsTDeHase or TDO can be placed in the appropriate plant expression vector used to transform plant cells. The polypeptide can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional CDO, SAD, GAD, ADO, TPAT, SA, ssTDeHase, lsTDeHase or TDO to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (93-96), C-terminus (97, 98) or internal (99-101) or tertiary structure (101). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (102, 103), iPSORT (104), SignalP (105), PrediSi (106), ELSpred (107) HSLpred (108) and PSLpred (109), MultiLoc (110), SherLoc (111), ChloroP (112), MITOPROT (113), Predotar (114) and 3D-PSSM (115). Additional methods and protocols are discussed in the literature (110).

Fusion of Two Gene Products

Two gene products can be fused together to increase the efficiency of an enzymatic reaction conducted by two enzymes (116-118). The two genes can be fused in-frame to be expressed as a single gene product with or without a linker. The linker can be a sequence that encodes a "tag" or a peptide.

Transformation of Host Cells

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (119).

Those of ordinary skill in the art can use different plant gene transfer techniques found in references for, but not limited to, the electroporation (120-124), microinjection (125, 126), lipofection (127), liposome or spheroplast fusions (128-130), *Agrobacterium* (131), direct gene transfer (132), T-DNA mediated transformation of monocots (133), T-DNA mediated transformation of dicots); (134, 135), microprojectile bombardment or ballistic particle acceleration (136-139), chemical transfection including CaCl2 precipitation, polyvinyl alcohol, or poly-L-ornithine (140), silicon carbide whisker methods (141, 142), laser methods (143, 144), sonication methods (145-147), polyethylene glycol methods (148), and vacuum infiltration (149) and transbacter (150).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include microbes, invertebrate, vertebrates or photosynthetic organisms. Preferred host cells are eukaryotic, preferably plant cells, such as those derived from monocotyledons, such as duckweed, corn, rice, sugarcane, wheat, bent grass, rye grass, Bermuda grass, Blue grass, and Fescue, or dicotyledons, including canola, cotton, camelina, lettuce, rapeseed, radishes, cabbage, sugarbeet, peppers, broccoli, potatoes and tomatoes, and legumes such as soybeans and bush beans.

One embodiment of the invention is a method for the production of hypotaurine or taurine by the following steps:

1. operably link a promoter to the 5' end of the polynucleotide for a functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional SAD gene product;
5. insert the polynucleotide construct (from step 4 above) into a vector; and
6. transform the vector containing the SAD construct into a plant or plant cell carrying a CDO construct or one that expresses a functional CDO gene product.

Another embodiment of the invention is a method for the production of hypotaurine or taurine by the following steps:

1. operably link a promoter to the 5' end of the polynucleotide for the functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional SAD gene product;
5. insert the polynucleotide construct (from step 4 above) into a vector;
6. transform the vector containing the SAD construct into a plant or plant cell; and
7. Sexually cross a plant (or fuse cells) carrying a CDO construct or one that expresses a functional CDO with a plant (or cells) carrying a SAD construct or one that expresses a functional SAD gene product.

Another embodiment of the invention is a method for the production of hypotaurine or taurine by the following steps:

1. In the same vector, operably link a promoter to the 5' end of the polynucleotide for the functional CDO gene product;
2. operably link a promoter to the 5' end of the polynucleotide for the functional SAD gene product;
3. insert the two polynucleotides into the vector in such a manner that both polynucleotides are expressed by one promoter or each polynucleotide is expressed by one promoter; and
4. transform the vector containing the CDO and SAD constructs into a plant or plant cell.

Another embodiment of the invention is a method for the production of hypotaurine or taurine by the following steps:

1. operably link a promoter to the 5' end of the polynucleotide for a functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional GAD gene product;
5. insert the polynucleotide construct (from step 4 above) into a vector; and
6. transform the vector containing the GAD construct into a plant or plant cell carrying a CDO construct or one that expresses a functional CDO gene product.

Another embodiment of the invention is a method for the production of hypotaurine or taurine by the following steps:

1. operably link a promoter to the 5' end of the polynucleotide for the functional CDO gene product;
2. insert the polynucleotide construct (from step 1 above) into a vector;
3. transform the vector containing the CDO construct into a plant or plant cell;
4. operably link a promoter to the 5' end of the polynucleotide for the functional GAD gene product;
5. insert the polynucleotide construct (from step 4 above) into a vector;
6. transform the vector containing the GAD construct into a plant or plant cell; and
7. Sexually cross a plant (or fuse cells) carrying a CDO construct or one that expresses a functional CDO with a plant (or cells) carrying a GAD construct or one that expresses a functional GAD gene product.

Another embodiment of the invention is a method for the production of hypotaurine or taurine by the following steps:

1. In the same vector, operably link a promoter to the 5' end of the polynucleotide for the functional CDO gene product;

2. operably link a promoter to the 5' end of the polynucleotide for the functional GAD gene product;

3. insert the two polynucleotides into the vector in such a manner that both polynucleotides are expressed by one promoter or each polynucleotide is expressed by one promoter; and 4. transform the vector containing the CDO and GAD constructs into a plant or plant cell.

Another embodiment of the invention is a method for the production of hypotaurine or taurine by the following steps:

1. operably link a promoter to the 5' end of the polynucleotide for a functional CDO gene product;

2. insert the polynucleotide construct (from step 1 above) into a vector; transform the vector containing the CDO construct into a plant or plant cell.

Another embodiment of the invention is a method for the production of taurine by the following steps:

1. operably link a promoter to the 5' end of the polynucleotide for a functional SAD gene product;

2. insert the polynucleotide construct (from step 1 above) into a vector; transform the vector containing the SAD construct into a plant or plant cell.

Another embodiment of the invention is a method for the production of hypotaurine or taurine by the following steps:

1. operably link a promoter to the 5' end of the polynucleotide for a functional ADO gene product;

2. insert the polynucleotide construct (from step 1 above) into a vector; transform the vector containing the ADO construct into a plant or plant cell.

Another embodiment of the invention is a method for the production of taurine by the following steps:

1. operably link a promoter to the 5' end of the polynucleotide for a functional TPAT gene product;

2. insert the polynucleotide construct (from step 1 above) into a vector; transform the vector containing the TPAT construct into a plant or plant cell.

One embodiment of the invention is a method for the production of taurine by the following steps:

1. operably link a promoter to the 5' end of the polynucleotide for a functional TPAT gene product;

2. insert the polynucleotide construct (from step 1 above) into a vector;

3. transform the vector containing the TPAT construct into a plant or plant cell;

4. operably link a promoter to the 5' end of the polynucleotide for the functional SA gene product;

5. insert the polynucleotide construct (from step 4 above) into a vector; and 6. transform the vector containing the TPAT construct into a plant or plant cell carrying a SA construct or one that expresses a functional SA gene product.

Another embodiment of the invention is a method for the production of taurine by the following steps:

1. operably link a promoter to the 5' end of the polynucleotide for the functional TPAT gene product;

2. insert the polynucleotide construct (from step 1 above) into a vector;

3. transform the vector containing the TPAT construct into a plant or plant cell;

4. operably link a promoter to the 5' end of the polynucleotide for the functional SA gene product;

5. insert the polynucleotide construct (from step 4 above) into a vector;

6. transform the vector containing the SA construct into a plant or plant cell; and 7. Sexually cross a plant (or fuse cells) carrying a TPAT construct or one that expresses a functional TPAT with a plant (or cells) carrying a SA construct or one that expresses a functional SA gene product.

Another embodiment of the invention is a method for the production of taurine by the following steps:

1. In the same vector, operably link a promoter to the 5' end of the polynucleotide for the functional TPAT gene product;

2. operably link a promoter to the 5' end of the polynucleotide for the functional SA gene product;

3. insert the two polynucleotides into the vector in such a manner that both polynucleotides are expressed by one promoter or each polynucleotide is expressed by one promoter; and 4. transform the vector containing the TPAT and SA construct into a plant or plant cell.

Another embodiment of the invention is a method for the production of taurine by the following steps:

1. operably link a promoter to the 5' end of the polynucleotide for a functional small subunit of TDeHase (ssTDeHase) gene product;

2. insert the polynucleotide construct (from step 1 above) into a vector;

3. transform the vector containing the ssTDeHase construct into a plant or plant cell;

4. operably link a promoter to the 5' end of the polynucleotide for the functional large subunit of TDeHase (lsTDeHase) gene product;

5. insert the polynucleotide construct (from step 4 above) into a vector; and 6. transform the vector containing the lsTDeHase construct into a plant or plant cell carrying a ssTDeHase construct or one that expresses a functional ssTDeHase gene product.

Another embodiment of the invention is a method for the production of taurine by the following steps:

1. operably link a promoter to the 5' end of the polynucleotide for the functional ssTDeHase gene product;

2. insert the polynucleotide construct (from step 1 above) into a vector;

3. transform the vector containing the ssTDeHase construct into a plant or plant cell;

4. operably link a promoter to the 5' end of the polynucleotide for the functional lsTDeHase gene product;

5. insert the polynucleotide construct (from step 4 above) into a vector;

6. transform the vector containing the lsTDeHase construct into a plant or plant cell; and 7. Sexually cross a plant (or fuse cells) carrying a ssTDeHase construct or one that expresses a functional ssTDeHase with a plant (or cells) carrying a lsTDeHase construct or one that expresses a functional lsTDeHase gene product.

Another embodiment of the invention is a method for the production of taurine by the following steps:

1. In the same vector, operably link a promoter to the 5' end of the polynucleotide for the functional ssTDeHase gene product;

2. operably link a promoter to the 5' end of the polynucleotide for the functional lsTDeHase gene product;

3. insert the two polynucleotides into the vector in such a manner that both polynucleotides are expressed by one promoter or each polynucleotide is expressed by one promoter; and 4. transform the vector containing the ssTDeHase and lsTDeHase construct into a plant or plant cell.

Another embodiment of the invention is a method for the production of taurine by the following steps:

1. operably link a promoter to the 5' end of the polynucleotide for a functional TDO gene product;

2. insert the polynucleotide construct (from step 1 above) into a vector; transform the vector containing the TDO construct into a plant or plant cell.

Another embodiment of the invention is a method for the production of hypotaurine or taurine by the following steps:

1. operably link a promoter to the 5' end of the polynucleotide for a functional CDO fused in-frame to a functional SAD gene product;

2. insert the polynucleotide construct (from step 1 above) into a vector; transform the vector containing the CDO-SAD construct into a plant or plant cell.

Another embodiment of the invention is a method for the production of hypotaurine or taurine by the following steps:

1. operably link a promoter to the 5' end of the polynucleotide for a functional CDO fused with a linker in-frame to a functional SAD gene product;

2. insert the polynucleotide construct (from step 1 above) into a vector; transform the vector containing the CDO-linker-SAD construct into a plant or plant cell.

Another embodiment of the invention is a method for the production of hypotaurine or taurine by the following steps:

1. operably link a promoter to the 5' end of the polynucleotide for a functional SAD fused in-frame to a functional CDO gene product;

2. insert the polynucleotide construct (from step 1 above) into a vector; transform the vector containing the SAD-CDO construct into a plant or plant cell.

Another embodiment of the invention is a method for the production of hypotaurine or taurine by the following steps:

1. operably link a promoter to the 5' end of the polynucleotide for a functional SAD fused with a linker in-frame to a functional CDO gene product;

2. insert the polynucleotide construct (from step 1 above) into a vector; transform the vector containing the SAD-linker-CDO construct into a plant or plant cell.

Another embodiment of the invention is a method for the production of hypotaurine or taurine by the following steps:

1. operably link a promoter to the 5' end of the polynucleotide for a functional CDO fused in-frame to a functional GAD gene product;

2. insert the polynucleotide construct (from step 1 above) into a vector; transform the vector containing the CDO-GAD construct into a plant or plant cell.

Another embodiment of the invention is a method for the production of hypotaurine or taurine by the following steps:

1. operably link a promoter to the 5' end of the polynucleotide for a functional CDO fused with a linker in-frame to a functional GAD gene product;

2. insert the polynucleotide construct (from step 1 above) into a vector; transform the vector containing the CDO-linker-GAD construct into a plant or plant cell.

Another embodiment of the invention is a method for the production of hypotaurine or taurine by the following steps:

1. operably link a promoter to the 5' end of the polynucleotide for a functional GAD fused in-frame to a functional CDO gene product;

2. insert the polynucleotide construct (from step 1 above) into a vector; transform the vector containing the GAD-CDO construct into a plant or plant cell.

Another embodiment of the invention is a method for the production of hypotaurine or taurine by the following steps:

1. operably link a promoter to the 5' end of the polynucleotide for a functional GAD fused with a linker in-frame to a functional CDO gene product;

2. insert the polynucleotide construct (from step 1 above) into a vector; transform the vector containing the GAD-linker-CDO construct into a plant or plant cell.

Another embodiment of the invention is a method for the production of hypotaurine or taurine by the following steps:

1. operably link a promoter to the 5' end of the polynucleotide for a functional TPAT fused in-frame to a functional SA gene product;

2. insert the polynucleotide construct (from step 1 above) into a vector; transform the vector containing the TPAT-SA construct into a plant or plant cell.

Another embodiment of the invention is a method for the production of hypotaurine or taurine by the following steps:

1. operably link a promoter to the 5' end of the polynucleotide for a functional TPAT fused with a linker in-frame to a functional SA gene product;

2. insert the polynucleotide construct (from step 1 above) into a vector; transform the vector containing the TPAT-linker-SA construct into a plant or plant cell.

Another embodiment of the invention is a method for the production of hypotaurine or taurine by the following steps:

1. operably link a promoter to the 5' end of the polynucleotide for a functional SA fused in-frame to a functional TPAT gene product;

2. insert the polynucleotide construct (from step 1 above) into a vector; transform the vector containing the SA-TPAT construct into a plant or plant cell.

Another embodiment of the invention is a method for the production of hypotaurine or taurine by the following steps:

1. operably link a promoter to the 5' end of the polynucleotide for a functional SA fused with a linker in-frame to a functional TPAT gene product;

2. insert the polynucleotide construct (from step 1 above) into a vector; transform the vector containing the SA-linker-TPAT construct into a plant or plant cell.

Another embodiment of the invention is a method for the production of hypotaurine or taurine by the following steps:

1. operably link a promoter to the 5' end of the polynucleotide for a functional ssTDeHase fused in-frame to a functional lsTDeHase gene product;

2. insert the polynucleotide construct (from step 1 above) into a vector; transform the vector containing the ssTDeHase-lsTDeHase construct into a plant or plant cell.

Another embodiment of the invention is a method for the production of hypotaurine or taurine by the following steps:

1. operably link a promoter to the 5' end of the polynucleotide for a functional ssTDeHase fused with a linker in-frame to a functional lsTDeHase gene product;

2. insert the polynucleotide construct (from step 1 above) into a vector; transform the vector containing the ssTDeHase-linker-lsTDeHase construct into a plant or plant cell.

Another embodiment of the invention is a method for the production of hypotaurine or taurine by the following steps:

1. operably link a promoter to the 5' end of the polynucleotide for a functional lsTDeHase fused in-frame to a functional ssTDeHase gene product;

2. insert the polynucleotide construct (from step 1 above) into a vector; transform the vector containing the lsTDeHase-ssTDeHase construct into a plant or plant cell.

Another embodiment of the invention is a method for the production of hypotaurine or taurine by the following steps:

1. operably link a promoter to the 5' end of the polynucleotide for a functional lsTDeHase fused with a linker in-frame to a functional ssTDeHase gene product;

2. insert the polynucleotide construct (from step 1 above) into a vector; transform the vector containing the lsTDeHase-linker-ssTDeHase construct into a plant or plant cell.

Suitable Plants

The methods described above may be applied to transform a wide variety of plants, including decorative or recreational plants or crops, but are particularly useful for treating commercial and ornamental crops. Examples of plants that may be transformed in the present invention include, but are not limited to, Acacia, alfalfa, algae, aneth, apple, apricot, artichoke, arugula, asparagus, avocado, banana, barley, beans, beech, beet, Bermuda grass, bent grass, blackberry, blueberry, Blue grass, broccoli, Brussels sprouts, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jicama, kiwifruit, lettuce, leeks, lemon, lime, Loblolly pine, maize, mango, melon, mushroom, nectarine, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, seaweed, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yams, and zucchini. Other suitable hosts include bacteria, fungi, algae and other photosynthetic organisms, and animals including vertebrate and invertebrates.

Once transformed, the plant may be treated with other "active agents" either prior to or during the exposure of the plant to stress to further decrease the effects of plant stress. "Active agent," as used herein, refers to an agent that has a beneficial effect on the plant or increases production of amino acid production by the plant. For example, the agent may have a beneficial effect on the plant with respect to nutrition, and the resistance against, or reduction of, the effects of plant stress. Some of these agents may be precursors of end products for reaction catalyzed by CDO, SAD, GAD, ADO, TPAT, SA, ssTDeHase or lsTDeHase. These compounds could promote growth, development, biomass and yield, and change in metabolism. In addition to the twenty amino acids that are involved in protein synthesis specifically sulfur containing amino acids methionine, and cysteine, other amino acids such as glutamate, glutamine, serine, alanine and glycine, sulfur containing compounds such as fertilizer, sulfite, sulfide, sulfate, taurine, hypotaurine, cysteate, 2-sulfacetaldehyde, homotaurine, homocysteine, cystathionine, N-acetyl thiazolidine 4 carboxylic acid (ATCA), glutathione, or bile, or other non-protein amino acids, such as GABA, citrulline and ornithine, or other nitrogen containing compounds such as polyamines may also be used to activate CDO, SAD, GAD, ADO, TPAT, SA, ssTDeHase, lsTDeHase or TDO. Depending on the type of gene construct or recombinant expression cassette, other metabolites and nutrients may be used to activate CDO, SAD, GAD, ADO, TPAT, SA, ssTDeHase, lsTDeHase, or TDO. These include, but are not limited to, sugars, carbohydrates, lipids, oligopeptides, mono-(glucose, arabinose, fructose, xylose, and ribose) di-(sucrose and trehalose) and polysaccharides, carboxylic acids (succinate, malate and fumarate) and nutrients such as phosphate, molybdate, or iron.

Accordingly, the active agent may include a wide variety of fertilizers, pesticides and herbicides known to those of ordinary skill in the art (151). Other greening agents fall within the definition of "active agent" as well, including minerals such as calcium, magnesium and iron. The pesticides protect the plant from pests or disease and may be either chemical or biological and include fungicides, bactericides, insecticides and anti-viral agents as known to those of ordinary skill in the art.

In some embodiments properties of a transgenic plant are altered using an agent which increases sulfur concentration in cells of the transgenic plant, such as fertilizer, sulfur, sulfite, sulfide, sulfate, taurine, hypotaurine, homotaurine, cysteate, 2-sulfacetaldehyde, N-acetyl thiazolidine 4 carboxylic acid (ATCA), glutathione, and bile. In other embodiments, the agent increases nitrogen concentration. Amino acids, either naturally occurring in proteins (e.g., cysteine, methionine, glutamate, glutamine, serine, alanine, or glycine) or which do not naturally occur in proteins (e.g., GABA, citrulline, or ornithine) and/or polyamines can be used for this purpose.

Expression in Prokaryotes

The use of prokaryotes as hosts includes strains of *E. coli*. However, other microbial strains including, but not limited to, *Bacillus* (152) and *Salmonella* may also be used. Commonly used prokaryotic control sequences include promoters for transcription initiation, optionally with an operator, along with ribosome binding site sequences. Commonly used prokaryotic promoters include the beta lactamase (153), lactose (153), and tryptophan (154) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art.

Expression in Non-Plant Eukaryotes

The present invention can be expressed in a variety of eukaryotic expression systems such as yeast, insect cell lines, and mammalian cells which are known to those of ordinary skill in the art. For each host system there are suitable vectors that are commercially available (e.g., Invitrogen, Startagene, GE Healthcare Life Sciences). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins in yeast is well known to those of ordinary skill in the art (155, 156). The most widely used yeasts are *Saccharomyces cerevisiae* and *Pichia pastoris*. Insect cell lines that include, but are not limited to, mosquito larvae, silkworm, armyworm, moth, and Drosophila cell lines can be used to express proteins of the present invention using baculovirus-derived vectors. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines.

A protein of the present invention, once expressed in any of the non-plant eukaryotic systems can be isolated from the organism by lysing the cells and applying standard protein isolation techniques to the lysates or the pellets. The monitoring of the purification process can be accomplished by using western blot techniques or radioimmunoassay of other standard immunoassay techniques.

Pharmaceutical Compositions

The invention provides pharmaceutical compositions which comprise extracts of one or more transgenic plants described above. Plant extracts containing taurine and hypotaurine can be used to synthesize or manufacture homotaurine or other taurine derivatives (157, 158), taurine-conjugates (159) or taurine-polymers (160) that may have a wide range of commercial and medicinal applications (161). Some taurine derivatives can function as organogelators (162) or dyes (163) and can be used in nanosensor synthesis (164). Some taurine derivatives have anticonvulsant (157) or anti-cancer (165) properties. Other taurine derivatives are used in the treatment of alcoholism (166, 167). Taurine-conjugated carboxyethylester-polyrotaxanes increase anti-coagulant activity (168). Taurine-containing polymers may increase wound healing (169, 170). Taurine linked polymers such as poly gamma-glutamic acid-sulfonates are biodegradable and may have applications in the development of drug delivery systems, environmental materials, tissue engineering, and medical materials (171). Extracts from taurine-containing plants may be used in pharmaceutical or medicinal compositions to deliver taurine, hypotaurine, taurine-conjugates, or taurine-polymers for use in the treatment of congestive heart failure, high blood pressure, hepatitis, high cholesterol, fibrosis, epilepsy, autism, attention deficit-hyperactivity disorder, retinal degeneration, diabetes, and alcoholism. It is also used to improve mental performance and as an antioxidant.

Pharmaceutically acceptable vehicles of taurine, taurine derivatives, taurine-conjugates, or taurine-polymers are tablets, capsules, gel, ointment, film, patch, powder or dissolved in liquid form.

Nutritional Supplements and Feeds

Transgenic plants containing taurine or hypotaurine may be consumed or used to make extracts for nutritional supplements. Transgenic plant parts that have elevated levels of taurine or hypotaurine may be used for human consumption. The plant parts may include but are not limited to leaves, stalks, stems, tubers, stolons, roots, petioles, cotyledons, seeds, fruits, grain, strover, nuts, flowers, petioles, pollen, buds, or pods. Extracts from transgenic plants containing taurine or hypotaurine may be used as nutritional supplements, as an antioxidant or to improve physical or mental performance. The extracts may be used in the form of a liquid, powder, capsule or tablet.

Transgenic plants containing taurine or hypotaurine may be used as fish or animal feed or used to make extracts for the supplementation of animal feed. Plant parts that have elevated levels of taurine or hypotaurine may be used as animal or fish feed include but are not limited to leaves, stalks, stems, tubers, stolons, roots, petioles, cotyledons, seeds, fruits, grain, strover, nuts, flowers, petioles, buds, pods, or husks. Extracts from transgenic plants containing taurine or hypotaurine may be used as feed supplements in the form of a liquid, powder, capsule or tablet.

Definitions

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription.

The term "plant promoter" refers to a promoter capable of initiating transcription in plant cells.

The term "microbe promoter" refers to a promoter capable of initiating transcription in microbes.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as fungi, yeast, bacteria, actinomycetes, algae and protozoa, as well as other unicellular structures.

The term "plant" includes whole plants, and plant organs, and progeny of same. Plant organs comprise, e.g., shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like). The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "plant storage organ" includes roots, seeds, tubers, fruits, and specialized stems.

The term "constitutive" refers to a promoter that is active under most environmental and developmental conditions, such as, for example, but not limited to, the CaMV 35S promoter and the nopaline synthase terminator.

The term "tissue-preferred promoter" refers to a promoter that is under developmental control or a promoter that preferentially initiates transcription in certain tissues.

The term "tissue-specific promoter" refers to a promoter that initiates transcription only in certain tissues.

The term "cell-type specific promoter" refers to a promoter that primarily initiates transcription only in certain cell types in one or more organs.

The term "inducible promoter" refers to a promoter that is under environmental control.

The terms "encoding" and "coding"" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The terms "cysteine dioxygenase" and "CDO" refer to the protein (EC:1.13.11.20) that catalyzes the following reaction:

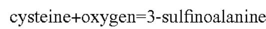

NOTE: 3-sulfinoalanine is another name for cysteine sulfinic acid, cysteine sulfinate, 3-sulphino-L-alanine, 3-sulfino-alanine, 3-sulfino-L-alanine, L-cysteine sulfinic acid, L-cysteine sulfinic acid, cysteine hydrogen sulfite ester or alanine 3-sulfinic acid The terms "sulfinoalanine decarboxylase" and "SAD" refer to the protein (4.1.1.29) that catalyzes the following reaction:

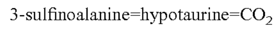

NOTE: SAD is another name for cysteine-sulfinate decarboxylase, L-cysteine sulfinic acid decarboxylase, cysteine-sulfinate decarboxylase, CADCase/CSADCase, CSAD, cysteic decarboxylase, cysteine sulfinic acid decarboxylase, cysteine sulfinate decarboxylase, sulfoalanine decarboxylase, sulphinoalanine decarboxylase, and 3-sulfino-L-alanine carboxy-lyase.

NOTE: the SAD reaction is also catalyzed by GAD (4.1.1.15) (glutamic acid decarboxylase or glutamate decarboxylase).

Other names for hypotaurine are 2-aminoethane sulfinate, 2-aminoethylsulfinic acid, and 2-aminoethanesulfinic acid Other names for taurine are 2-aminoethane sulfonic acid, aminoethanesulfonate, L-taurine, taurine ethyl ester, and taurine ketoisocaproic acid 2-aminoethane sulfinate.

The terms "cysteamine dioxygenase" and "ADO" refer to the protein (EC 1.13.11.19) that catalyzes the following reaction:

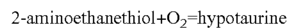

ADO is another name for 2-aminoethanethiol:oxygen oxidoreductase, persulfurase, cysteamine oxygenase, and cysteamine:oxygen oxidoreductase.

Other names for 2-aminoethanethiol are cysteamine or 2-aminoethane-1-thiol, b-mercaptoethylamine, 22-mercaptoethylamine, decarboxycysteine, and thioethanolamine.

The terms "taurine-pyruvate aminotransferase" and "TPAT" refer to the protein (EC 2.6.1.77) that catalyzes the following reaction:

L-alanine+2-sulfoacetaldehyde=taurine+pyruvate

TPAT is another name for taurine transaminase or Tpa

The terms "sulfoacetaldehyde acetyltransferase" and "SA" refer to the protein (EC:2.3.3.15) that catalyzes the following reaction:

acetyl phosphate+sulfite=sulfoacetaldehyde+orthophosphate

SA is another name for acetyl-phosphate:sulfite S-acetyltransferase or Xsc

The terms "taurine dehydrogenase" and "TDeHase" refer to the protein (EC:1.4.2.-) that catalyzes the following reaction:

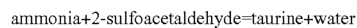

TDeHase is another name for taurine:oxidoreductase, taurine:ferricytochrome-c oxidoreductase, tauX or tauY The terms "taurine dioxygenase" and "TDO" refer to the protein (EC:1.14.11.17) that catalyzes the following reaction:

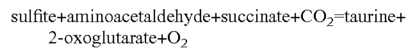

TDO is another name for 2-aminoethanesulfonate dioxygenase, alpha-ketoglutarate-dependent taurine dioxygenase, taurine, 2-oxoglutarate:O2 oxidoreductase or tauD 2-oxoglutarate is another name for alpha-ketoglutarate The term "functional" with reference to CDO, SAD, GAD, ADO, TPAT, SA, ssTDeHase, lsTDeHase or TDO refers to peptides, proteins or enzymes that catalyze the CDO, SAD, GAD, ADO, TPAT, SA, TDeHase or TDO reactions, respectively.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic plant" includes reference to a plant, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell, cell line, callus, tissue, plant part or plant, the genotype of which has been altered by the presence of heterologous nucleic acid including those transgenic plants altered or created by sexual crosses or asexual propagation from the initial transgenic plant. The term "transgenic" does not encompass the alteration of the genome by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt solution. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (172), where the $T_m$=81.5° C.+16.6 (log M)+0.41 (% GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature (90, 173). Unless otherwise stated, in the present application high stringency is defined as hybridization in 4×SSC, 5× Denhardt solution (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence," "comparison window," "sequence identity," "percentage of sequence identity," and "substantial identity."

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT, (174) can perform an optimal alignment of sequences for comparison using a homology alignment algorithm called GAP (175), search for similarity using Tfasta and Fasta (176), by computerized implementations of these algorithms widely available on-line or from various vendors (Intelligenetics, Genetics Computer Group). CLUSTAL allows for the alignment of multiple sequences (177-179) and program PileUp can be used for optimal global alignment of multiple sequences (180). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (175) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (181).

Unless otherwise stated, sequence identity or similarity values refer to the value obtained using the BLAST 2.0 suite of programs using default parameters (182). As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (183, 184) and XNU (185).

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch (186), thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (175). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

REFERENCES

1. Suzuki et al., 1989. U.S. Pat. No. 4,877,447.

2. Sturman 1988. "Taurine in development." J Nutr, 118: 1169-1176.

3. Sturman et al., 1980. "The biology of taurine in nutrition and development." Adv Nutr Res, 3: 231-299.

4. Chen et al., 1998. "Effect of taurine on human fetal neuron cells: Proliferation and differentiation." Adv Exp Med Biol, 442: 397-403.

5. El Idrissi et al., 1999. "Growth factors and taurine protect against excitotoxicity by stabilizing calcium homeostasis and energy metabolism." J Neurosci, 19: 9459-9468.

6. El Idrissi et al., 2003. "Taurine regulates mitochondrial calcium homeostasis." Adv Exp Med Biol, 526: 527-536.

7. Trenkner 1990. "Possible role of glutamate with taurine in neuron-glia interaction during cerebellar development." Prog Clin Biol Res, 351: 133-140.

8. Wu et al., 2005. "Mode of action of taurine as a neuroprotector." Brain Res, 1038: 123-131.

9. Schaffer et al., 2000. "Role of osmoregulation in the actions of taurine." Amino Acids, 19: 527-546.

10. Chapman et al., 1993. "Taurine and the heart." Cardiovasc Res, 27: 358-363.

11. Tabassuma et al., 2006. "Attenuation of tamoxifen-induced hepatotoxicity by taurine in mice." Clin Chim Acta, 370: 129-136.

12. Rocket et al., 2007. "The osmolyte taurine protects against ultraviolet B radiation-induced immunosuppression." J Immunol, 179: 3604-3612.

13. Milei et al., 1992. "Reduction of reperfusion injury with preoperative rapid intravenous infusion of taurine during myocardial revascularization." Am Heart J, 123: 339-345.

14. Militante et al., 2002. "Treatment of hypertension with oral taurine." Endocrinology, 147: 3276-3284.

15. Fujita et al., 1987. "Effects of increased adrenomedullary activity and taurine in young patients with borderline hypertension." Circulation, 75: 525-532.

16. McCown et al., 1987. "Amino acid influences on seizures elicited within the inferior colliculus." J Pharmacol Exp Ther, 243: 603-608.

17. Matsuyama et al., 1983. "The effect of taurine administration on patients with acute hepatitis." Prog Clin Biol Res, 125: 461-468.

18. Ikeda 1977. "Effects of taurine on alcohol withdrawal." Lancet, 2: 509.

19. Franconi et al., 2004. "Is taurine beneficial in reducing risk factors for diabetes mellitus?" Neurochem Res, 29: 143-150.

20. Paula-Lima et al., 2005. "Activation of GABAA receptors by taurine and muscimol blocks the neurotoxicity of [beta]-amyloid in rat hippocampal and cortical neurons." Neuropharmacology, 49: 1140-1148.

21. Nakamori et al., 1993. "Quantitative evaluation of the effectiveness of taurine in protecting the ocular surface against oxidant." Chem Pharm Bull, 41: 335-338.

22. Zhang et al., 2004. "Beneficial effects of taurine on serum lipids in overweight or obese non-diabetic subjects." Amino Acids, 26: 267-271.

23. Yokogoshi et al., 1999. "Dietary taurine enhances cholesterol degradation and reduces serum and liver cholesterol concentrations in rats fed a high-cholesterol diet." J Nutr, 129: 1705-1712.

24. Yamamoto et al., 2000. "Dietary taurine decreases hepatic secretion of cholesterol ester in rats fed a high-cholesterol diet." Pharmacology, 60: 27-33.

25. Green et al., 1991. "Antioxidant role and subcellular location of hypotaurine and taurine in human neutrophils." Biochim Biophys Acta, 1073: 91-97.

26. Gürer et al., 2001. "Antioxidant effect of taurine against lead-induced oxidative stress." Arch Environ Contam Toxicol, 41: 397-402.

27. Das et al., 2008. "Taurine provides antioxidant defense against NaF-induced cytotoxicity in murine hepatocytes." Pathophysiology, 15: 181-190.

28. Zhang et al., 2004. " Role of taurine supplementation to prevent exercise-induced oxidative stress in healthy young men." Amino Acids, 26: 203-207.

29. Williams 2005. "Dietary supplements and sports performance: Amino acids." Journal of the International Society of Sports Nutrition, 2: 63-67.

30. da Silva et al., 2008. "Penetration profile of taurine in the human skin and its distribution in skin layers." Pharm Res, 25: 1846-1850.

31. Knopf et al., 1978. "Taurine: An essential nutrient for the cat." J Nutr, 108: 773-778.

32. Gibson et al., 2007. "Supplementation of taurine and methionine to all-plant protein diets for rainbow trout (*Oncorhynchus mykiss*)." Aquaculture, 269: 514-524.

33. Schweigen 1967. "Low-molecular-weight compounds in Macrocystis pyrifera, a marine algae." Arch Biochem Biophys, 118: 383-387.

34. Huxtable 1992. "Physiological actions of taurine." Physiol Rev, 72: 101-163.

35. Kataoka et al., 1986. "Occurrence of taurine in plants." Agric Biol Chem, 50: 1887-1888.

36. Murray et al., 1989. "Codon usage in plant genes." Nucleic Acids Research, 17: 477-498.

37. Stemmer 1997. U.S. Pat. No. 5,605,793.

38. Short 1999. U.S. Pat. No. 5,965,408.

39. Langenheim et al., 1982. Botany: Plant Biology and its Relation to Human Affairs. New York: John Wiley & Sons Inc.

40. Vasil 1984. Cell Culture and Somatic Cell Genetics of Plants: Laboraory Procedures and Their Applications. Orlando: Academic Press.

41. Stanier et al., 1986. The Microbial World. New Jersey: Prentice-Hall.

42. Dhringra et al., 1985. Basic plant pathology methods. Boca Raton, Fla.: CRC Press.

43. Maniatis et al., 1985. Molecular Cloning: A Laboratory Manual: DNA Cloning. New York: Cold Spring Harbor.

44. Gait 1984. Oligonucleotide Synthesis-A Practical Approach. Washington, D.C.: IRL Press.

45. Hames et al., 1984. Nucleic Acid Hybridization: A Practical Approach. Washington D.C.: IRL Press.

46. Watson et al., 1992. Recombinant DNA. New York: Scientific American Books.

47. Szewczyk et al., 2006. "Fusion PCR and gene targeting in Aspergillus nidulans." Nat Protoc, 1: 3111-3121.

48. Ho et al., 1989. "Site-directed mutagenesis by overlap extension using the polymerase chain reaction." Gene, 77: 51-59.

49. Fuhrmann et al., 1999. "A synthetic gene coding for the green fluorescent protein (GFP) is a versatile reporter in *Chlamydomonas reinhardtii*." Plant J, 19: 353-361.

50. Mandecki et al., 1988. "FokI method of gene synthesis." Gene, 68: 101-107.

51. Stemmer 1995. "Single-step assembly of a gene and entire plasmid from large numbers of oligodeoxyribonucleotides." Gene, 164: 49-53.

52. Gao et al., 2003. "Thermodynamically balanced inside-out (TBIO) PCR-based gene synthesis: a novel method of primer design for high-fidelity assembly of longer gene sequences." Nucleic Acids Res, 31: e143.

53. Young et al., 2004. "Two-step total gene synthesis method." Nucleic Acids Res, 32: e59.

54. van Der Krol et al., 1999. "Developmental and wound-, cold-, desiccation-, ultraviolet-B-stress-induced modulations in the expression of the petunia zinc finger transcription factor gene ZPT2-2." Plant Physiol, 121: 1153-62.

55. Shinmyo et al., 1998. "Metabolic engineering of cultured tobacco cells." Biotechnol Bioeng, 58: 329-32.

56. Sohal et al., 1999. "The promoter of a *Brassica napus* lipid transfer protein gene is active in a range of tissues and stimulated by light and viral infection in transgenic *Arabidopsis*." Plant Mol Biol, 41: 75-87.

57. Cormack et al., 2002. "Leucine zipper-containing WRKY proteins widen the spectrum of immediate early elicitor-induced WRKY transcription factors in parsley." Biochim Biophys Acta, 1576: 92-100.

58. Eulgem et al., 1999. "Early nuclear events in plant defence signalling: rapid gene activation by WRKY transcription factors." EMBO (Eur Mol Biol Organ) J, 18: 4689-99.

59. Lebel et al., 1998. "Functional analysis of regulatory sequences controlling PR-1 gene expression in *Arabidopsis*." Plant J, 16: 223-33.

60. Ngai et al., 1997. "Light-induced transcriptional repression of the pea AS 1 gene: identification of cis-elements and transfactors." Plant J, 12: 1021-34.

61. Kucho et al., 1999. "CO(2)-responsive transcriptional regulation of CAH1 encoding carbonic anhydrase is mediated by enhancer and silencer regions in *Chlamydomonas reinhardtii*." Plant Physiol, 121: 1329-38.

62. Kucho et al., 2003. "Cis-acting elements and DNA-binding proteins involved in CO2-responsive transcriptional activation of Cahl encoding a periplasmic carbonic anhydrase in *Chlamydomonas reinhardtii*." Plant Physiol, 133: 783-93.

63. Chen et al., 1996. "The promoter of a H202-inducible, *Arabidopsis* glutathione S-transferase gene contains closely linked OBF- and OBP1-binding sites." Plant J, 10: 955-66.

64. Chen et al., 1999. "The auxin, hydrogen peroxide and salicylic acid induced expression of the *Arabidopsis* GST6 promoter is mediated in part by an ocs element." Plant J, 19: 667-77.

65. Lu et al., 1998. "Sugar response sequence in the promoter of a rice alpha-amylase gene serves as a transcriptional enhancer." J Biol Chem, 273: 10120-31.

66. Leubner-Metzger et al., 1998. "Ethylene-responsive element binding protein (EREBP) expression and the transcriptional regulation of class I beta-1,3-glucanase during tobacco seed germination." Plant Mol Biol, 38: 785-95.

67. Hudspeth et al., 1992. "Expression of maize phosphoenolpyruvate carboxylase in transgenic tobacco: Effects on biochemistry and physiology." Plant Physiol, 98: 458-464.

68. de Framond 1991. "A metallothionein-like gene from maize (*Zea mays*). Cloning and characterization." FEBS Lett, 290: 103-6.

69. Hudspeth et al., 1996. "Characterization and expression of metallothionein-like genes in cotton." Plant Mol Biol, 31: 701-5.

70. Herrera-Estrella et al., 1983. "Expression of chimaeric genes transferred into plant cells using a Ti-plasmid-derived vector." Nature, 303: 209-213.

71. Pathirana et al., 1997. "Analyses of phosphoenolpyruvate carboxylase gene structure and expression in alfalfa nodules." Plant J, 12: 293-304.

72. Yang et al., 2002. "Isolation and characterization of the orchid cytokinin oxidase DSCKX1 promoter." J Exp Bot, 53: 1899-1907.

73. Moon et al., 2004. "Developmental regulation of peach ACC oxidase promoter-GUS fusions in transgenic tomato fruits." J Exp Bot, 55: 1519-1528.

74. Avsian-Kretchmer et al., 2004. "The salt-stress signal transduction pathway that activates the gpx1 promoter is mediated by intracellular H202, different from the pathway induced by extracellular H2O2." Plant Physiol, 135: 1685-96.

75. Wu et al., 2007. "Functional analysis of a cotton glucuronosyltransferase promoter in transgenic tobaccos." Cell Res, 17: 174-183.

76. Shelp et al., 1999. "Metabolism and functions of gamma-aminobutyric acid." Trends Plant Sci, 41: 446-452.

77. Baum et al., 1993. "A plant glutamate decarboxylase containing a calmodulin binding domain. Cloning, sequence, and functional analysis." J Biol Chem, 268: 19610-19617.

78. Gallego et al., 1995. "A role for glutamate decarboxylase during tomato ripening: the characterisation of a cDNA encoding a putative glutamate decarboxylase with a calmodulin-binding site." Plant Mol Biol, 27: 1143-1151.

79. Yun et al., 1998. "Cloning and characterization of tobacco cDNA encoding calcium/calmodulin-dependent glutamate decarboxylase." Mol Cell, 8: 125-129.

80. Oh et al., 2005. "Cloning and characterization of a rice cDNA encoding glutamate decarboxylase." J Biochem Mol Biol, 38: 595-601.

81. Chiu et al., 2002. "Phylogenetic and expression analysis of the glutamate-receptor-like gene family in *Arabidopsis thaliana*." Mol Biol Evol, 19: 1066-1082.

82. Kim et al., 2001. "Overexpression of the AtG1uR2 gene encoding an *Arabidopsis* homolog of mammalian glutamate receptors impairs calcium utilization and sensitivity to ionic stress in transgenic plants." Plant Cell Physiol, 42: 74-84.

83. Meyerhoff et al., 2005. "AtGLR3.4, a glutamate receptor channel-like gene is sensitive to touch and cold." Planta, 222: 418-27.

84. Maruyama-Nakashita et al., 2004. "Regulation of high-affinity sulphate transporters in plants towards systematic analysis of sulphur signalling and regulation." J Exp Bot, 55: 1843-1849.

85. Yoshimoto et al., 2003. "Phloem-localizing sulfate transporter, Sultr1;3, mediates re-distribution of sulfur from source to sink organs in *Arabidopsis*." Plant Physiol, 131: 1511-1517.

86. Awazuhara et al., 2005. "The function of SULTR2;1 sulfate transporter during seed development in *Arabidopsis thaliana*." Physiol Plant, 125: 95-105.

87. Kataoka et al., 2004. "Root-to-shoot transport of sulfate in *Arabidopsis:* Evidence for the role of SULTR3;5 as a component of low-affinity sulfate transport system in the root vasculature." Plant Physiol, 136: 4198-4204.

88. An et al., 1985. "New cloning vehicles for transformation of higher plants." EMBO (Eur Mol Biol Organ) J, 4: 277-284.

89. Gruber et al., 1993. Vectors for plant transformation. In Glick B R & J E Thompson, editors. Methods in Plant Molecular Biology and Biotechnology 89-119. Baco Raton, Fla.: CRC Press.

90. Ausubel et al., 1995. Current Protocols in Molecular Biology. New York: Greene Publishing and Wiley-Interscience.

91. Newman et al., 1993. "DST sequences, highly conserved among plant SAUR genes, target reporter transcripts for rapid decay in tobacco." Plant Cell, 5: 701-14.

92. Ohme-Takagi et al., 1993. "The effect of sequences with high AU content on mRNA stability in tobacco." Proc Natl Acad Sci USA, 90: 11811-5.

93. von Heijne 1986. "Mitochondrial targeting sequences may form amphiphilic helices." EMBO (Eur Mol Biol Organ) J, 5: 1335-1342.

94. Swinkels et al., 1991. "A novel, cleavable peroxisomal targeting signal at the amino-terminus of the rat 3-ketoacyl-CoA thiolase." EMBO (Eur Mol Biol Organ) J, 10: 3255-62.

95. Rusch et al., 1995. "Protein transport via amino-terminal targeting sequences: Common themes in diverse systems." Mol Membr Biol, 12: 295-307.

96. Soll et al., 1998. "Protein translocation into and across the chloroplastic envelope membranes." Plant Mol Biol, 38: 191-207.

97. Gould et al., 1988. "Identification of peroxisomal targeting signals located at the carboxy terminus of four peroxisomal proteins." J Cell Biol, 107: 897-905.

98. Gould et al., 1989. "A conserved tripeptide sorts proteins to peroxisomes." J Cell Biol, 108: 1657-64.

99. McCammon et al., 1994. "An internal region of the peroxisomal membrane protein PMP47 is essential for sorting to peroxisomes." J Cell Biol, 124: 915-25.

100. Cokol et al., 2000. "Finding nuclear localization signals." EMBO Rep, 1: 411-5.

101. Helenius et al., 2001. "Intracellular functions of N-linked glycans." Science, 291: 2364-9.

102. Emanuelsson et al., 2007. "Locating proteins in the cell using TargetP, SignalP and related tools." Nat Protoc, 2: 953-971.

103. Emanuelsson et al., 2000. "Predicting subcellular localization of proteins based on their N-terminal amino acid sequence." J Mol Biol, 300: 1005-1016.

104. Bannai et al., 2002. "Extensive feature detection of N-terminal protein sorting signals." Bioinformatics, 18: 298-305.

105. Bendtsen et al., 2004. "Improved prediction of signal peptides: SignalP 3.0." J Mol Biol, 340: 783-95.

106. Hiller et al., 2004. "PrediSi: prediction of signal peptides and their cleavage positions." Nucleic Acids Res, 32: W375-9.

107. Bhasin et al., 2004. "ESLpred: SVM-based method for subcellular localization of eukaryotic proteins using dipeptide composition and PSI-BLAST." Nucleic Acids Res, 32: W414-9.

108. Garg et al., 2005. "Support vector machine-based method for subcellular localization of human proteins using amino acid compositions, their order, and similarity search." J Biol Chem, 280: 14427-32.

109. Bhasin et al., 2005. "PSLpred: prediction of subcellular localization of bacterial proteins." Bioinformatics, 21: 2522-4.

110. Hoglund et al., 2006. "MultiLoc: prediction of protein subcellular localization using N-terminal targeting sequences, sequence motifs and amino acid composition." Bioinformatics, 22: 1158-65.

111. Shatkay et al., 2007. "SherLoc: high-accuracy prediction of protein subcellular localization by integrating text and protein sequence data." Bioinformatics, 23: 1410-7.

112. Emanuelsson et al., 1999. "ChloroP, a neural network-based method for predicting chloroplast transit peptides and their cleavage sites." Protein Sci, 8: 978-984.

113. Claros et al., 1996. "Computational method to predict mitochondrially imported proteins and their targeting sequences." Eur J Biochem, 241: 779-86.

114. Small et al., 2004. "Predotar: A tool for rapidly screening proteomes for N-terminal targeting sequences." Proteomics, 4: 1581-1590.

115. Kelley et al., 2000. "Enhanced genome annotation using structural profiles in the program 3D-PSSM." J Mol Biol, 299: 499-520.

116. Bülow et al., 1991. "Multienzyme systems obtained by gene fusion." Trends Biotechnol, 9: 226-231.

117. Seo et al., 2000. "Characterization of a bifunctional enzyme fusion of trehalose-6-phosphate synthetase and trehalose-6-phosphate phosphatase of *Escherichia coli*." Appl Environ Microbiol, 66: 2484-2490.

118. Honjoh et al., 2009. "Enhancement of menadione stress tolerance in yeast by accumulation of hypotaurine and taurine: co-expression of cDNA clones, from *Cyprinus carpio*, for cysteine dioxygenase and cysteine sulfinate decarboxylase in *Saccharomyces cerevisiae*." Amino Acids, [Epub ahead of print].

119. Shahin 1985. "Totipotency of tomato protoplasts." Theor Appl Genet, 69: 235-240.

120. Fromm et al., 1985. "Expression of genes transferred into monocot and dicot plant cells by electroporation." Proc Natl Acad Sci USA, 82: 5824-5828.

121. Fromm et al., 1986. "Stable transformation of maize after gene transfer by electroporation." Nature, 319: 791-3.

122. Riggs et al., 1986. "Stable transformation of tobacco by electroporation: evidence for plasmid concatenation." Proc Natl Acad Sci USA, 83: 5602-5606.

123. D'Halluin et al., 1992. "Transgenic maize plants by tissue electroporation." Plant Cell, 4: 1495-1505.

124. Laursen et al., 1994. "Production of fertile transgenic maize by electroporation of suspension culture cells " Plant Mol Biol, 24: 51-61

125. Crossway et al., 1986. "Integration of foreign DNA following microinjection of tobacco mesophyll protoplasts." Mol Gen Genet, 202: 179-185.

126. Griesbach 1983. "Protoplast microinjection." Plant Mol Biol Report, 1: 32-37.

127. Sporlein et al., 1991. "Lipofectin: direct gene transfer to higher plants using cationic liposomes." Theor Appl Genet, 83: 1-5.

128. Ohgawara et al., 1983. "Uptake of liposome-encapsulated plasmid DNA by plant protoplasts and molecular fate of foreign DNA " Protoplasma, 116: 145-148.

129. Deshayes et al., 1985. "Liposome-mediated transformation of tobacco mesophyll protoplasts by an *Escherichia coli* plasmid." EMBO (Eur Mol Biol Organ) J, 4: 2731-7.

130. Christou et al., 1987. "Stable transformation of soybean by electroporation and root formation from transformed callus." Proc Natl Acad Sci USA, 84: 3962-3966.

131. Horsch et al., 1985. "A simple and general method for transferring genes into plants." Science, 227: 1229-1231.

132. Paszkowski et al., 1984. "Direct gene transfer to plants." Embo J, 3: 2717-2722.

133. Hooykaas-Van Slogteren et al., 1984. "Expression of Ti plasmid genes in monocotyledonous plants infected with *Agrobacterium tumefaciens*." Nature, 311: 763-764.

134. Rogers 1986. "Gene transfer in plants: Production of transformed plants using Ti-plasmid vectors." Methods Enzymol, 118: 627-640.

135. Bevan et al., 1982. "T-DNA of the *Agrobacterium* Ti and Ri plasmids." Annu Rev Genet, 16: 357-384.

136. Klein et al., 1988. "Transfer of foreign genes into intact maize cells with high-velocity microprojectiles." Proc Natl Acad Sci USA, 85: 4305-4309.

137. Klein et al., 1988. "Factors influencing gene delivery into *Zea mays* cells by high-velocity microprojectiles." Biotechnology, 6: 559-563.

138. McCabe et al., 1988. "Stable transformation of soybean (Glycine max) by particle acceleration." Biotechnology, 6: 923-926.

139. Sanford et al., 1993. Optimizing the biolistic process for different biological application. In Wu R, editor. The Methods in Enzymology 483-509. Orlando: Academic Press.

140. Freeman et al., 1984. "A comparison of methods for plasmid delivery into plant protoplasts." Plant Cell Physiol, 25: 1353-1365.

141. Frame et al., 1994. "Production of fertile transgenic maize plants by silicon carbide whisker-mediated transformation." Plant J, 6: 941-948.

142. Thompson et al., 1995. "Maize transformation utilizing silicon carbide whiskers: a review." Euphytica, 85: 75-80.

143. Guo et al., 1995. "Laser-mediated gene transfer in rice." Physiol Plant, 93: 19-24.

144. Badr et al., 2005. " Production of fertile transgenic wheat plants by laser micropuncture." Photochem Photobiol Sci, 4: 803-807.

145. Bao et al., 1997. " Transfection of a reporter plasmid into cultured cells by sonoporation in vitro." Ultrasound in Medicine and Biology, 23: 953-959.

146. Finer et al., 2000. "Use of *Agrobacterium* expressing green fluorescent protein to evaluate colonization of sonication-assisted *Agrobacterium*-mediated transformation-treated soybean cotyledons." Lett Appl Microbiol, 30: 406-10.

147. Amoah et al., 2001. "Factors influencing *Agrobacterium*-mediated transient expression of uidA in wheat inflorescence tissue." J Exp Bot, 52: 1135-42.

148. Krens et al., 1982. "In Vitro transformation of plant protoplasts with Ti-plasmid DNA." Nature, 296: 72-74.

149. Bechtold et al., 1998. "In planta *Agrobacterium*-mediated transformation of adult *Arabidopsis thaliana* plants by vacuum infiltration." Methods Mol Biol, 82: 259-66.

150. Broothaerts et al., 2005. "Gene transfer to plants by diverse species of bacteria." Nature, 433: 629-633.

151. Kirk et al., 1993. Concise Encyclopedia of Chemical Technology: John Wiley & Sons.

152. Mosbach et al., 1983. " Formation of proinsulin by immobilized *Bacillus subtilis*." Nature, 302: 543-545.

153. Chan et al., 1974. "Structural uniqueness of lactose operator." Nature, 252: 205-209.

154. Goeddel et al., 1980. "Synthesis of human fibroblast interferon by *E. coli*" Nucleic Acids Res, 8: 4057-4074.

155. Sherman et al., 1982. Methods in Yeast Genetics. New York: Cold Spring Harbor Laboratory.

156. Sherman 1991. Getting started with yeast. In Guthrie C & G R Fink, editors. Methods in Enzymology, Guide to Yeast Genetics and Molecular Biology 3-21. New York: Acad. Press.

157. Andersen et al., 1984. "Synthesis and anticonvulsant properties of some 2-Aminoethanesulfonic acid (Taurine) derivatives." J Pharm Sci, 73: 106-108.

158. Herdeis et al., 1999. U.S. Pat. No. 5,889,183.

159. Tserng et al., 1977. "An improved procedure for the synthesis of glycine and taurine conjugates of bile acids." J Lipid Res, 18: 404-407.

160. Fong et al., 1992. U.S. Pat. No. 5,128,419.

161. Seeberger et al., 2007. "A new strategy for the synthesis of taurine derivatives using the 'safety-catch' principle for the protection of sulfonic acids." Org Biomol Chem, 5: 132-138.

162. Suzuki et al., 2006. "Fabrication of TiO2 using L-lysine-based organogelators as organic templates: control of the nanostructures." Chem Commun 377-379.

163. Mikhalenko et al., 2004. "Phthalocyanines and related compounds: XXXVIII. Synthesis of symmetric taurine- and choline-substituted phthalocyanines." Russ J Gen Chem, 74: 1775-1800.

164. Capone et al., 2007. "Designing nanosensors based on charged derivatives of Gramicidin A." J Am Chem Soc, 129: 9737-9745.

165. Gupta et al., 2005. "Taurine analogues; A new class of therapeutics: Retrospect and prospects " Curr Med Chem, 12: 2021-2039.

166. Johnson 2008. "Update on neuropharmacological treatments for alcoholism: Scientific basis and clinical findings." Biochem Pharmacol, 75: 34-56.

167. Tambour et al., 2007. "Preclinical and clinical pharmacology of alcohol dependence." Fundam Clin Pharmacol, 21: 9-28.

168. Joung et al., 2005. "Anticoagulant supramolecular-structured polymers: Synthesis and anticoagulant activity of taurine-conjugated carboxyethylester-polyrotaxanes." Sci Technol Adv Mater, 6: 484-490.

169. Özmeriç et al., 2000. "Chitosan film enriched with an antioxidant agent, taurine, in fenestration defects." J Biomed Mater Res A, 51: 500-503.

170. Degim et al., 2002. "An investigation on skin wound healing in mice with a taurinechitosan gel formulation." Amino Acids, 22: 187-198.

171. Matsusaki et al., 2002. "Novel functional biodegradable polymer: Synthesis and anticoagulant activity of poly (γ-Glutamic Acid)sulfonate (γ-PGA-sulfonate)." Bioconjugate Chem, 13: 23-28.

172. Meinkoth et al., 1984. "Hybridization of nucleic acids immobilized on solid supports." Anal Biochem, 138: 267-284.

173. Tijssen 1993. Overview of principles of hybridization and the strategy of nucleic acid probe assays. Laboratory Techniques in Biochemistry and Molecular Biology—Hybridization with Nucleic Acid Probes: Part I. New York: Elsevier.

174. Smith et al., 1981. "Comparison of biosequences." Adv Appl Math, 2: 482-489.

175. Needleman et al., 1970. "A general method applicable to the search for similarities in the amino acid sequence of two proteins." J Mol Biol, 48: 443-453.

176. Pearson et al., 1988. "Improved tools for biological sequence comparison." Proc Natl Acad Sci USA, 85: 2444-2448.

177. Higgins et al., 1989. "Fast and sensitive multiple sequence alignments on a microcomputer." Comput Appl Biosci, 5: 151-153.

178. Higgins et al., 1988. "CLUSTAL: a package for performing multiple sequence alignment on a microcomputer." Gene, 73: 237-244.

179. Higgins et al., 1992. "CLUSTAL V: improved software for multiple sequence alignment." Comput Appl Biosci, 8: 189-191.

180. Feng et al., 1987. "Progressive sequence alignment as a prerequisite to correct phylogenetic trees." J Mol Evol, 25: 351-360.

181. Henikoff et al., 1989. "Amino acid substitution matrices from protein blocks" Proc Natl Acad Sci USA, 89: 10915-10919.

182. Altschul et al., 1997. "Gapped BLAST and PSI-BLAST: a new generation of protein database search programs." Nucleic Acids Res, 25: 3389-3402.

183. Wootton et al., 1993. "Statistics of local complexity in amino acid sequences and sequence databases." Comput Chem, 17: 149-163.

184. Wootton et al., 1996. "Analysis of compositionally biased regions in sequence databases." Methods Enzymol, 266: 554-571.

185. Claverie et al., 1993. "Information enhancement methods for large scale sequence analysis." Comput Chem, 17: 191-201.

186. Myers et al., 1988. "Optimal alignments in linear-space." Comput Appl Biol Sci, 4: 11-17.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Development of a Transgenic Plant that Constitutively Expresses COD Using Fusion PCR Step 1: Make a DNA construct that contains an AtTUB5 promoter with a CDO gene and a NOS terminator in the following manner.

Step 1a. Use PCR to amplify the AtTUB5 promoter (−1851 to −1 bps) with a short overlap for the 5' end of CDO at the 3' end of the promoter using 500 ng of genomic DNA isolated from an *Arabidopsis thaliana* Col-0. Add 300 nM of the following primers: 5'KpnTub5prom (5'-ttttggtacccacatttgcaaaatgatgaatg-3'; SEQ ID NO:27) and Tub5CDO (5'-catgacttcagtctgctccatccaatctggttaccgcattg-3'; SEQ ID NO:28). Run the fusion PCR as described by Szewczyk et al. (45).

Step 1b: Use PCR to amplify the CDO gene from 500 ng of cDNA from a zebrafish (*Danio rerio*) cDNA library. Add 300 nM of the following primers: 5'CDO (5'-atggagcagactgaagtcatg-3'; SEQ ID NO:29) and 3'CDO (5'-tcagttattctcctgcgagac-3'; SEQ ID NO:30). Run the fusion PCR as described by Szewczyk et al. (45).

Step 1c: Use PCR to amplify the NOS terminator with a short overlap for the 3' end of CDO at the 5' end of the terminator using 500 ng of pPV1. Add 300 nM of the following primers CDONOS (5'-gtctcgcaggagaataactgagctaccgagctcgaatttcc-3'; SEQ ID NO:31) and 3'NOS (5'-cacgacgttgtaaaacgacggc-3'; SEQ ID NO:32). Run the fusion PCR as described by Szewczyk et al. (45).

Step 1d: Combine the amplified fragments from Example 3: steps 1a, 1b, and 1c and 300 nM of the following primers GP2 (5'-ttttggtaccgtttacatatggagatgatgtc-3'; SEQ ID NO:33) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli,* select for antibiotic resistance, conduct PCR identification of cloned DNA constructs in transformants, purify DNA and sequence. Digest the plasmid with Acc65I and XbaI, isolate DNA fragment and ligate into the vector pCAMBIA2300 that has been predigested with Acc65I and XbaI.

Step 1f. Transform the ligated vector containing the DNA construct by electroporation into *E. coli.* Select for kanamycin (50 μg/ml) resistance on LB plates. Confirm the presence of the DNA constructs in the selected colonies by PCR analysis with the GP2 and GP5 primers using the following program: 96° C. for 3 min followed by 25 cycles of 94° C. for 30 seconds, 55° C. for 30 seconds, 72° C. for 5 min, and 72° C. for 3 min. Grow a colony that contains the proper DNA construct overnight at 37° C. in 6 ml LB plus spectinomycin (100 μg/ml) or streptomycin (200 μg/ml). Isolate the plasmid DNA that contains the DNA construct by Wizard Plus SV Minipreps DNA Purification System (Promega Corporation, Madison, Wis., USA). Sequence the DNA insert to confirm its identity and the fidelity of the DNA construct.

Step 2: Transform *Agrobacterium tumefaciens*

Independently transform the vector construct into electrocompetent *Agrobacterium tumefaciens* EHA105, as described by the Green Lab Protocol (http://www.bch.msu.edu/pamgreen/green.htm). Select positive transformants using Terrific Broth plus kanamycin (50 μg/ml) on 1% agar plates. Confirm *Agrobacterium* colonies by PCR using the following primers: GP2 and GP5. Run the following PCR reaction: 96° C. for 5 min followed by 20 cycles of 94° C. for 45 seconds, 60° C. for 30 seconds, 70° C. for 5 min, and 72° C. for 3 min.

Step 3: Transform Plant, *Arabidopsis thaliana*

Step 3a: Sow *Arabidopsis* (L.) Heynh. ecotype Columbia (Col-0) seeds in 248 $cm^2$ plastic pots with moistened soil (Promix HP, Premier Horticulture Inc., Redhill, Pa., Canada). Grow plants at 20-21° C., with 60-70% relative humidity, under cool white fluorescent lights (140 $\mu mol^{-2}s^{-1}$) with a 16 h light/8 h dark cycle. Water plants as needed by subirrigation. After two weeks, transfer five individual plants to smaller pots (72 $cm^2$) for use in the transformation protocol. Grow the plants until the first floral buds and flowers form (2-3 additional weeks).

Step 3b: Grow *Agrobacterium,* the construct to be transformed, in 500 ml of Terrific Broth plus kanamycin (50 μg/ml) for 2 days at 29° C. Collect cells by centrifugation at 6000 rpm for 15 minutes, and resuspend cells in 5% sucrose plus 0.05% surfactant (Silwet L-77, Lehle Seeds, Round Rock, Tex., USA) solution.

Step 3c: Transform plants by the floral dip transformation (144). Keep the plants in sealed containers to maintain high humidity for 16 to 24 h and maintain plants as described in step 4a above. At 8 to 10 weeks, dry the plants, collect the seeds, and select for the marker in each line. Select for kanamycin resistance for the AtTUB5::CDO constructs in pCAMBIA2300 by incubating seeds on plates containing 4.418 g/L Murashige and Skoog Salt and Vitamin Mixture (MS medium, Life Technologies, Grand Island, N.Y., USA) plus kanamycin (50 μg/ml) and 0.8% (wt vol) Phytagar. Collect and transfer positively selected plants into pots containing soil and grow for 5 to 6 weeks. Allow the plants to self-pollinate. Collect the seeds and repeat the selection process until homozygotes are identified.

EXAMPLE 2

Development of a Transgenic Plant that Constitutively Expresses (AtPHYB promoter) CDO and SAD Using Fusion PCR Step 1: Make a DNA construct that contains an AtPHYB (Locus ID#At2g18790) promoter with a CDO gene and a NOS terminator in the following manner.

Step 1a: Use PCR to amplify the AtPHYB promoter (−1960 to −1 bps) with a short overlap for the 5' end of CDO at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBCDO (5'-catgacttcagtctgctccatgccgtttgattttgaatttgag-3'; SEQ ID NO:36). Run the fusion PCR as described by Szewczyk et al. (45).

Step 1b: Use the CDO gene that was amplified in Example 1: Step 1b.

Step 1c: Use the NOS terminator with a short overlap for the 3' end of CDO at the 5' end of the NOS terminator that was amplified in Example 1: Step 1c.

Step 1d: Combine the PCR fragments (Example 2: 1a, 1b, and 1c) and 300 nM of the following primers HP2 (5'-ttttcccgggattcttgaattacgattgtacc-3'; SEQ ID NO:37) and GP5 (5'-tttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1e. Transform *E. coli,* select for antibiotic resistance, conduct PCR identification of cloned DNA constructs in transformants, purify DNA and sequence (described in Example 1: step 1e). Digest the plasmid with XmaI and XbaI, isolate DNA fragment and ligate into the vector pCAMBIA2300 that has been predigested with XmaI and XbaI.

Step 2: Make a DNA construct that contains an AtPHYB promoter with a SAD gene and a NOS terminator to in the following manner.

Step 2a: Use PCR to amplify the AtPHYB promoter (−1960 to −1 bps) with a short overlap for the 5' end of SAD at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBSAD (5'-cagcttcccatcagactcgtccatgc-cgtttgattttgaatttgag-3'; SEQ ID NO:38). Run the fusion PCR as described by Szewczyk et al. (45).

Step 2b: Use PCR to amplify the SAD gene from 500 ng of cDNA from a zebrafish (*Danio rerio*) cDNA library. Add 300 nM of the following primers: 5'SAD (5'-atggacgagtct-gatgggaagctg-3'; SEQ ID NO:39) and 3'SAD (5'-tcatagatc-cttcccgagtttc-3'; SEQ ID NO:40). Run the fusion PCR as described by Szewczyk et al. (45).

Step 2c: Use PCR to amplify the NOS terminator with a short overlap for the 3' end of SAD at the 5' end of the terminator using 500 ng of pPV1. Add 300 nM of the following primers SADNOS (5'-gaaactcgggaaggatctatgagc-taccgagctcgaatttcc-3'; SEQ ID NO:41) and 3'NOS (5'-cac-gacgttgtaaaacgacggc-3'; SEQ ID NO:32). Run the fusion PCR as described by Szewczyk et al. (45).

Step 2d: Combine the PCR fragments (Example 2: 2a, 2b, and 2c) and 300 nM of the following primers IP2 (5'-aaaaatctagaattcttgaattacgattgtac-3'; SEQ ID NO:42) and IP5 (5'-tttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 2e: Transform *E. coli,* select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and SalI, isolate DNA fragment and ligate into the vector pCAMBIA2300 that has been predigested with XbaI and SalI.

Step 3: Ligate the AtPHYB promoter-CDO-NOS terminator construct upstream of the AtPHYB promoter-SAD-NOS terminator construct into a plant expression vector.

Step 3a. Digest the pCambia2300-AtPHYB promoter-CDO-NOS terminator clone (from Example 4: Step 1e) with XmaI and XbaI, isolate DNA insert and ligate it into the vector pCambia2300-AtPHYB promoter-SAD-NOS terminator (from Example 4: Step 2e) that has been predigested with XmaI and XbaI. Transform the DNA construct into *E. coli,* select for antibiotic resistance and confirm the presence of the DNA construct with PCR or by restriction digest analysis.

Step 4: Transform *Agrobacterium tumefaciens:* Transform the DNA construct into *Agrobacterium tumefaciens,* select for antibiotic resistance and confirm the presence of the DNA construct as described in Example 1: Step 2.

Step 5: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 3

Development of a Transgenic Plant that Constitutively Expresses (AtPHYB promoter) CDO and GAD using Fusion PCR Step 1: Make a DNA construct that contains an AtPHYB (Locus ID#At2g18790) promoter with a CDO gene and a NOS terminator in the following manner.

Step 1a: Use the AtPHYB promoter with a short overlap for the 5' end of CDO at the 3' end that was amplified in Example 2: Step 1a Step 1b: Use the CDO gene that was amplified in Example 1: Step 1b.

Step 1c: Use the NOS terminator with a short overlap for the 3' end of CDO at the 5' end of the NOS terminator that was amplified in Example 1: Step 1c.

Step 1d: Combine the PCR fragments (Example 3: 1a, 1b, and 1c), run the PCR and the clone the amplified fragment as described in Example 2: Step 1d.

Step 1e. Transform *E. coli,* select for antibiotic resistance, conduct PCR identification of cloned DNA constructs in transformants, purify DNA and sequence (described in Example 1: step 1e). Digest the plasmid with XmaI and XbaI, isolate DNA fragment and ligate into the vector pCAMBIA2300 that has been predigested with XmaI and XbaI.

Step 2: Make a DNA construct that contains an AtPHYB promoter with a GAD gene and a NOS terminator to in the following manner.

Step 2a: Use PCR to amplify the AtPHYB promoter (−1960 to −1 bps) with a short overlap for the 5' end of GAD at the 3' end using 500 ng of genomic DNA isolated from an *Arabidopsis thaliana* Col-0. Add 300 nM of the following primers: 5'AtPHYB (5'-caatgcctaataatgtctagc-3'; SEQ ID NO:35) and AtPHYBGAD (5'-cgttacttgcttcttatccatgccgttt-gattttgaatttgag-3'; SEQ ID NO:44). Run the fusion PCR as described by Szewczyk et al. (45).

Step 2b: Use PCR to amplify the GAD gene from 500 ng of DNA from *E. coli* strain K12. Add 300 nM of the following primers: 5'GAD (5'-atggataagaagcaagtaacg-3'; SEQ ID NO:45) and 3'GAD (5'-tcaggtatgtttaaagctgttc-3'; SEQ ID NO:46). Run the fusion PCR as described by Szewczyk et al. (45).

Step 2c: Use PCR to amplify the NOS terminator with a short overlap for the 3' end of GAD at the 5' end of the terminator using 500 ng of pPV1. Add 300 nM of the following primers GADNOS (5'-gaacagctttaaacatacctgagc-taccgagctcgaatttcc-3'; SEQ ID NO:47) and 3'NOS (5'-cac-gacgttgtaaaacgacggc-3'; SEQ ID NO:32). Run the fusion PCR as described by Szewczyk et al. (45).

Step 2d: Combine the PCR fragments (Example 3: 2a, 2b, and 2c) and 300 nM of the following primers IP2 (5'-aaaaatctagaattcttgaattacgattgtacc-3'; SEQ ID NO:42) and IP5 (5'-tttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 2e: Transform *E. coli,* select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and SalI, isolate DNA fragment and ligate into the vector pCAMBIA2300 that has been predigested with XbaI and SalI.

Step 3: Ligate the AtPHYB promoter-CDO-NOS terminator construct upstream of the AtPHYB promoter-GAD-NOS terminator construct into a plant expression vector.

Step 3a. Digest the pCambia2300-AtPHYB promoter-CDO-NOS terminator clone (from Example 4: Step 1e) with XmaI and XbaI, isolate DNA insert and ligate it into the vector pCambia2300-AtPHYB promoter-GAD-NOS terminator (from Example 4: Step 2e) that has been predigested with XmaI and XbaI. Transform the DNA construct into *E. coli,* select for antibiotic resistance and confirm the presence of the DNA construct with PCR or by restriction digest analysis.

Step 4: Transform *Agrobacterium tumefaciens:* Transform the DNA construct into *Agrobacterium tumefaciens,* select for antibiotic resistance and confirm the presence of the DNA construct as described in Example 1: Step 2.

Step 5: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 4

Development of a Transgenic Plant that Non-Constitutively Expresses (AtGAD1 Promoter) ADO using Fusion PCR Step 1: Make a DNA construct that contains an AtGAD1 (Locus ID#At5g17330) promoter with an ADO gene and a NOS terminator in the following manner.

Step 1a: Use PCR to amplify the AtGAD1 promoter (−1732 to −1 bps) with a short overlap for the 5' end of ADO at the 3' end of the promoter using 500 ng of genomic DNA isolated from an *Arabidopsis thaliana* Col-0. Add 300 nM of the following primers: 5'AtGAD1 (5'-accaaaggataccctgatttg-3'; SEQ ID NO:48) and AtGAD1ADO (5'-gattttctggactgtggaagtcatcacggagatgagagagagag-3'; SEQ ID NO:49). Run the fusion PCR as described by Szewczyk et al. (45).

Step 1b: Use PCR to amplify the ADO gene from 500 ng of cDNA from a zebrafish (*Danio rerio*) cDNA library. Add 300 nM of the following primers: 5'ADO (5'-atgacttccacagtccagaaaatc-3'; SEQ ID NO:50) and 3'ADO (5'-tcagagggtcactttaggc-3'; SEQ ID NO:51). Run the fusion PCR as described by Szewczyk et al. (45).

Step 1c: Use PCR to amplify the NOS terminator with a short overlap for the 3' end of ADO at the 5' end of the terminator using 500 ng of pPV 1. Add 300 nM of the following primers ADONOS (5'-gcctaaagtgaccctctgagctaccgagctcgaatttcc-3'; SEQ ID NO:52) and 3'NOS (5'-cacgacgttgtaaaacgacggc-3'; SEQ ID NO:32). Run the fusion PCR as described by Szewczyk et al. (45).

Step 1d: Combine the amplified fragments (Example 4: steps 1a, 1b, and 1c) and 300 nM of the following primers JP2 (5'-aaaaaggtaccgatatttgagcaaaactgtgg-3'; SEQ ID NO:30) and GP5 (5'-tttttttTCTAGAgatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 5

Development of a Transgenic Plant that Non-Constitutively Expresses (AtGAD2 Promoter) TPAT using Fusion PCR Step 1: Make a DNA construct that contains an AtGAD2 (Locus ID#At1g65960) promoter with a TPAT gene and a NOS terminator in the following manner.

Step 1a: Use PCR to amplify the AtGAD2 promoter (−1714 to −1 bps) with a short overlap for the 5' end of TPAT at the 3' end using 500 ng of genomic DNA isolated from an *Arabidopsis thaliana* Col-0. Add 300 nM of the following primers: 5'AtGAD2 (5'-tcttaccttgtcctgcaacgag-3'; SEQ ID NO:54) and AtGAD2TPAT (5'-cattgaaattgccgtccatctttgtttctgtttagtgaaag-3'; SEQ ID NO:55). Run the fusion PCR as described by Szewczyk et al. (45).

Step 1b: Use PCR to amplify the TPAT gene from 500 ng of DNA from *Roseobacter denitrificans* strain. Add 300 nM of the following primers: 5'TPAT (5'-atggacggcaatttcaatg-3'; SEQ ID NO:56) and 3'TPAT (5'-ttagccgaaaacgcgcgacag-3'; SEQ ID NO:57). Run the fusion PCR as described by Szewczyk et al. (45).

Step 1c: Use PCR to amplify the NOS terminator with a short overlap for the 3' end of TPAT at the 5' end of the terminator using 500 ng of pPV1. Add 300 nM of the following primers TPATNOS (5'-ctgtcgcgcgttttcggctaagctaccgagctcgaatttcc-3'; SEQ ID NO:58) and 3'NOS (5'-cacgacgttgtaaaacgacggc-3'; SEQ ID NO:32). Run the fusion PCR as described by Szewczyk et al. (45).

Step 1d: Combine the amplified fragments (Example 5: steps 1a, 1b, and 1c) and 300 nM of the following primers KP2 (5'-ttttggtaccctctttcggaacgagcttcaac-3'; SEQ ID NO:59) and GP5 (5'-ttttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 6

Development of a Transgenic Plant that Non-Constitutively Expresses (AtGAD2 Promoter) TPAT and SA using Fusion PCR Step 1: Make a DNA construct that contains an AtGAD2 (Locus ID#) promoter with a TPAT gene and a NOS terminator in the following manner.

Step 1a: Use the AtGAD2 promoter that was amplified in Example 5: Step 1b

Step 1b: Use the TPAT gene that was amplified in Example 5: Step 1b.

Step 1c: Use the NOS terminator with a short overlap for the 3' end of TPAT at the 5' end of the NOS terminator that was amplified in Example 5: Step 1c.

Step 1d: Combine the PCR fragments (Example 5: 1a, 1b, and 1c), run the PCR and the clone the amplified fragment as described in Example 5: Step 1d.

Step 1e. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2: Make a DNA construct that contains an AtGAD2 promoter with a SA gene and a NOS terminator to in the following manner.

Step 2a: Use PCR to amplify the AtGAD2 promoter (−1960 to −1 bps) with a short overlap for the 5' end of SA at the 3' end using 500 ng of genomic DNA isolated from an *Arabidopsis thaliana* Col-0. Add 300 nM of the following primers: 5'AtGAD2 (5'-cttaccttgtcctgcaacgag-3'; SEQ ID NO:54) and AtGAD2SA (5'-cttcagtggtcattttcatctttgtttctgtttagtgaaag-3'; SEQ ID NO:60). Run the fusion PCR as described by Szewczyk et al. (45).

Step 2b: Use PCR to amplify the SA gene from 500 ng of DNA from *Roseobacter denitrificans.* Add 300 nM of the following primers: 5'SA (5'-atgaaaatgaccactgaag-3'; SEQ ID NO:61) and 3'SA (5'-tcagacagtctgtggacgc-3'; SEQ ID NO:62). Run the fusion PCR as described by Szewczyk et al. (45).

Step 2c: Use PCR to amplify the NOS terminator with a short overlap for the 3' end of SA at the 5' end of the terminator using 500 ng of pPV1. Add 300 nM of the following primers SANOS (5'-gcgtccacagactgtctgagctaccgagctcgaatttcc-3'; SEQ ID NO:63) and 3'NOS ; 5'-caccgacgttgtaaaacgacggc-3' SEQ ID NO:32). Run the fusion PCR as described by Szewczyk et al. (45).

Step 2d: Combine the PCR fragments (Example 6: 2a, 2b, and 2c) and 300 nM of the following primers LP2 (5'-tttttctagagaacgagcttcaacgtagcc-3'; SEQ ID NO:64) and LP5 (5'-aaaaaaagcttgatctagtaacatagatgacac-3'; SEQ ID NO:65). Run the fusion PCR as described by Szewczyk et al. (45). Clone into pCR4.0-TOPO as described by the manufacturer (Invitrogen).

Step 2e: Transform *E. coli,* select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and HindIII, isolate DNA fragment and ligate into the vector pCAMBIA2300 that has been predigested with XbaI and HindIII.

Step 3: Ligate the AtGAD2 promoter-TPAT-NOS terminator construct upstream of the AtGAD2 promoter-SA-NOS terminator construct into a plant expression vector.

Step 3a. Digest the pCambia2300-AtGAD2 promoter-TPAT-NOS terminator clone (from Example 4: Step 1e) with Acc65I and XbaI, isolate DNA insert and ligate it into the vector pCambia2300-AtGAD2 promoter-SA-NOS terminator (from Example 6: Step 2e) that has been predigested with Acc65I and XbaI. Transform the DNA construct into *E. coli,* select for antibiotic resistance and confirm the presence of the DNA construct with PCR or by restriction digest analysis.

Step 4: Transform *Agrobacterium tumefaciens:* Transform the DNA construct into *Agrobacterium tumefaciens,* select for antibiotic resistance and confirm the presence of the DNA construct as described in Example 1: Step 2.

Step 5: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 7

Development of a Transgenic Plant that that Non-Constitutively Expresses (AtGLR1.1 Promoter) ssTDeHase and lsTDeHase using Fusion PCR Step 1: Make a DNA construct that contains an AtGLR1.1 (Locus ID #At3g04110) promoter with a ssTDeHase gene and a NOS terminator in the following manner.

Step 1a: Use PCR to amplify the glutamate receptor 1.1 promoter (−1400 to −1 bps) with a short overlap for the 5' end of ssTDeHase at the 3' end using 500 ng of genomic DNA isolated from an *Arabidopsis thaliana* Col-0. Add 300 nM of the following primers: 5'AtGLR1.1 (5'-gatcatacatattcatacttgatg-3'; SEQ ID NO:66) and AtGLR1.1ssTDeHase (5'-gagctgtcagtgttttggtcatataatttcttgtatagctctgtaac-3'; SEQ ID NO:67). Run the fusion PCR as described by Szewczyk et al. (45).

Step 1b: Use PCR to amplify the ssTDeHase gene from 500 ng of DNA from *Roseobacter denitrificans.* Add 300 nM of the following primers: 5'ssTDeHase (5'-atgaccaaaacactgacagctc-3'; SEQ ID NO:68) and 3'ssTDeHase (5'-ttaagccttgaagggcgggc-3'; SEQ ID NO:69). Run the fusion PCR as described by Szewczyk et al. (45).

Step 1c: Use PCR to amplify the NOS terminator with a short overlap for the 3' end of ssTDeHase at the 5' end of the terminator using 500 ng of pPV1. Add 300 nM of the following primers ssTDeHaseNOS (5'-gcccgcccttcaaggcttaagctaccgagctcgaatttcc-3'; SEQ ID NO:70) and 3'NOS (5'- cacgacgttgtaaaacgacggc-3'; SEQ ID NO:32). Run the fusion PCR as described by Szewczyk et al. (45).

Step 1d: Combine the PCR fragments (Example 7: 1a, 1b, and 1c) and 300 nM of the following primers MP2 (5'-ttttggtacccgaagctcaatcgtctcgag-3'; SEQ ID NO:71) and GP5 (5'-tttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1e. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI Step 2: Make a DNA construct that contains an AtGLR1.1 promoter with a lsTDeHase gene and a NOS terminator to in the following manner.

Step 2a: Use PCR to amplify the AtGLR1.1 promoter (−1714 to −1 bps) with a short overlap for the 5' end of lsTDeHase at the 3' end of the promoter using 500 ng of genomic DNA isolated from an *Arabidopsis thaliana* Col-0. Add 300 nM of the following primers: 5'AtGLR1.1 (5'-gatcatacatattcatacttgatg-3'; SEQ ID NO:66) and AtGLR1.1-lsTDeHase (5'-gtgctttggtctatgtggcatataatttcttgtatagctctgtaac-3'; SEQ ID NO:72). Run the fusion PCR as described by Szewczyk et al. (45).

Step 2b: Use PCR to amplify the lsTDeHase gene from 500 ng of DNA from *Roseobacter denitrificans*. Add 300 nM of the following primers: 5'lsTDeHase (5'-atgccacatagaccaaagcac-3'; SEQ ID NO:73) and 3'lsTDeHase (5'-tcagagaatttcatcgcgaag-3'; SEQ ID NO:74). Run the fusion PCR as described by Szewczyk et al. (45).

Step 2c: Use PCR to amplify the NOS terminator with a short overlap for the 3' end of lsTDeHase at the 5' end of the terminator using 500 ng of pPV1. Add 300 nM of the following primers lsTDeHaseNOS (5'-cttcgcgatgaaattctctgagctaccgagctcgaatttcc-3'; SEQ ID NO:75) and 3'NOS (5'-cacgacgttgtaaaacgacggc-3'; SEQ ID NO:32). Run the fusion PCR as described by Szewczyk et al. (45).

Step 2d: Combine the PCR fragments (Example 7: 2a, 2b, and 2c) and 300 nM of the following primers NP2 (5'-aaaaatctagacgaagctcaatcgtctcgag-3'; SEQ ID NO:76) and LP5 (5'-aaaaaaagcttgatctagtaacatagatgacac-3'; SEQ ID NO:65). Run the fusion PCR as described by Szewczyk et al. (45). Clone into pCR4.0-TOPO as described by the manufacturer (Invitrogen).

Step 2e: Transform *E. coli,* select for antibiotic resistance, conduct PCR identification of cloned DNA constructs in transformants, purify the plasmid that contains the DNA construct to confirm its identity and the fidelity of the sequence as described in Example 1: step 1e.purify. Digest the plasmid with XbaI and HindIII, isolate the DNA fragment and ligate into the vector pCAMBIA2300 that has been predigested with XbaI and HindIII.

Step 3: Ligate the AtGLR1.1 promoter-ssTDeHase-NOS terminator construct upstream of the AtGLR1.1 promoter-lsTDeHase-NOS terminator construct into a plant expression vector.

Step 3a. Digest the pCambia2300-AtGLR1.1 promoter-ssTDeHase-NOS terminator clone (from Example 4: Step 1e) with Acc65I and XbaI, isolate DNA insert and ligate it into the vector pCambia2300-AtGLR1.1 promoter-lsTDeHase-NOS terminator (from Example 4: Step 2e) that has been predigested with Acc65I and XbaI. Transform the DNA construct into *E. coli,* select for antibiotic resistance and confirm the presence of the DNA construct with PCR or by restriction digest analysis.

Step 4: Transform *Agrobacterium tumefaciens:* Transform the DNA construct into *Agrobacterium tumefaciens,* select for antibiotic resistance and confirm the presence of the DNA construct as described in Example 1: Step 2.

Step 5: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 8

Development of a Transgenic Plant that Non-Constitutively Expresses (AtSULTR1;3 Promoter) TDO using Fusion PCR Step 1: Make a DNA construct that contains an 5'AtSULTR1;3 promoter with a TDO gene and a NOS terminator in the following manner.

Step 1a: Use PCR to amplify the AtSULTR1;3 promoter (−2406 to −1 bps) with a short overlap for the 5' end of TDO at the 3' end using 500 ng of genomic DNA isolated from an *Arabidopsis thaliana* Col-0. Add 300 nM of the following primers: 5'AtSULTR1;3 (5'-tcacaatcgatggactctc-3'; SEQ ID NO:77) and 5'AtSULTR1;3 TDO (5'-gtaatgctcagacgttcactcattgctatgtgtgttttgtagc-3'; SEQ ID NO:78). Run the fusion PCR as described by Szewczyk et al. (45).

Step 1b: Use PCR to amplify the TDO gene from 500 ng of DNA from *E. coli* strain K12. Add 300 nM of the following primers: 5'TDO (5'-atgagtgaacgtctgagcattac-3'; SEQ ID NO:79) and 3'TDO (5'-ttaccccgccccgataaaacg-3'; SEQ ID NO:80). Run the fusion PCR as described by Szewczyk et al. (45).

Step 1c: Use PCR to amplify the NOS terminator with a short overlap for the 3' end of ADO at the 5' end of the terminator using 500 ng of pPV1. Add 300 nM of the following primers TDONOS (5'-cgttttatcgggcggggtaagctaccgagctcgaatttcc-3'; SEQ ID NO:81) and 3'NOS (5'-cacgacgttgtaaaacgacggc-3'; SEQ ID NO:32). Run the fusion PCR as described by Szewczyk et al. (45).

Step 1d: Combine the amplified fragments from Example 3: steps 1a, 1b, and 1c and 300 nM of the following primers OP2 (5'-ttttggtaccctatattggtgtcattttgcc-3'; SEQ ID NO:82) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1e. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 9

Development of a Transgenic Plant that Constitutively Expresses (AtPHYB Promoter) CDO Fused in Frame with SAD (without a Linker) using Fusion PCR Step 1: Make a DNA construct that contains an AtPHYB (Locus ID#At2g18790) promoter with a CDO gene fused in-frame with a SAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the SAD gene with a short overlap for the 3' end of CDO at the 5' end using 500 ng of cDNA from a zebrafish (*Danio rerio*) cDNA library. Add 300 nM of the following primers: CDO/SAD

```
(5'-gagcgtctcgcaggagaataacatggacgagtctgatgggaagctg
-3'; SEQ ID NO: 83)
and

3'SAD
(5'-tcatagatccttcccgagtttc-3'; SEQ ID NO: 40).
```

Run the fusion PCR as described by Szewczyk et al. (45).

Step 1d: Use the NOS terminator with a short overlap for the 3' end of SAD at the 5' end of the NOS terminator that was amplified in Example 2: Step 2c.

Step 1e: Combine the PCR fragments (Example 9: 1a, 1b, 1c, and 1d) and 300 nM of the following primers HP2 (5'-ttttcccgggattcttgaattacgattgtacc-3'; SEQ ID NO:37) and IP5 (5'-ttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 10

Development of a Transgenic Plant that Constitutively Expresses (AtPHYB Promoter) CDO Fused in Frame with a Linker to SAD Using Fusion PCR Step 1: Make a DNA construct that contains an AtPHYB (Locus ID#At2g18790) promoter with a CDO gene fused in-frame with a linker and the SAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the SAD gene with a short overlap for the 3' end of CDO at the 5' end using 500 ng of cDNA from a zebrafish (*Danio rerio*) cDNA library. Add 300 nM of the following primers: CDOlinkerSAD (5'-_gagcgtctcgcaggagaataacagtactgaaggcgaagtta acgcg-gaagaagaaggctttatggacgagtctgatgggaagctg-3'; SEQ ID NO:84) and 3'SAD (5'-tcatagatccttcccgagtttc-3'; SEQ ID NO:40). Run the fusion PCR as described by Szewczyk et al. (45).

Step 1d: Use the NOS terminator with a short overlap for the 3' end of SAD at the 5' end of the NOS terminator that was amplified in Example 2: Step 2c.

Step 1e: Combine the PCR fragments (Example 10: 1a, 1b, 1c, and 1d) and 300 nM of the following primers HP2 (5'-ttttcccgggattcttgaattacgattgtacc-3'; SEQ ID NO:37) and IP5 (5'-ttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 11

Development of a Transgenic Plant that Constitutively Expresses (AtPHYB Promoter) SAD Fused in Frame with CDO with Linker Using Fusion PCR Step 1: Make a DNA construct that contains an AtPHYB (Locus ID#At2g18790) promoter with a SAD gene fused in-frame with a CDO gene with a linker and a NOS terminator in the following manner.

Step 1a: Use the AtPHYB promoter (−1960 to −1 bps) with a short overlap for the 5' end of SAD at the 3' end that was amplified in Example 2: Step 2a.

Step 1b: Step Use the SAD gene that was amplified in Example 2: Step 2b.

Step 1c: Use PCR to amplify the CDO gene with a linker and short overlap for the SAD at the 3' using 500 ng of cDNA from a zebrafish (*Danio rerio*) cDNA library. Add 300 nM of the following primers: SADlinkerCDO (5'-gaaactcgggaaggatctaagtactgaaggcgaagttaacgcggaag aagaaggctttatggagcagactgaagtcatg-3'; SEQ ID NO:85 and 3'CDO (5'-tcagttattctcctgcgagac-3'; SEQ ID NO:30). Run the fusion PCR as described by Szewczyk et al. (45).

Step 1d: Use the NOS terminator with a short overlap for the 3' end of CDO at the 5' end of the NOS terminator that was amplified in Example 1: Step 1c.

Step 1e: Combine the PCR fragments (Example 11: 1a, 1b, 1c, and 1d) and 300 nM of the following primers HP2 (5'-ttttcccgggattcttgaattacgattgtacc-3'; SEQ ID NO:37) and GP5 (5'-tttttttctagagatctagtaacatagatgacac-3'; SEQ ID NO:34). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and XbaI, isolate DNA fragment and ligate into the vector pCAMBIA2300 that has been predigested with XmaI and XbaI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 12

Development of a Transgenic Plant that Constitutively Expresses (AtPHYB Promoter) CDO Fused in Frame with GAD (without a Linker) Using Fusion PCR Step 1: Make a DNA construct that contains an AtPHYB (Locus ID#At2g18790) promoter with a CDO gene fused in-frame with a GAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the GAD gene with a short overlap for the 3' end of CDO at the 5' end using from 500 ng of DNA from *E. coli* strain K12. Add 300 nM of the following primers: CDO/GAD (5'-gagcgtctcgcaggagaataacAtggataagaagcaagtaacg-3'; SEQ ID NO:86) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of GAD at the 5' end of the NOS terminator that was amplified in Example 3: Step 2c.

Step 1e: Combine the PCR fragments (Example 12: 1a, 1b, 1c, and 1d) and 300 nM of the following primers HP2 (5'-ttttcccgggattcttgaattacgattgtacc-3'; SEQ ID NO:37) and IP5 (5'-ttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 13

Development of a Transgenic Plant that Constitutively Expresses (AtPHYB Promoter) CDO Fused in Frame with a Linker to GAD using Fusion PCR Step 1: Make a DNA construct that contains an AtPHYB (Locus ID#At2g18790) promoter with a CDO gene fused in-frame with a linker and the GAD gene and a NOS terminator in the following manner.

Step 1a: Use the AtPHYB promoter (−1960 to −1 bps) with a short overlap for the 5' end of CDO at the 3' end that was amplified in Example 2: Step 1a.

Step 1b: Use the CDO gene that was amplified in Example 1: Step 1b.

Step 1c: Use PCR to amplify the GAD gene with a short overlap for the 3' end of CDO at the 5' end using 500 ng of DNA from *E. coli* strain K12. Add 300 nM of the following primers: CDOlinkerGAD (5'-gagcgtctcgcaggagaataacagtactgaaggcgaagttaacgcggaagaagaaggcttt atggataagaagcaagtaacg-3'; SEQ ID NO:87) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of GAD at the 5' end of the NOS terminator that was amplified in Example 3: Step 2c.

Step 1e: Combine the PCR fragments (Example 13: 1a, 1b, 1c, and 1d) and 300 nM of the following primers HP2 (5'-ttttcccgggattcttgaattacgattgtacc-3'; SEQ ID NO:37) and IP5 (5'-ttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 14

Development of a Transgenic Plant that Constitutively Expresses (AtPHYB Promoter) GAD Fused in Frame with a Pinker to CDO Using Fusion PCR Step 1: Make a DNA construct that contains an AtPHYB (Locus ID#At2g18790) promoter with a GAD gene fused in-frame with a linker and the CDO gene and a NOS terminator in the following manner.

Step 1a: Use the AtPHYB promoter (−1960 to −1 bps) with a short overlap for the 5' end of GAD at the 3' end that was amplified in Example 3: Step 2a.

Step 1b: Step Use the GAD gene that was amplified in Example 3: Step 2b.

Step 1c: Use PCR to amplify the GAD gene with a linker and short overlap for the CDO at the 3' using 500 ng of cDNA from a zebrafish (*Danio rerio*) cDNA library. Add 300 nM of the following primers: GADlinkerCDO (5'-gaacagctttaaacataccagtactgaaggcgaagttaacgcg-gaagaagaaggctttatggagcagactgaagtcatg-3'; SEQ ID NO:88) and 3'GAD (5'-tcaggtatgtttaaagctgttc-3'; SEQ ID NO:46). Run the fusion PCR as described by Szewczyk et al. (45).

Step 1d: Use the NOS terminator with a short overlap for the 3' end of CDO at the 5' end of the NOS terminator that was amplified in Example 1: Step 1c.

Step 1e: Combine the PCR fragments (Example 14: 1a, 1b, 1c, and 1d) and 300 nM of the following primers HP2 (5'-ttttcccgggattcttgaattacgattgtacc-3'; SEQ ID NO:37) and IP5 (5'-tttttttgtcgacgatctagtaacatagatgacac-3'; SEQ ID NO:43). Run the fusion PCR as described by Szewczyk et al. (45). Clone into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with XmaI and SalI, isolate DNA fragment and ligate into the vector pCAMBIA2300 that has been predigested with XmaI and SalI. Transform the DNA construct into *E. coli,* select for antibiotic resistance and confirm the presence of the DNA construct with PCR or by restriction digest analysis.

Step 2: Transform *Agrobacterium tumefaciens:* Transform the DNA construct into *Agrobacterium tumefaciens,* select for antibiotic resistance and confirm the presence of the DNA construct as described in Example 1: Step 2.

Step 3: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 15

Development of a transgenic plant that non-constitutively expresses (AtGAD2 promoter) SA fused in frame to TPAT using fusion PCR Step 1: Make a DNA construct that contains an AtGAD2 (Locus ID#At1g65960) promoter with a SA gene fused in-frame with a TPAT gene and a NOS terminator in the following manner.

Step 1a: Use the AtGAD2 promoter (−1714 to −1 bps) with a short overlap for the 5' end of SA at the 3' end that was amplified in Example 6: Step 2a.

Step 1b: Step Use the SA gene that was amplified in Example 6: Step 2b.

Step 1c: Use PCR to amplify the TPAT gene with a short overlap for the 3'end of SA at the 5'end using 500 ng of DNA from *Roseobacter denitrificans* strain. Add 300 nM of the following primers: SA/TPAT (5'-catgcgtccacagactgtcatg-gacggcaatttcaatg-3'; SEQ ID NO:89) and 3'TPAT (5'-ttagc-cgaaaacgcgcgacag-3'; SEQ ID NO:57). Run the fusion PCR as described by Szewczyk et al. (45).

Step 1d: Use the NOS terminator with a short overlap for the 3' end of TPAT at the 5' end of the NOS terminator that was amplified in Example 5: Step 1c.

Step 1e: Combine the amplified fragments (Example 15: steps 1a, 1b, 1c and 1d) and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 16

Development of a transgenic plant that non-constitutively expresses (AtGAD2 promoter) SA fused in frame with a linker to TPAT using fusion PCR Step 1: Make a DNA construct that contains an AtGAD2 (Locus ID#At1g65960) promoter with a SA gene fused in-frame with a linker to a TPAT gene and a NOS terminator in the following manner.

Step 1a: Use the AtGAD2 promoter (−1714 to −1 bps) with a short overlap for the 5' end of SA at the 3' end that was amplified in Example 6: Step 2a.

Step 1b: Use the SA gene that was amplified in Example 6: Step 2b.

Step 1c: Use PCR to amplify the TPAT gene with a linker and short overlap for the 3'end of SA at the 5'end using 500 ng of DNA from *Roseobacter denitrificans* strain. Add 300 nM of the following primers: SAlinkerTPAT (5'-catgcgtc-cacagactgtcagtactgaaggcga agttaacgcggaagaagaaggctttatg-gacggcaatttcaatg-3'; SEQ ID NO:90) and 3'TPAT (5'-ttagc-cgaaaacgcgcgacag-3'; SEQ ID NO:57). Run the fusion PCR as described by Szewczyk et al. (45).

Step 1d: Use the NOS terminator with a short overlap for the 3' end of TPAT at the 5' end of the NOS terminator that was amplified in Example 5: Step 1c.

Step 1e: Combine the amplified fragments (Example 16: steps 1a, 1b, 1c and 1d) 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 17

Development of a Transgenic Plant that Non-Constitutively Expresses (AtGAD2 Promoter) TPAT Fused in Frame with a Linker to a SA Gene using Fusion PCR Step 1: Make a DNA construct that contains an AtGAD2 (Locus ID#At1g65960) promoter with a TPAT gene fused in-frame with a linker to a SA gene and a NOS terminator in the following manner.

Step 1a: Use the AtGAD2 promoter (−1714 to −1 bps) with a short overlap for the 5' end of TPAT at the 3' end that was amplified in Example 5: Step 1a.

Step 1b: Use the TPAT gene that was amplified in Example 5: Step 1b.

Step 1c: Use PCR to amplify the SA with a short overlap for the 3' end of TPAT with a linker at the 5' end using 500 ng of DNA from *Roseobacter denitrificans* strain. Add 300 nM of the following primers: TPATlinkerSA (5'-cgctgtcgcgcgttttcggcagtactgaaggcgaagttaacgcggaagaagaaggctttatgaaaatgaccactgaag-3'; SEQ ID NO:91) and 3'SA (5'-tcagacagtctgtggacgc-3'; SEQ ID NO:62). Run the fusion PCR as described by Szewczyk et al. (45).

Step 1d: Use PCR to amplify the NOS terminator with a short overlap for the 3' end of SA that was amplified in Example 6: Step2c.

Step 1e: Combine the amplified fragments (Example 17: steps 1a, 1b, 1c and 1d) and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 18

Development of a Transgenic Plant that Non-Constitutively expresses (AtGLR1.1 Promoter) ssTDeHase Fused in Frame with lsTDeHase (without a Linker) using Fusion PCR Step 1: Make a DNA construct that contains an AtGLR1.1 (Locus ID #At3g04110) promoter with a ssTDeHase gene fused in-frame with a lsTDeHase gene and a NOS terminator in the following manner.

Step 1a: Use the AtGLR1.1 promoter (−1960 to −1 bps) with a short overlap for the 5' end of ssTDeHase at the 3' end that was amplified in Example 7: Step 1a.

Step 1b: Use the ssTDeHase gene that was amplified in Example 7: Step 1b.

Step 1c: Use PCR to amplify the lsTDeHase gene with a short overlap for the 3' end of ssTDeHase at the 5' end using of DNA from *Roseobacter denitrificans.* Add 300 nM of the following primers: ssTDeHase/lsTDeHase (5'-gcccgcccttcaaggctatgccacatagaccaaagcac-3'; SEQ ID NO:92) and 3'lsTDeHase (5'-tcagagaatttcatcgcgaag-3'; SEQ ID NO:74). Run the fusion PCR as described by Szewczyk et al. (45).

Step 1d: Use the NOS terminator with a short overlap for the 3' end of lsTDeHase at the 5' end of the NOS terminator that was amplified in Example 7: Step 2c.

Step 1e: Combine the amplified fragments (Example 18: steps 1a, 1b, 1c and 1d) and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli,* select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli,* select for antibiotic resistance and confirm the presence of the DNA construct with PCR or by restriction digest analysis.

Step 3: Transform *Agrobacterium tumefaciens:* Transform the DNA construct into *Agrobacterium tumefaciens,* select for antibiotic resistance and confirm the presence of the DNA construct as described in Example 1: Step 2.

Step 4: Transform plant, *Arabidopsis thaliana:* Transform the construct into *Arabidopsis thaliana,* select for antibiotic resistance, select for homozygote plants and confirm the presence of the DNA constructs as described in Example 1: Step 3.

EXAMPLE 19

Development of a Transgenic Plant that Non-Constitutively Expresses (AtGLR1.1 Promoter) ssTDeHase Fused In-Frame with a Linker to lsTDeHase using Fusion PCR Step 1: Make a DNA construct that contains an AtGLR1.1 (Locus ID #At3g04110) promoter with a ssTDeHase gene fused in-frame with a linker and the lsTDeHase gene and a NOS terminator in the following manner.

Step 1a: Use the AtGLR1.1 promoter (−1960 to −1 bps) with a short overlap for the 5' end of ssTDeHase at the 3' end that was amplified in Example 7: Step 1a.

Step 1b: Use the ssTDeHase gene that was amplified in Example 7: Step 1b.

Step 1c: Use PCR to amplify the lsTDeHase gene with a short overlap for the 3' end of ssTDeHase at the 5' end using of DNA from *Roseobacter denitrificans*. Add 300 nM of the following primers: ssTDeHaselinkerlsTDeHase (5'-gcccgc-ccttcaaggctagtactgaaggcgaagttaacgcggaagaagaaggctttatgc-cacatagaccaaagcac-3'; SEQ ID NO:93) and 3'lsTDeHase (5'-tcagagaatttcatcgcgaag-3'; SEQ ID NO:74). Run the fusion PCR as described by Szewczyk et al. (45).

Step 1d: Use the NOS terminator with a short overlap for the 3' end of lsTDeHase at the 5' end of the NOS terminator that was amplified in Example 7: Step 2c.

Step 1e: Combine the amplified fragments (Example 19: steps 1a, 1b, 1c and 1d) and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens:* Transform the DNA construct into *Agrobacterium tumefaciens*, select for antibiotic resistance and confirm the presence of the DNA construct as described in Example 1: Step 2.

Step 4: Transform plant, *Arabidopsis thaliana:* Transform the construct into *Arabidopsis thaliana*, select for antibiotic resistance, select for homozygote plants and confirm the presence of the DNA constructs as described in Example 1: Step 3.

EXAMPLE 20

Development of a Transgenic Plant that Non-Constitutively Expresses (AtGLR1.1 promoter) lsTDeHase Fused In-Frame with a Linker to ssTDeHase using Fusion PCR Step 1: Make a DNA construct that contains an AtGLR1.1 (Locus ID #At3g04110) promoter with a lsTDeHase gene fused in-frame with a linker and the ssTDeHase gene and a NOS terminator in the following manner.

Step 1a: Use the AtGLR1.1 promoter (−1960 to −1 bps) with a short overlap for the 5' end of lsTDeHase at the 3' end that was amplified in Example 7: Step 2a.

Step 1b: Use the lsTDeHase gene that was amplified in Example 7: Step 2b.

Step 1c: Use PCR to amplify the lsTDeHase gene with a short overlap for the 3' end of ssTDeHase at the 5' end using of DNA from *Roseobacter denitrificans*. Add 300 nM of the following primers: lsTDeHaselinkerssTDeHase (5'-cttcgc-gatgaaattctcagtactgaaggcgaagttaacgcggaagaagaaggctttat-gaccaaaacactgacagctc-3'; SEQ ID NO:94) and 3'ssTDeHase (5'-ttaagccttgaagggcgggc-3'; SEQ ID NO:69). Run the fusion PCR as described by Szewczyk et al. (45).

Step 1d: Use the NOS terminator with a short overlap for the 3' end of ssTDeHase at the 5' end of the NOS terminator that was amplified in Example 7: Step 1c.

Step 1e: Combine the amplified fragments (Example 3: steps 1a, 1b, 1c and 1d) and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1f: Combine the amplified fragments from Example 20: steps 1a, 1b, 1c and 1d and 300 nM of the following primers KP2 (5'-ttttggtaccctctttcggaacgagcttcaac-3'; SEQ ID NO:59) and GP5 (5'-tttttttctagagatctagtaacatagatgacac-3'; SEQ ID NO:34). Run the fusion PCR as described by Szewczyk et al. (45). Clone the amplified DNA fragment into pCR4.0-TOPO as described by the manufacturer (Invitrogen).

Step 1g. Transform *E. coli*, select for antibiotic resistance, conduct PCR identification of cloned DNA constructs in transformants, purify DNA and sequence (described in Example 1: step 1e). Digest the plasmid with Acc65I and XbaI, isolate DNA fragment and ligate into the vector pCAMBIA2300 that has been predigested with Acc65I and XbaI.

Step 2. Transform the DNA construct into *E. coli*, select for antibiotic resistance and confirm the presence of the DNA construct with PCR or by restriction digest analysis.

Step 3: Transform *Agrobacterium tumefaciens:* Transform the DNA construct into *Agrobacterium tumefaciens*, select for antibiotic resistance and confirm the presence of the DNA construct as described in Example 1: Step 2.

Step 4: Transform plant, *Arabidopsis thaliana:* Transform the construct into *Arabidopsis thaliana*, select for antibiotic resistance, select for homozygote plants and confirm the presence of the DNA constructs as described in Example 1: Step 3.

What is claimed is:

1. A prokaryotic cell comprising a first exogenous DNA which comprises two separate expression cassettes, wherein a first expression cassette comprises a first promoter operably linked to a first polynucleotide and a second expression cassette comprises a second promoter operably linked to a second polynucleotide, wherein the first polynucleotide encodes cysteine dioxygenase (CDO); and the second polynucleotide encodes sulfinoalanine decarboxylase (SAD), wherein the CDO comprises the amino acid sequence SEQ ID NO:3 or the amino acid sequence SEQ ID NO:4 and wherein the SAD comprises the amino acid sequence SEQ ID NO:7 or the amino acid sequence SEQ ID NO:8.

2. A prokaryotic cell comprising a first exogenous DNA which comprises a single expression cassette, wherein the single expression cassette comprises a promoter operably linked to a polynucleotide which encodes cysteine dioxygenase (CDO) and encodes sulfinoalanine decarboxylase (SAD), wherein the CDO comprises the amino acid sequence SEQ ID NO:3 or the amino acid sequence SEQ ID NO:4 and wherein the SAD comprises the amino acid sequence SEQ ID NO:7 or the amino acid sequence SEQ ID NO:8.

3. The prokaryotic cell of claim 1 which is *E. coli*.

4. The prokaryotic cell of claim 2 which is *E. coli*.

5. A method of producing taurine or hypotaurine, comprising growing the prokaryotic cell of claim 1 under conditions which permit expression of the first and second polynucleotides, thereby producing taurine or hypotaurine.

6. A method of producing taurine or hypotaurine, comprising growing the prokaryotic cell of claim 2 under conditions which permit expression of the polynucleotide, thereby producing taurine or hypotaurine.

7. A method of altering a property of transgenic prokaryotic cells with an agent which increases sulfur or nitrogen concentration in prokaryotic cells, wherein the property is selected from the group consisting of increased taurine, hypotaurine, cysteine and methionine and wherein the transgenic prokaryotic cells comprise an exogenous DNA encoding a cysteine dioxygenase (CDO) and a sulfinoalanine decarboxylase (SAD), wherein the CDO comprises the amino acid sequence SEQ ID NO:3 or the amino acid sequence SEQ ID NO:4 and wherein the SAD comprises the amino acid sequence SEQ ID NO:7 or the amino acid sequence SEQ ID NO:8.

8. The method of claim 7, wherein the agent increases sulfur concentration and the agent is sulfur containing molecule that could be selected from the group consisting of sulfur, sulfite, sulfide, sulfate, hydrogen sulfide, β-mercaptoethanol (2-mercaptoethanol), cysteine, cystine, cyteiene, methionine, taurine, hypotaurine, homotaurine, cysteate, 2-sulfacetaldehyde, N-acetyl thiazolidine 4 carboxylic acid (ATCA), glutathione, and bile.

9. The method of claim 7, wherein the agent increases nitrogen concentration and the agent is nitrogen-containing molecule that could be selected from the group consisting of ammonia, nitrate, nitrite and an amino acid.

10. The method of claim 7, wherein the agent increases nitrogen concentration and the agent is selected from the group consisting of an non-protein amino acids.

11. The method of claim 10, wherein the non-protein amino acid is GABA, citrulline, ornithine or a polyamine.

* * * * *

SEQUENCE LISTING

```
<160> NUMBER OF SEQ ID NOS: 94

<210> SEQ ID NO 1
<211> LENGTH: 603
```

```
<212> TYPE: DNA
<213> ORGANISM: Bos taurus
<220> FEATURE:
<223> OTHER INFORMATION: primer

<400> SEQUENCE: 1

atggagcgga ccgaggtgct aaagccccgc accctggccg atctgatccg cgtcctgcac      60

cagctcttcg ccggcgagga gatcaacgtg gaggaagtgc aggccgtcat ggaagcctat     120

gagagcaacc ccgccgagtg ggcagtgtac gccaagttcg accagtacag gtatactcga     180

aatcttgtgg atcaaggaaa tggaaagttt aatctcatga ttctatgctg ggtgaagga      240

catggcagca gtatccatga tcacaccgac tcccactgct ttctgaagat gctgcaggga     300

aatctaaagg agacattgtt tgcctggcct gacaagaaat ccaatgagat gatcaagaag     360

tctgaaagaa tcttgaggga aaaccagtgt gcctacatca atgattccat tggcttacat     420

cgagtagaga atattagcca tacagagcct gccgtgagcc ttcacttgta tagtccgcct     480

tttgacacat gccacgcctt tgatcaaaga acaggacata aaaacaaagt catcatgaca     540

ttccatagca aatttggaat caagactcca tttacaactt caggatccct ggagaacaac     600

taa                                                                   603


<210> SEQ ID NO 2
<211> LENGTH: 606
<212> TYPE: DNA
<213> ORGANISM: Zebrafish
<220> FEATURE:
<223> OTHER INFORMATION: primer

<400> SEQUENCE: 2

atggagcaga ctgaagtcat gaagcccgag actctggagg atctgatcaa aactctgcat      60

cagatcttcc agagcgactc catcaatgtg gaggaggtgc agaacctgat ggagtcctac     120

cagagcaacc cgcaggactg gatgaagttc gccaagttcg accagtacag gtacaccagg     180

aacctcgtgg atgaaggaaa cggaaagttc aacctgatga tcctgtgctg ggtgaagga      240

cacggcagca gcatccatga ccacacagac tcgcactgct tcctgaagct gctgcagggt     300

cagctgaagg agacgctgtt cgactggccc gaccgcaagc tgcagagcgg catgaagccc     360

cgcggccaga gcgtgctgca ggagaaccag tgcgcgtaca tcaacgactc tctgggactc     420

caccgtgtgg agaatgtgag ccacacagag ccggccgtga gtctgcacct ttacagtcct     480

ccgttccaga gctgccgcac gtttgaccag cgcaccggac accacaacac cgtcaagatg     540

accttctgga gcaaatatgg cgagaggacg ccctatgagc tgagcgtctc gcaggagaat     600

aactga                                                                606


<210> SEQ ID NO 3
<211> LENGTH: 200
<212> TYPE: PRT
<213> ORGANISM: Bos taurus
<220> FEATURE:
<223> OTHER INFORMATION: primer

<400> SEQUENCE: 3

Met Glu Arg Thr Glu Val Leu Lys Pro Arg Thr Leu Ala Asp Leu Ile
 1               5                  10                  15

Arg Val Leu His Gln Leu Phe Ala Gly Glu Glu Ile Asn Val Glu Glu
            20                  25                  30

Val Gln Ala Val Met Glu Ala Tyr Glu Ser Asn Pro Ala Glu Trp Ala
        35                  40                  45
```

```
Val Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Met Leu Gln Gly Asn Leu Lys Glu Thr Leu Phe Ala Trp Pro Asp Lys
            100                 105                 110

Lys Ser Asn Glu Met Ile Lys Lys Ser Glu Arg Ile Leu Arg Glu Asn
        115                 120                 125

Gln Cys Ala Tyr Ile Asn Asp Ser Ile Gly Leu His Arg Val Glu Asn
    130                 135                 140

Ile Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Ile Met Thr Phe His Ser Lys Phe Gly Ile Lys Thr Pro Phe Thr
            180                 185                 190

Thr Ser Gly Ser Leu Glu Asn Asn
        195                 200


<210> SEQ ID NO 4
<211> LENGTH: 201
<212> TYPE: PRT
<213> ORGANISM: Zebrafish
<220> FEATURE:
<223> OTHER INFORMATION: primer

<400> SEQUENCE: 4

Met Glu Gln Thr Glu Val Met Lys Pro Glu Thr Leu Glu Asp Leu Ile
 1               5                  10                  15

Lys Thr Leu His Gln Ile Phe Gln Ser Asp Ser Ile Asn Val Glu Glu
            20                  25                  30

Val Gln Asn Leu Met Glu Ser Tyr Gln Ser Asn Pro Gln Asp Trp Met
        35                  40                  45

Lys Phe Ala Lys Phe Asp Gln Tyr Arg Tyr Thr Arg Asn Leu Val Asp
    50                  55                  60

Glu Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Leu Leu Gln Gly Gln Leu Lys Glu Thr Leu Phe Asp Trp Pro Asp Arg
            100                 105                 110

Lys Leu Gln Ser Gly Met Lys Pro Arg Gly Gln Ser Val Leu Gln Glu
        115                 120                 125

Asn Gln Cys Ala Tyr Ile Asn Asp Ser Leu Gly Leu His Arg Val Glu
    130                 135                 140

Asn Val Ser His Thr Glu Pro Ala Val Ser Leu His Leu Tyr Ser Pro
145                 150                 155                 160

Pro Phe Gln Ser Cys Arg Thr Phe Asp Gln Arg Thr Gly His His Asn
                165                 170                 175

Thr Val Lys Met Thr Phe Trp Ser Lys Tyr Gly Glu Arg Thr Pro Tyr
            180                 185                 190

Glu Leu Ser Val Ser Gln Glu Asn Asn
        195                 200
```

<210> SEQ ID NO 5
<211> LENGTH: 1482
<212> TYPE: DNA
<213> ORGANISM: Equus
<220> FEATURE:
<223> OTHER INFORMATION: primer

<400> SEQUENCE: 5

```
atggctgact ctgaaccgct cctctccctt gatggggacc ccgtggctgc agaagccttg      60

ctccgggatg tgtttgggat cattgtggat gaggtcattc ggaaagggac cagtgcctcc     120

gagaaggtct gcgagtggaa ggagccggag gagctgaagc agctgctgga tttggagctg     180

cggagccatg gggagtcacg ggagcagatc ctggagcggt gccgggctgt catccgctac     240

agcgtgaaga cctgtcaccc tcacttcttc aaccagctct tctcagggtt ggatccccac     300

gctctggccg ggcgcattgt caccgagagc cttaacacca gccagtacac ttatgaaatc     360

gcccccgtgt ttgtgctcat ggaagaagag gtcctgaaga aactccgggc gctggtgggc     420

tggagctctg gcgatggggt cttctgccct ggtggctcca tctccaacat gtatgctgtg     480

aacctggccc gctatcagcg ctacccggat tgcaagcaga ggggcctccg ggcactgccg     540

cccctggccc tcttcacatc gaaggagtgt cattactcca tcaagaaggg agctgctttt     600

ctgggacttg gcactgacag tgtccgagtg gtcaaggcag atgagagagg gaaaatgatc     660

cctgaggatc tggagaggca gatcagtctg gccgaggcgg agggtgctgt gccattcctg     720

gtcactgcca cctctggcac gaccgtgctg gggcctttg atcccctgga ggcgattgct      780

gatgtgtgcc agcgtcatgg gctgtggctg catgtggacg ccgcctgggg tgggagtgtc     840

ctgctctcac agacacacag acatctcctg gctgggatcc agagggcgga ctccgtggcc     900

tggaatcccc acaagctcct cacagcaggc ctgcagtgct cagctctcct gctccgggat     960

acctcgaacc tgctcaagcg ctgccacggg tcccaggcca gctacctctt ccagcaggac    1020

aagttctacg acgtggctct ggacacagga gacaaggtgg tgcagtgcgg ccgccgcgtg    1080

gactgtctga agctgtggct catgtggaag gcccagggcg ggcaagggct ggagcagcga    1140

gtggaccagg ccttcgccct tgcccggtac ctggtggagg aattgaagaa gcgggaagga    1200

tttgagttgg ttatggagcc tgagtttgtc aacgtgtgtt tctggttcgt cccgcccagc    1260

ctgcgggggga aacaggggag tccagattat gctgaaaggc ttgccaaggt ggccccggta   1320

cttaaagagc gcatggtgaa ggagggctcc atgatggttg gctaccagcc ccacgggacc    1380

cggggcaact tttccgcat ggttgtggcc aacccggctc tgacccaggc tgatatggac     1440

ttcttcctca atgagctgga acggctaggc caggacctct ga                       1482
```

<210> SEQ ID NO 6
<211> LENGTH: 1449
<212> TYPE: DNA
<213> ORGANISM: Zebrafish
<220> FEATURE:
<223> OTHER INFORMATION: primer

<400> SEQUENCE: 6

```
atggacgagt ctgatgggaa gctgttcctt actgaggctt tcaacataat catggaagaa      60

attcttaaca aggaagggga cttgaaggag aaggtttgtg agtggaaaga tccagatcag     120

ctgagatctc tcctggacct cgaacttcgg gatcatggag aatgtcatga gaagctgctg     180

cagagggttc gagatgtggc caaatacagc gtaaaaactt gtcatcctcg gttcttcaat     240
```

```
cagctgtttg ctggcgtgga ctatcatgca ctgacaggac ggctcatcac tgaaaccctc    300

aataccagcc aatacaccta tgaagtggct ccagtgtttg tcctgatgga ggaggaagtg    360

atcagtaagc ttcgctctct ggttggctgg tcagaaggag atgggatctt ttgtcctgga    420

ggatccatgt ctaacatgta tgccattaac gtcgctcggt actgggcttt tcctcaagtg    480

aagacaaaag gcttgtgggc cgcaccacgg atggctatat ttacatcaca acagagtcat    540

tactccgtga aaaaaggagc tgcgtttctt ggtattggaa cagaaaatgt tttcattgtg    600

caagtggatg agagcggcag catgatacca gaagacctgg aggcaaaaat tgtgcaggca    660

aaatcccaag acgctgttcc gtttttcgta aacgccacag ccggaaccac agtgcaggga    720

gcctttgacc ctctgaagcg catagctgac atatgtgaaa gaaacggcat gtggatgcat    780

gttgacgccg catggggagg aagcgtgctg ttttccaaaa agcacagaca tctggttgca    840

ggaatagaaa gagcaaactc ggtgacttgg aatcctcaca aaatgcttct gacgggactg    900

cagtgctctg tgattttgtt cagagatact acgaatttgc tcatgcactg tcacagtgcc    960

aaagccacat acttgttcca gcaagacaag ttctacgaca caagtctgga cacgggcgac   1020

aaatccatcc agtgtggccg gaaggtggat tgcctcaagc tctggctcat gtggaaggca   1080

atcggagcta gtggtctttc acagcgtgtc gataaggcct ttgccctcac taggtattta   1140

gttgaagaaa tggagaaacg ggagaatttc cagctggtct gtaaggggcc gtttgtgaac   1200

gtttgcttct ggtttattcc acccagtctg aaaggaaagg agaacagccc agattaccag   1260

gaaagactat ccaaggtggc gccagtcatt aaagagagga tgatgaagcg aggaacgatg   1320

atggtgggat atcagccaat ggatgaacac gtcaacttct tccgcatggt ggttgtttct   1380

ccacagctca caaccaaaga catggatttc ttccttgatg agatggagaa actcgggaag   1440

gatctatga                                                           1449
```

<210> SEQ ID NO 7
<211> LENGTH: 493
<212> TYPE: PRT
<213> ORGANISM: Equus
<220> FEATURE:
<223> OTHER INFORMATION: primer

<400> SEQUENCE: 7

```
Met Ala Asp Ser Glu Pro Leu Leu Ser Leu Asp Gly Asp Pro Val Ala
 1               5                  10                  15

Ala Glu Ala Leu Leu Arg Asp Val Phe Gly Ile Ile Val Asp Glu Val
            20                  25                  30

Ile Arg Lys Gly Thr Ser Ala Ser Glu Lys Val Cys Glu Trp Lys Glu
        35                  40                  45

Pro Glu Glu Leu Lys Gln Leu Leu Asp Leu Glu Leu Arg Ser His Gly
    50                  55                  60

Glu Ser Arg Glu Gln Ile Leu Glu Arg Cys Arg Ala Val Ile Arg Tyr
65                  70                  75                  80

Ser Val Lys Thr Cys His Pro His Phe Phe Asn Gln Leu Phe Ser Gly
                85                  90                  95

Leu Asp Pro His Ala Leu Ala Gly Arg Ile Val Thr Glu Ser Leu Asn
            100                 105                 110

Thr Ser Gln Tyr Thr Tyr Glu Ile Ala Pro Val Phe Val Leu Met Glu
        115                 120                 125

Glu Glu Val Leu Lys Lys Leu Arg Ala Leu Val Gly Trp Ser Ser Gly
    130                 135                 140
```

```
Asp Gly Val Phe Cys Pro Gly Gly Ser Ile Ser Asn Met Tyr Ala Val
145                 150                 155                 160

Asn Leu Ala Arg Tyr Gln Arg Tyr Pro Asp Cys Lys Gln Arg Gly Leu
                165                 170                 175

Arg Ala Leu Pro Pro Leu Ala Leu Phe Thr Ser Lys Glu Cys His Tyr
            180                 185                 190

Ser Ile Lys Lys Gly Ala Ala Phe Leu Gly Leu Gly Thr Asp Ser Val
        195                 200                 205

Arg Val Val Lys Ala Asp Glu Arg Gly Lys Met Ile Pro Glu Asp Leu
    210                 215                 220

Glu Arg Gln Ile Ser Leu Ala Glu Ala Glu Gly Ala Val Pro Phe Leu
225                 230                 235                 240

Val Thr Ala Thr Ser Gly Thr Thr Val Leu Gly Ala Phe Asp Pro Leu
                245                 250                 255

Glu Ala Ile Ala Asp Val Cys Gln Arg His Gly Leu Trp Leu His Val
            260                 265                 270

Asp Ala Ala Trp Gly Gly Ser Val Leu Leu Ser Gln Thr His Arg His
        275                 280                 285

Leu Leu Ala Gly Ile Gln Arg Ala Asp Ser Val Ala Trp Asn Pro His
    290                 295                 300

Lys Leu Leu Thr Ala Gly Leu Gln Cys Ser Ala Leu Leu Leu Arg Asp
305                 310                 315                 320

Thr Ser Asn Leu Leu Lys Arg Cys His Gly Ser Gln Ala Ser Tyr Leu
                325                 330                 335

Phe Gln Gln Asp Lys Phe Tyr Asp Val Ala Leu Asp Thr Gly Asp Lys
            340                 345                 350

Val Val Gln Cys Gly Arg Arg Val Asp Cys Leu Lys Leu Trp Leu Met
        355                 360                 365

Trp Lys Ala Gln Gly Gly Gln Gly Leu Glu Gln Arg Val Asp Gln Ala
    370                 375                 380

Phe Ala Leu Ala Arg Tyr Leu Val Glu Glu Leu Lys Lys Arg Glu Gly
385                 390                 395                 400

Phe Glu Leu Val Met Glu Pro Glu Phe Val Asn Val Cys Phe Trp Phe
                405                 410                 415

Val Pro Pro Ser Leu Arg Gly Lys Gln Gly Ser Pro Asp Tyr Ala Glu
            420                 425                 430

Arg Leu Ala Lys Val Ala Pro Val Leu Lys Glu Arg Met Val Lys Glu
        435                 440                 445

Gly Ser Met Met Val Gly Tyr Gln Pro His Gly Thr Arg Gly Asn Phe
    450                 455                 460

Phe Arg Met Val Val Ala Asn Pro Ala Leu Thr Gln Ala Asp Met Asp
465                 470                 475                 480

Phe Phe Leu Asn Glu Leu Glu Arg Leu Gly Gln Asp Leu
                485                 490


<210> SEQ ID NO 8
<211> LENGTH: 482
<212> TYPE: PRT
<213> ORGANISM: Zebrafish
<220> FEATURE:
<223> OTHER INFORMATION: primer

<400> SEQUENCE: 8

Met Asp Glu Ser Asp Gly Lys Leu Phe Leu Thr Glu Ala Phe Asn Ile
 1               5                  10                  15
```

```
Ile Met Glu Glu Ile Leu Asn Lys Gly Arg Asp Leu Lys Glu Lys Val
            20                  25                  30

Cys Glu Trp Lys Asp Pro Asp Gln Leu Arg Ser Leu Leu Asp Leu Glu
        35                  40                  45

Leu Arg Asp His Gly Glu Cys His Glu Lys Leu Leu Gln Arg Val Arg
    50                  55                  60

Asp Val Ala Lys Tyr Ser Val Lys Thr Cys His Pro Arg Phe Phe Asn
65                  70                  75                  80

Gln Leu Phe Ala Gly Val Asp Tyr His Ala Leu Thr Gly Arg Leu Ile
                85                  90                  95

Thr Glu Thr Leu Asn Thr Ser Gln Tyr Thr Tyr Glu Val Ala Pro Val
            100                 105                 110

Phe Val Leu Met Glu Glu Glu Val Ile Ser Lys Leu Arg Ser Leu Val
        115                 120                 125

Gly Trp Ser Glu Gly Asp Gly Ile Phe Cys Pro Gly Gly Ser Met Ser
    130                 135                 140

Asn Met Tyr Ala Ile Asn Val Ala Arg Tyr Trp Ala Phe Pro Gln Val
145                 150                 155                 160

Lys Thr Lys Gly Leu Trp Ala Ala Pro Arg Met Ala Ile Phe Thr Ser
                165                 170                 175

Gln Gln Ser His Tyr Ser Val Lys Lys Gly Ala Ala Phe Leu Gly Ile
            180                 185                 190

Gly Thr Glu Asn Val Phe Ile Val Gln Val Asp Glu Ser Gly Ser Met
        195                 200                 205

Ile Pro Glu Asp Leu Glu Ala Lys Ile Val Gln Ala Lys Ser Gln Asp
    210                 215                 220

Ala Val Pro Phe Phe Val Asn Ala Thr Ala Gly Thr Thr Val Gln Gly
225                 230                 235                 240

Ala Phe Asp Pro Leu Lys Arg Ile Ala Asp Ile Cys Glu Arg Asn Gly
                245                 250                 255

Met Trp Met His Val Asp Ala Ala Trp Gly Gly Ser Val Leu Phe Ser
            260                 265                 270

Lys Lys His Arg His Leu Val Ala Gly Ile Glu Arg Ala Asn Ser Val
        275                 280                 285

Thr Trp Asn Pro His Lys Met Leu Leu Thr Gly Leu Gln Cys Ser Val
    290                 295                 300

Ile Leu Phe Arg Asp Thr Thr Asn Leu Leu Met His Cys His Ser Ala
305                 310                 315                 320

Lys Ala Thr Tyr Leu Phe Gln Gln Asp Lys Phe Tyr Asp Thr Ser Leu
                325                 330                 335

Asp Thr Gly Asp Lys Ser Ile Gln Cys Gly Arg Lys Val Asp Cys Leu
            340                 345                 350

Lys Leu Trp Leu Met Trp Lys Ala Ile Gly Ala Ser Gly Leu Ser Gln
        355                 360                 365

Arg Val Asp Lys Ala Phe Ala Leu Thr Arg Tyr Leu Val Glu Glu Met
    370                 375                 380

Glu Lys Arg Glu Asn Phe Gln Leu Val Cys Lys Gly Pro Phe Val Asn
385                 390                 395                 400

Val Cys Phe Trp Phe Ile Pro Pro Ser Leu Lys Gly Lys Glu Asn Ser
                405                 410                 415

Pro Asp Tyr Gln Glu Arg Leu Ser Lys Val Ala Pro Val Ile Lys Glu
            420                 425                 430

Arg Met Met Lys Arg Gly Thr Met Met Val Gly Tyr Gln Pro Met Asp
```

```
        435                 440                 445

Glu His Val Asn Phe Phe Arg Met Val Val Val Ser Pro Gln Leu Thr
    450                 455                 460

Thr Lys Asp Met Asp Phe Phe Leu Asp Glu Met Glu Lys Leu Gly Lys
465                 470                 475                 480

Asp Leu


<210> SEQ ID NO 9
<211> LENGTH: 1401
<212> TYPE: DNA
<213> ORGANISM: E. coli
<220> FEATURE:
<223> OTHER INFORMATION: primer

<400> SEQUENCE: 9

atggataaga agcaagtaac ggatttaagg tcggaactac tcgattcacg ttttggtgcg      60

aagtctattt ccactatcgc agaatcaaaa cgttttccgc tgcacgaaat gcgcgacgat     120

gtcgcattcc agattatcaa tgacgaatta tatcttgatg gcaacgctcg tcagaacctg     180

gccactttct gccagacctg ggacgacgaa aatgtccaca aattgatgga tttatccatt     240

aacaaaaact ggatcgacaa agaagaatat ccgcaatccg cagccatcga cctgcgttgc     300

gtaaatatgg ttgccgatct gtggcatgcg cctgcgccga aaaatggtca ggccgttggc     360

accaacacca ttggttcttc cgaggcctgt atgctcggcg ggatggcgat gaaatggcgt     420

tggcgcaagc gtatggaagc tgcaggcaaa ccaacggata aaccaaacct ggtgtgcggt     480

ccggtacaaa tctgctggca taaattcgcc cgctactggg atgtggagct gcgtgagatc     540

cctatgcgcc ccggtcagtt gtttatggac ccgaaacgca tgattgaagc ctgtgacgaa     600

aacaccatcg gcgtggtgcc gactttcggc gtgacctaca ctggtaacta tgagttccca     660

caaccgctgc acgatgcgct ggataaattc caggccgata ccggtatcga catcgacatg     720

cacatcgacg ctgccagcgg tggcttcctg gcaccgttcg tcgccccgga tatcgtctgg     780

gacttccgcc tgccgcgtgt gaaatcgatc agtgcttcag gccataaatt cggtctggct     840

ccgctgggct gcggctgggt tatctggcgt gacgaagaag cgctgccgca ggaactggtg     900

ttcaacgttg actacctggg tggtcaaatt ggtacttttg ccatcaactt ctcccgcccg     960

gcgggtcagg taattgcaca gtactatgaa ttcctgcgcc tcggtcgtga aggctatacc    1020

aaagtacaga acgcctctta ccaggttgcc gcttatctgg cggatgaaat cgccaaactg    1080

gggccgtatg agttcatctg tacgggtcgc ccggacgaag gcatcccggc ggtttgcttc    1140

aaactgaaag atggtgaaga tccgggatac accctgtatg acctctctga acgtctgcgt    1200

ctgcgcggct ggcaggttcc ggccttcact ctcggcggtg aagccaccga catcgtggtg    1260

atgcgcatta tgtgtcgtcg cggcttcgaa atggactttg ctgaactgtt gctggaagac    1320

tacaaagcct ccctgaaata tctcagcgat cacccgaaac tgcagggtat tgcccaacag    1380

aacagcttta aacatacctg a                                              1401


<210> SEQ ID NO 10
<211> LENGTH: 1485
<212> TYPE: DNA
<213> ORGANISM: Arabidopsis
<220> FEATURE:
<223> OTHER INFORMATION: primer

<400> SEQUENCE: 10

atggttttga caaaaaccgc aacgaatgat gaatctgtct gcaccatgtt cggatctcgc      60
```

```
tatgttcgca ctacacttcc caagtatgag attggtgaga attcgatacc gaaagacgct    120

gcatatcaga tcataaaaga tgagctgatg cttgatggta acccgaggct taacctagct    180

tcgtttgtga ctacatggat ggaaccagag tgtgacaaac tcatcatgga ctctatcaac    240

aagaactacg ttgatatgga tgagtaccct gtcacaactg agctccagaa ccgatgtgta    300

aacattatag ctcgactgtt caatgcgcca ctcgaggaat ctgagacggc ggtgggagta    360

gggacagttg gttcttcaga agccatcatg ttagccggat tggccttcaa aagaaaatgg    420

cagaacaaac gcaaggctga gggtaaaccc tatgacaaac ccaacattgt cactggagcc    480

aatgttcaag tttgctggga gaaattcgct cggtacttcg aggtggagct aaaggaagta    540

aacctaagtg aaggttacta cgtgatggat ccagacaaag cagcagaaat ggtagacgag    600

aacacaatct gtgtcgcagc catattggga tccacactca acggtgagtt cgaagacgtg    660

aaacgtctca atgacttgct agtcaagaaa aacgaggaga ctggttggaa cacaccgatc    720

cacgtggatg cagcaagtgg agggttcata gctccgttta tctatcctga attagaatgg    780

gactttagac ttcctttggt taagagtatc aacgtgagtg gtcacaagta tggactggtc    840

tatgctggta ttggttgggt cgtgtggagg gcagcagagg atttgcctga agagcttatc    900

tttcatatta attatcttgg tgctgatcaa cccactttca ctctcaattt ctccaaggga    960

tcgagccaaa ttattgctca atactaccag ctcattcgtc ttggattcga ggggtacaaa   1020

aatgtgatgg agaattgcat agagaacatg gtggttctca aagaagggat agagaaaaca   1080

gagcgtttca acatagtctc aaaggaccaa ggagtgccag tcgtagcctt ctctctcaag   1140

gaccatagtt tccacaacga gttcgagatc tctgagatgc tacgtcgttt tggctggatc   1200

gtcccagctt acactatgcc tgccgatgca cagcacatca cggttctgcg tgttgtcatc   1260

agggaagatt tctcaagaac actcgcggag agacttgttg ctgatatttc gaaggtgctt   1320

catgagctag ataccttgcc ttccaagata tctaagaaga tgggaataga agggatcgcg   1380

gaaaatgtaa aggagaagaa gatggagaag gagattctga tggaagttat tgttggatgg   1440

aggaagtttg tgaaggagag gaagaagatg aatggtgtgt gctaa                   1485
```

<210> SEQ ID NO 11
<211> LENGTH: 466
<212> TYPE: PRT
<213> ORGANISM: E. coli
<220> FEATURE:
<223> OTHER INFORMATION: primer

<400> SEQUENCE: 11

```
Met Asp Lys Lys Gln Val Thr Asp Leu Arg Ser Glu Leu Leu Asp Ser
 1              5                   10                  15

Arg Phe Gly Ala Lys Ser Ile Ser Thr Ile Ala Glu Ser Lys Arg Phe
            20                  25                  30

Pro Leu His Glu Met Arg Asp Asp Val Ala Phe Gln Ile Ile Asn Asp
        35                  40                  45

Glu Leu Tyr Leu Asp Gly Asn Ala Arg Gln Asn Leu Ala Thr Phe Cys
    50                  55                  60

Gln Thr Trp Asp Asp Glu Asn Val His Lys Leu Met Asp Leu Ser Ile
65                  70                  75                  80

Asn Lys Asn Trp Ile Asp Lys Glu Glu Tyr Pro Gln Ser Ala Ala Ile
                85                  90                  95

Asp Leu Arg Cys Val Asn Met Val Ala Asp Leu Trp His Ala Pro Ala
            100                 105                 110
```

```
Pro Lys Asn Gly Gln Ala Val Gly Thr Asn Thr Ile Gly Ser Ser Glu
        115                 120                 125

Ala Cys Met Leu Gly Gly Met Ala Met Lys Trp Arg Trp Arg Lys Arg
    130                 135                 140

Met Glu Ala Ala Gly Lys Pro Thr Asp Lys Pro Asn Leu Val Cys Gly
145                 150                 155                 160

Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465
```

<210> SEQ ID NO 12
<211> LENGTH: 494
<212> TYPE: PRT
<213> ORGANISM: Arabidopsis
<220> FEATURE:
<223> OTHER INFORMATION: primer

<400> SEQUENCE: 12

-continued

```
Met Val Leu Thr Lys Thr Ala Thr Asn Asp Glu Ser Val Cys Thr Met
 1               5                  10                  15

Phe Gly Ser Arg Tyr Val Arg Thr Thr Leu Pro Lys Tyr Glu Ile Gly
            20                  25                  30

Glu Asn Ser Ile Pro Lys Asp Ala Ala Tyr Gln Ile Ile Lys Asp Glu
        35                  40                  45

Leu Met Leu Asp Gly Asn Pro Arg Leu Asn Leu Ala Ser Phe Val Thr
    50                  55                  60

Thr Trp Met Glu Pro Glu Cys Asp Lys Leu Ile Met Asp Ser Ile Asn
65                  70                  75                  80

Lys Asn Tyr Val Asp Met Asp Glu Tyr Pro Val Thr Thr Glu Leu Gln
                85                  90                  95

Asn Arg Cys Val Asn Ile Ile Ala Arg Leu Phe Asn Ala Pro Leu Glu
            100                 105                 110

Glu Ser Glu Thr Ala Val Gly Val Gly Thr Val Gly Ser Ser Glu Ala
        115                 120                 125

Ile Met Leu Ala Gly Leu Ala Phe Lys Arg Lys Trp Gln Asn Lys Arg
    130                 135                 140

Lys Ala Glu Gly Lys Pro Tyr Asp Lys Pro Asn Ile Val Thr Gly Ala
145                 150                 155                 160

Asn Val Gln Val Cys Trp Glu Lys Phe Ala Arg Tyr Phe Glu Val Glu
                165                 170                 175

Leu Lys Glu Val Asn Leu Ser Glu Gly Tyr Tyr Val Met Asp Pro Asp
            180                 185                 190

Lys Ala Ala Glu Met Val Asp Glu Asn Thr Ile Cys Val Ala Ala Ile
        195                 200                 205

Leu Gly Ser Thr Leu Asn Gly Glu Phe Glu Asp Val Lys Arg Leu Asn
    210                 215                 220

Asp Leu Leu Val Lys Lys Asn Glu Glu Thr Gly Trp Asn Thr Pro Ile
225                 230                 235                 240

His Val Asp Ala Ala Ser Gly Gly Phe Ile Ala Pro Phe Ile Tyr Pro
                245                 250                 255

Glu Leu Glu Trp Asp Phe Arg Leu Pro Leu Val Lys Ser Ile Asn Val
            260                 265                 270

Ser Gly His Lys Tyr Gly Leu Val Tyr Ala Gly Ile Gly Trp Val Val
        275                 280                 285

Trp Arg Ala Ala Glu Asp Leu Pro Glu Glu Leu Ile Phe His Ile Asn
    290                 295                 300

Tyr Leu Gly Ala Asp Gln Pro Thr Phe Thr Leu Asn Phe Ser Lys Gly
305                 310                 315                 320

Ser Ser Gln Ile Ile Ala Gln Tyr Tyr Gln Leu Ile Arg Leu Gly Phe
                325                 330                 335

Glu Gly Tyr Lys Asn Val Met Glu Asn Cys Ile Glu Asn Met Val Val
            340                 345                 350

Leu Lys Glu Gly Ile Glu Lys Thr Glu Arg Phe Asn Ile Val Ser Lys
        355                 360                 365

Asp Gln Gly Val Pro Val Val Ala Phe Ser Leu Lys Asp His Ser Phe
    370                 375                 380

His Asn Glu Phe Glu Ile Ser Glu Met Leu Arg Arg Phe Gly Trp Ile
385                 390                 395                 400

Val Pro Ala Tyr Thr Met Pro Ala Asp Ala Gln His Ile Thr Val Leu
                405                 410                 415
```

```
Arg Val Val Ile Arg Glu Asp Phe Ser Arg Thr Leu Ala Glu Arg Leu
            420                 425                 430

Val Ala Asp Ile Ser Lys Val Leu His Glu Leu Asp Thr Leu Pro Ser
        435                 440                 445

Lys Ile Ser Lys Lys Met Gly Ile Glu Gly Ile Ala Glu Asn Val Lys
    450                 455                 460

Glu Lys Lys Met Glu Lys Glu Ile Leu Met Glu Val Ile Val Gly Trp
465                 470                 475                 480

Arg Lys Phe Val Lys Glu Arg Lys Lys Met Asn Gly Val Cys
                485                 490
```

<210> SEQ ID NO 13
<211> LENGTH: 813
<212> TYPE: DNA
<213> ORGANISM: Suis
<220> FEATURE:
<223> OTHER INFORMATION: primer

<400> SEQUENCE: 13

```
atgccccgag acaacatggc ctccctgatc caacggatcg cccgccaggc atgcctcacc     60

ttccggggca gcgggggcgg ccgcagctct tccgatcgcg gcgcggcgcc aggccctgag    120

gcgcctgtgc cgcagggctt cccggagaac ctgagcaagc tgaagagcct gctgacacag    180

gtccgcgcag aggacctgaa catctccccg cgcaaggcca cgctgcagcc gttgccaccc    240

aacctgccgc ccgtcaccta tatgcacatc tacgagactg acggcttcag cctcggcgtg    300

ttcttgctta agagcggcac atccatcccg ctccacgacc accctggcat gcatggcatg    360

ctcaaggtgc tctatggcac cgtgcgcatc agctgcatgg acaagctgga ggcaggcagc    420

gggcaacggc cgcgggcccc gccaccagag cagcagttcg aaccgccgct gctggcccgg    480

gagcgggacg cggtgcggcc gggagtgctg cgctcgcggg ccgagtacac tgaggccagc    540

ggtccctgcg tcctcacgcc gcaccgggac aacctgcacc agatcgacgc tgtggatggg    600

cctgccgcct tcttggatat cctggccccg ccctacgacc cggacgacgg ccgggactgt    660

cactattacc gggtgctgga gcctgtcagg gccaaagagg cctccgactc ggcctgtgac    720

ctgccccgag aggtgtggct tctggagacc ccgcaggccg atgacttttg gtgcgagggg    780

gagccctatc caggtcccag ggtcttccct tga                                 813
```

<210> SEQ ID NO 14
<211> LENGTH: 750
<212> TYPE: DNA
<213> ORGANISM: Zebrafish
<220> FEATURE:
<223> OTHER INFORMATION: primer

<400> SEQUENCE: 14

```
atgacttcca cagtccagaa aatcgccaaa caggccctcg caacattccg aaacccgtct     60

gtcatcggcg agcacaacaa agtgtttttg gagaaccaaa gcaagctgaa aagcctcttg    120

gcggaggtca gagcggcgga cttgaagatc gcagcccgga cccccgagag cgccccggtg    180

ccgcatcagc gcatcgctcc tcccgtcaca tacatgcata tctgcgagac cgactccttc    240

agcatggggg tgtttctgct gaaaacgggg gcttcgatac ccctgcacga ccatccgggg    300

atgtacggca tgctgaaggt gatctacggg aaggtgcgga tcagttgttt cgaccgcctg    360

gataaaccga gagacggcgc cagcggcgtg cagttcaacc ctccgctcat gcccttccag    420

aggggctcct tacggccctc agtgctgaag tccgtcgggg agttcacaga ggacagcagc    480
```

```
ccgtgtgtgc tctcacccca gcaggacaat atccaccaga tagacgctgt tgacggaccc    540

accgctttcc tggacatctt agcacccccg tacgacccag acgaagggag agactgccat    600

tattataaag ttttgcaagc tcattcagag gctgcagata aaaagagtga agtccaggat    660

caaggggacg tgtggctaat ggaaataccc cagcctagtg aattttggtg tggtggtgaa    720

ccatacccag ggcctaaagt gaccctctga                                     750


<210> SEQ ID NO 15
<211> LENGTH: 270
<212> TYPE: PRT
<213> ORGANISM: Suis
<220> FEATURE:
<223> OTHER INFORMATION: primer

<400> SEQUENCE: 15

Met Pro Arg Asp Asn Met Ala Ser Leu Ile Gln Arg Ile Ala Arg Gln
1               5                   10                  15

Ala Cys Leu Thr Phe Arg Gly Ser Gly Gly Gly Arg Ser Ser Ser Asp
            20                  25                  30

Arg Gly Ala Ala Pro Gly Pro Glu Ala Pro Val Pro Gln Gly Phe Pro
        35                  40                  45

Glu Asn Leu Ser Lys Leu Lys Ser Leu Leu Thr Gln Val Arg Ala Glu
    50                  55                  60

Asp Leu Asn Ile Ser Pro Arg Lys Ala Thr Leu Gln Pro Leu Pro Pro
65                  70                  75                  80

Asn Leu Pro Pro Val Thr Tyr Met His Ile Tyr Glu Thr Asp Gly Phe
                85                  90                  95

Ser Leu Gly Val Phe Leu Leu Lys Ser Gly Thr Ser Ile Pro Leu His
            100                 105                 110

Asp His Pro Gly Met His Gly Met Leu Lys Val Leu Tyr Gly Thr Val
        115                 120                 125

Arg Ile Ser Cys Met Asp Lys Leu Glu Ala Gly Ser Gly Gln Arg Pro
    130                 135                 140

Arg Ala Pro Pro Pro Glu Gln Gln Phe Glu Pro Pro Leu Leu Ala Arg
145                 150                 155                 160

Glu Arg Asp Ala Val Arg Pro Gly Val Leu Arg Ser Arg Ala Glu Tyr
                165                 170                 175

Thr Glu Ala Ser Gly Pro Cys Val Leu Thr Pro His Arg Asp Asn Leu
            180                 185                 190

His Gln Ile Asp Ala Val Asp Gly Pro Ala Ala Phe Leu Asp Ile Leu
        195                 200                 205

Ala Pro Pro Tyr Asp Pro Asp Asp Gly Arg Asp Cys His Tyr Tyr Arg
    210                 215                 220

Val Leu Glu Pro Val Arg Ala Lys Glu Ala Ser Asp Ser Ala Cys Asp
225                 230                 235                 240

Leu Pro Arg Glu Val Trp Leu Leu Glu Thr Pro Gln Ala Asp Asp Phe
                245                 250                 255

Trp Cys Glu Gly Glu Pro Tyr Pro Gly Pro Arg Val Phe Pro
            260                 265                 270


<210> SEQ ID NO 16
<211> LENGTH: 249
<212> TYPE: PRT
<213> ORGANISM: Zebrafish
<220> FEATURE:
<223> OTHER INFORMATION: primer
```

<400> SEQUENCE: 16

```
Met Thr Ser Thr Val Gln Lys Ile Ala Lys Gln Ala Leu Ala Thr Phe
 1               5                  10                  15

Arg Asn Pro Ser Val Ile Gly Glu His Asn Lys Val Phe Leu Glu Asn
            20                  25                  30

Gln Ser Lys Leu Lys Ser Leu Leu Ala Glu Val Arg Ala Ala Asp Leu
        35                  40                  45

Lys Ile Ala Ala Arg Thr Pro Glu Ser Ala Pro Val Pro His Gln Arg
    50                  55                  60

Ile Ala Pro Pro Val Thr Tyr Met His Ile Cys Glu Thr Asp Ser Phe
65                  70                  75                  80

Ser Met Gly Val Phe Leu Leu Lys Thr Gly Ala Ser Ile Pro Leu His
                85                  90                  95

Asp His Pro Gly Met Tyr Gly Met Leu Lys Val Ile Tyr Gly Lys Val
            100                 105                 110

Arg Ile Ser Cys Phe Asp Arg Leu Asp Lys Pro Arg Asp Gly Ala Ser
        115                 120                 125

Gly Val Gln Phe Asn Pro Pro Leu Met Pro Phe Gln Arg Gly Ser Leu
    130                 135                 140

Arg Pro Ser Val Leu Lys Ser Val Gly Glu Phe Thr Glu Asp Ser Ser
145                 150                 155                 160

Pro Cys Val Leu Ser Pro Gln Gln Asp Asn Ile His Gln Ile Asp Ala
                165                 170                 175

Val Asp Gly Pro Thr Ala Phe Leu Asp Ile Leu Ala Pro Pro Tyr Asp
            180                 185                 190

Pro Asp Glu Gly Arg Asp Cys His Tyr Tyr Lys Val Leu Gln Ala His
        195                 200                 205

Ser Glu Ala Ala Asp Lys Lys Ser Glu Val Gln Asp Gln Gly Asp Val
    210                 215                 220

Trp Leu Met Glu Ile Pro Gln Pro Ser Glu Phe Trp Cys Gly Gly Glu
225                 230                 235                 240

Pro Tyr Pro Gly Pro Lys Val Thr Leu
                245
```

<210> SEQ ID NO 17
<211> LENGTH: 1392
<212> TYPE: DNA
<213> ORGANISM: Roseobacter denitrificans
<220> FEATURE:
<223> OTHER INFORMATION: primer

<400> SEQUENCE: 17

```
atggacggca atttcaatga aaatgatatc tcccgcgtcg tcgaagcaga ccgcgcgcat      60

atctggcacc atctgagcca gcacaaacct tacgagacaa cagacccgcg catcattgtc     120

gaaggcaagg gcatgaaggt ttgggaccag aagggcaaag agcatcttga tgccgtctcc     180

ggtggggtct ggaccgtcaa tgtcggctat ggccgcgaac gcatcgccaa cgccgtgcgg     240

gaccagttgg tcaagttgaa ctatttcgcc ggctccgcag gctccatccc cggtgccatg     300

ttcgccgagc gtctgatcga gaagatgccg ggctgagcc gcgtttatta ctgcaattcc     360

ggctccgagg cgaatgaaaa agccttcaag atggtccgcc agatcgcgca caaacgctat     420

ggcggcaaaa agcacaaggt gctttatcgc gagcgtgact atcacggcac caccatttcc     480

gccctttccg caggcgggca ggacgaacgg aacgcacaat atggcccctt cacgcccggt     540

ttcgtgcgcg tgccccattg ccttgaatac cgcgcctttg aacaggaagg ggcgccacag     600
```

```
gaaaactacg gtgtctgggc ggcggatcag atcgaaaagg taatcctcgc cgaagggccc    660

gataccgtgg gcggcctgtg ccttgaaccg gtcactgcag gtggcggggt gatcacgccc    720

cccgatggct actgggagcg tgtgcaggaa atctgccaca aatacgacat cctgctgcat    780

atcgacgagg tcgtatgcgg cgtcggtcgg accggcacat ggttcggcta tcagcactac    840

ggcatccagc cggatatggt cacgatggcc aagggtgtcg cgtccggtta cgcggcgatc    900

gcctgccttg tgaccaatga aaaagtcttc gacatgttca aggatgacgc ctcggatccg    960

ctgaactact tccgcgacat ctcgaccttt gggggctgca cggcgggtcc ggcagctgcg   1020

ctggaaaacc tgtcgatcat cgaagaagaa ggcctgctgg acaacaccac ggaacagggg   1080

gcctatatgc tcgactgtct gggcggcttg atggacaagc acaagatcat cggccaggtg   1140

cgcggcaagg ggctgttcct cggtgccgaa ctggtcgagg atcgcgacac gcgcaaaccg   1200

gttgacgaaa ggctcgcgca agcggtggtc gcggactgca tgcaacaggg tgtgatcatc   1260

ggcgtgacca accgctctct gccgggcaag aacaacacgc tgtgtttctc gcccgccctg   1320

atcgccagca aggatgacat tgaccacatc tgcgacgcgg tggacggtgc gctgtcgcgc   1380

gttttcggct aa                                                        1392
```

<210> SEQ ID NO 18
<211> LENGTH: 463
<212> TYPE: PRT
<213> ORGANISM: Roseobacter denitrificans
<220> FEATURE:
<223> OTHER INFORMATION: primer

<400> SEQUENCE: 18

```
Met Asp Gly Asn Phe Asn Glu Asn Asp Ile Ser Arg Val Val Glu Ala
1               5                   10                  15

Asp Arg Ala His Ile Trp His His Leu Ser Gln His Lys Pro Tyr Glu
            20                  25                  30

Thr Thr Asp Pro Arg Ile Ile Val Glu Gly Lys Gly Met Lys Val Trp
        35                  40                  45

Asp Gln Lys Gly Lys Glu His Leu Asp Ala Val Ser Gly Gly Val Trp
    50                  55                  60

Thr Val Asn Val Gly Tyr Gly Arg Glu Arg Ile Ala Asn Ala Val Arg
65                  70                  75                  80

Asp Gln Leu Val Lys Leu Asn Tyr Phe Ala Gly Ser Ala Gly Ser Ile
                85                  90                  95

Pro Gly Ala Met Phe Ala Glu Arg Leu Ile Glu Lys Met Pro Gly Leu
            100                 105                 110

Ser Arg Val Tyr Tyr Cys Asn Ser Gly Ser Glu Ala Asn Glu Lys Ala
        115                 120                 125

Phe Lys Met Val Arg Gln Ile Ala His Lys Arg Tyr Gly Gly Lys Lys
    130                 135                 140

His Lys Val Leu Tyr Arg Glu Arg Asp Tyr His Gly Thr Thr Ile Ser
145                 150                 155                 160

Ala Leu Ser Ala Gly Gly Gln Asp Glu Arg Asn Ala Gln Tyr Gly Pro
                165                 170                 175

Phe Thr Pro Gly Phe Val Arg Val Pro His Cys Leu Glu Tyr Arg Ala
            180                 185                 190

Phe Glu Gln Glu Gly Ala Pro Gln Glu Asn Tyr Gly Val Trp Ala Ala
        195                 200                 205

Asp Gln Ile Glu Lys Val Ile Leu Ala Glu Gly Pro Asp Thr Val Gly
```

```
    210                 215                 220

Gly Leu Cys Leu Glu Pro Val Thr Ala Gly Gly Gly Val Ile Thr Pro
225                 230                 235                 240

Pro Asp Gly Tyr Trp Glu Arg Val Gln Glu Ile Cys His Lys Tyr Asp
                245                 250                 255

Ile Leu Leu His Ile Asp Glu Val Val Cys Gly Val Gly Arg Thr Gly
            260                 265                 270

Thr Trp Phe Gly Tyr Gln His Tyr Gly Ile Gln Pro Asp Met Val Thr
        275                 280                 285

Met Ala Lys Gly Val Ala Ser Gly Tyr Ala Ala Ile Ala Cys Leu Val
    290                 295                 300

Thr Asn Glu Lys Val Phe Asp Met Phe Lys Asp Asp Ala Ser Asp Pro
305                 310                 315                 320

Leu Asn Tyr Phe Arg Asp Ile Ser Thr Phe Gly Gly Cys Thr Ala Gly
                325                 330                 335

Pro Ala Ala Ala Leu Glu Asn Leu Ser Ile Ile Glu Glu Glu Gly Leu
            340                 345                 350

Leu Asp Asn Thr Thr Glu Gln Gly Ala Tyr Met Leu Asp Cys Leu Gly
        355                 360                 365

Gly Leu Met Asp Lys His Lys Ile Ile Gly Gln Val Arg Gly Lys Gly
    370                 375                 380

Leu Phe Leu Gly Ala Glu Leu Val Glu Asp Arg Asp Thr Arg Lys Pro
385                 390                 395                 400

Val Asp Glu Arg Leu Ala Gln Ala Val Val Ala Asp Cys Met Gln Gln
                405                 410                 415

Gly Val Ile Ile Gly Val Thr Asn Arg Ser Leu Pro Gly Lys Asn Asn
            420                 425                 430

Thr Leu Cys Phe Ser Pro Ala Leu Ile Ala Ser Lys Asp Asp Ile Asp
        435                 440                 445

His Ile Cys Asp Ala Val Asp Gly Ala Leu Ser Arg Val Phe Gly
    450                 455                 460


<210> SEQ ID NO 19
<211> LENGTH: 1779
<212> TYPE: DNA
<213> ORGANISM: Roseobacter denitrificans
<220> FEATURE:
<223> OTHER INFORMATION: primer

<400> SEQUENCE: 19

atgaaaatga ccactgaaga agcctttgta aaaaccctgc aagcgcatgg tatcgaacac     60

gccttcggga ttatcggctc ggccatgatg ccgatctccg acattttccc cgatgcgggc    120

atcaaattct gggactgcgc gcatgaaggt tccgcaggca tgatgtctga cggttacacc    180

cgcgccaccg gcaaagtgtc gatgatgatc gcgcagaacg gccccggcat caccaatttc    240

gtgaccgccg tcaaaaccgc ctactggaac cacacgccgc ttctgctcgt gacgccgcaa    300

gccgcgaaca agaccatcgg tcagggcggt tttcaggaag tcgaacagat gaaactcttc    360

gaggacatgg tcgcttatca ggaagaggtg cgcgacccga cccgtgtggc cgaggtcctg    420

acccgcgtga ttgccaaggc aaaacgcctc agcggcccgg cgcagatcaa catcccgcgt    480

gatttctgga cgcaggtggt cgacatcgaa atccccgacc cgattgaatt cgaagcctcc    540

ccgggcggtg aaaactccgt tgcgcaagcc gccgagatgc tctccaacgc caagaatccg    600

gtgatcctga acggggcggg cgtggtcctg tcaaaaggcg gcatcgacgc ctcccgcctt    660
```

```
ctggcagaac gtctggatgc ccccgtctgc gtgggctatc agcacaatga cgcctttccc    720

ggcaaccatc cgctctttgc cggaccactt ggatacaacg gttccaaagc gggcatgcag    780

ctgatcaagg aagccgacgt ggttctgtgc ctcggcacgc gtctcaaccc gttttcgacc    840

ctgcccggct atggcatcga ctattggccc gcagatgcga aaatcattca ggtggacatc    900

aaccccgacc ggatcggcct gaccaagaag gtctcggtcg ggatcgtcgg cgatgcagca    960

aaggtggcca aggggatcct gtcgcagctc tcggacaccg caggcgacga gggccgcgag   1020

gcgcgcaaag cccatatcgc ccagacaaaa tccgcatggg cgcaggagtt gacctcgctc   1080

acccacgagc aggacgatcc gggcaccgac tggaacgtgc gcgcacgcgc ggccaagcct   1140

gactggatga gcccccgcat ggcgtggcgc gcaatccaga gcgcgctgcc ggtggaggcg   1200

atcatttcat ccgacatcgg caacaactgc gccatcggca acgcctaccc ggccttcgaa   1260

gaggggcgca agtatctcgc gccgggtctc ttcggtccct gcggctacgg cctgcccgcc   1320

attgtcggcg ccaagatcgg tcagccccat gtgccggttg tgggtttcgc aggtgacggg   1380

gcctttggca tcgccgtcaa cgaattgacc gccatcggcc gtggtgagtg gcccgcgatc   1440

acgcagatcg tgttccgcaa ctaccagtgg ggcgctgaaa agcgcaactc gaccctgtgg   1500

ttcgaagaca acttcgtcgg caccgagctt gacgaggaag tctcctacgc tggcatcgcc   1560

aatgcgtgcg gcctcaaagg cgtcgtcgcc cgcacgcagg aggaactgac agatgccctc   1620

aacgaggcga tcaaggacca gatggaaaac ggcatcacca cgctgatcga ggccatgatc   1680

aatcaggaac tcggcgatcc cttccgccgc gacgcgatga aaaagcctgt tcaggttgct   1740

gggatcagca aatccgacat gcgtccacag actgtctga                          1779
```

```
<210> SEQ ID NO 20
<211> LENGTH: 592
<212> TYPE: PRT
<213> ORGANISM: Roseobacter denitrificans
<220> FEATURE:
<223> OTHER INFORMATION: primer

<400> SEQUENCE: 20

Met Lys Met Thr Thr Glu Glu Ala Phe Val Lys Thr Leu Gln Ala His
 1               5                  10                  15

Gly Ile Glu His Ala Phe Gly Ile Ile Gly Ser Ala Met Met Pro Ile
            20                  25                  30

Ser Asp Ile Phe Pro Asp Ala Gly Ile Lys Phe Trp Asp Cys Ala His
        35                  40                  45

Glu Gly Ser Ala Gly Met Met Ser Asp Gly Tyr Thr Arg Ala Thr Gly
    50                  55                  60

Lys Val Ser Met Met Ile Ala Gln Asn Gly Pro Gly Ile Thr Asn Phe
65                  70                  75                  80

Val Thr Ala Val Lys Thr Ala Tyr Trp Asn His Thr Pro Leu Leu Leu
                85                  90                  95

Val Thr Pro Gln Ala Ala Asn Lys Thr Ile Gly Gln Gly Gly Phe Gln
            100                 105                 110

Glu Val Glu Gln Met Lys Leu Phe Glu Asp Met Val Ala Tyr Gln Glu
        115                 120                 125

Glu Val Arg Asp Pro Thr Arg Val Ala Glu Val Leu Thr Arg Val Ile
    130                 135                 140

Ala Lys Ala Lys Arg Leu Ser Gly Pro Ala Gln Ile Asn Ile Pro Arg
145                 150                 155                 160

Asp Phe Trp Thr Gln Val Val Asp Ile Glu Ile Pro Asp Pro Ile Glu
```

```
                165                 170                 175

Phe Glu Ala Ser Pro Gly Gly Glu Asn Ser Val Ala Gln Ala Ala Glu
            180                 185                 190

Met Leu Ser Asn Ala Lys Asn Pro Val Ile Leu Asn Gly Ala Gly Val
        195                 200                 205

Val Leu Ser Lys Gly Gly Ile Asp Ala Ser Arg Leu Leu Ala Glu Arg
    210                 215                 220

Leu Asp Ala Pro Val Cys Val Gly Tyr Gln His Asn Asp Ala Phe Pro
225                 230                 235                 240

Gly Asn His Pro Leu Phe Ala Gly Pro Leu Gly Tyr Asn Gly Ser Lys
                245                 250                 255

Ala Gly Met Gln Leu Ile Lys Glu Ala Asp Val Val Leu Cys Leu Gly
            260                 265                 270

Thr Arg Leu Asn Pro Phe Ser Thr Leu Pro Gly Tyr Gly Ile Asp Tyr
        275                 280                 285

Trp Pro Ala Asp Ala Lys Ile Ile Gln Val Asp Ile Asn Pro Asp Arg
    290                 295                 300

Ile Gly Leu Thr Lys Lys Val Ser Val Gly Ile Val Gly Asp Ala Ala
305                 310                 315                 320

Lys Val Ala Lys Gly Ile Leu Ser Gln Leu Ser Asp Thr Ala Gly Asp
                325                 330                 335

Glu Gly Arg Glu Ala Arg Lys Ala His Ile Ala Gln Thr Lys Ser Ala
            340                 345                 350

Trp Ala Gln Glu Leu Thr Ser Leu Thr His Glu Gln Asp Asp Pro Gly
        355                 360                 365

Thr Asp Trp Asn Val Arg Ala Arg Ala Ala Lys Pro Asp Trp Met Ser
    370                 375                 380

Pro Arg Met Ala Trp Arg Ala Ile Gln Ser Ala Leu Pro Val Glu Ala
385                 390                 395                 400

Ile Ile Ser Ser Asp Ile Gly Asn Asn Cys Ala Ile Gly Asn Ala Tyr
                405                 410                 415

Pro Ala Phe Glu Glu Gly Arg Lys Tyr Leu Ala Pro Gly Leu Phe Gly
            420                 425                 430

Pro Cys Gly Tyr Gly Leu Pro Ala Ile Val Gly Ala Lys Ile Gly Gln
        435                 440                 445

Pro His Val Pro Val Val Gly Phe Ala Gly Asp Gly Ala Phe Gly Ile
    450                 455                 460

Ala Val Asn Glu Leu Thr Ala Ile Gly Arg Gly Glu Trp Pro Ala Ile
465                 470                 475                 480

Thr Gln Ile Val Phe Arg Asn Tyr Gln Trp Gly Ala Glu Lys Arg Asn
                485                 490                 495

Ser Thr Leu Trp Phe Glu Asp Asn Phe Val Gly Thr Glu Leu Asp Glu
            500                 505                 510

Glu Val Ser Tyr Ala Gly Ile Ala Asn Ala Cys Gly Leu Lys Gly Val
        515                 520                 525

Val Ala Arg Thr Gln Glu Glu Leu Thr Asp Ala Leu Asn Glu Ala Ile
    530                 535                 540

Lys Asp Gln Met Glu Asn Gly Ile Thr Thr Leu Ile Glu Ala Met Ile
545                 550                 555                 560

Asn Gln Glu Leu Gly Asp Pro Phe Arg Arg Asp Ala Met Lys Lys Pro
                565                 570                 575

Val Gln Val Ala Gly Ile Ser Lys Ser Asp Met Arg Pro Gln Thr Val
            580                 585                 590
```

<210> SEQ ID NO 21
<211> LENGTH: 387
<212> TYPE: DNA
<213> ORGANISM: Roseobacter denitrificans
<220> FEATURE:
<223> OTHER INFORMATION: primer

<400> SEQUENCE: 21

```
atgaccaaaa cactgacagc tcaggacttg tccgacacct ttgacgcctt caatcgccat     60

gacgttgatg gcgtcatgac acatttcgcc gatgattgcg tgttctacac cgtgggcggg    120

gatgaagcct atggcgccaa agtcgaaggc gcagaagcga ttgccaaagc attctctgcc    180

gtctgggcgg gcatgaagga cgcccattgg gatcatcaca gccactttgt gcatggggat    240

cgcgccgtat ccgaatggac gttctccgga actggcgcgg acggcatgcg catcgaagca    300

cagggcgctg acctctttac cctgcgcgac ggcaagatca tcgtgaaaca ggccctgcgc    360

aaatcccgcc cgcccttcaa ggcttaa                                        387
```

<210> SEQ ID NO 22
<211> LENGTH: 128
<212> TYPE: PRT
<213> ORGANISM: Roseobacter denitrificans
<220> FEATURE:
<223> OTHER INFORMATION: primer

<400> SEQUENCE: 22

```
Met Thr Lys Thr Leu Thr Ala Gln Asp Leu Ser Asp Thr Phe Asp Ala
1               5                   10                  15

Phe Asn Arg His Asp Val Asp Gly Val Met Thr His Phe Ala Asp Asp
            20                  25                  30

Cys Val Phe Tyr Thr Val Gly Gly Asp Glu Ala Tyr Gly Ala Lys Val
        35                  40                  45

Glu Gly Ala Glu Ala Ile Ala Lys Ala Phe Ser Ala Val Trp Ala Gly
    50                  55                  60

Met Lys Asp Ala His Trp Asp His His Ser His Phe Val His Gly Asp
65                  70                  75                  80

Arg Ala Val Ser Glu Trp Thr Phe Ser Gly Thr Gly Ala Asp Gly Met
                85                  90                  95

Arg Ile Glu Ala Gln Gly Ala Asp Leu Phe Thr Leu Arg Asp Gly Lys
            100                 105                 110

Ile Ile Val Lys Gln Ala Leu Arg Lys Ser Arg Pro Pro Phe Lys Ala
        115                 120                 125
```

<210> SEQ ID NO 23
<211> LENGTH: 1395
<212> TYPE: DNA
<213> ORGANISM: Roseobacter denitrificans
<220> FEATURE:
<223> OTHER INFORMATION: primer

<400> SEQUENCE: 23

```
atgccacata gaccaaagca ctggcccaag gccagctacg atcccaaata cgatcctatc     60

gtcgacgcgg gtcccggtca caaccgggac cacgcaccga cctattggat tggtacggcg    120

gggacgccac ctgaagatga cgggccggtg tcgggtgaca tcgatgcgga tgtcgtcgtt    180

gtcggctctg gctatacagg tctgtctacc gcaatccacc tggcgaagga ccacggcatc    240

aaggcgcatg tccttgaagc caacacagtc gcctggggct gttccacccg caatggcggg    300
```

```
caggcacaga tttcttccgg tcgtctcaag cggtcggagt ggatcaagcg gtggggcgtg    360

gatgtcgcca aaggcatgca cgccgaggtc tgtgaagcct tcgaactgtt caatgatctg    420

atcgggtcag atgacattga ttgcgacccg caaaccgggg gccatttcta tattgcccac    480

cgcgaaaagg tcatggcgaa gctggaaaag gaatgtgccg tcctgaacga cacgtttggc    540

tatggctctc gcattctgtc gcgcgacgaa ctacacgaaa aatacgtgcg ggatcaggaa    600

gcacacggtg ccctttggga accggacggg acctcgatcc acgcggcaaa actggccttc    660

agctacgtgc gtcttgcgcg caaactcggc gccaagatcc acacggccag cccggtcatg    720

gggtggaaga ccgtgaacgg tgtgcatcac ctcaccacgc ccggtggcac ggtgcgcgca    780

cgtgccgtgg ccttggcgac agcgggctac acaccgccgg ggctgaacga aaagaccaag    840

caccggctca tgccgatcct gtcaaactcc atcgtgacgc gtccgctgag cgatgaggaa    900

aaggcgggat gcggttttca ggtgaaatct ccgctgactg acacgcgcac cttgcggcac    960

tactaccgct atctgcccga cggacgggtc cagatcggca gccgcagtgc gattacaggt   1020

cgagacgcag agaaccccag acatctggag cttctgcaga aaggtctcta tcgcaagttc   1080

cccgtgctcg aaggcattga actggattac tcctggtggg gatgggtgga tgtcagccat   1140

gacatgatgc cacgcatttt ccagccaaac ccgaagcaaa caatctttta tgcgatgggc   1200

tacggcggca acggggtgat gtattccgca caggccggca agcgcatggc gcaaatggtt   1260

gcgggcgaag gcaaggacct caaacttccg atcttcacct cgcaactgcc aagccacggt   1320

gttctgacac ccttccgcag gttgggccag cgcatggcct acccctacta ctaccttcgc   1380

gatgaaattc tctga                                                     1395
```

<210> SEQ ID NO 24
<211> LENGTH: 464
<212> TYPE: PRT
<213> ORGANISM: Roseobacter denitrificans
<220> FEATURE:
<223> OTHER INFORMATION: primer

<400> SEQUENCE: 24

```
Met Pro His Arg Pro Lys His Trp Pro Lys Ala Ser Tyr Asp Pro Lys
 1               5                  10                  15

Tyr Asp Pro Ile Val Asp Ala Gly Pro Gly His Asn Arg Asp His Ala
            20                  25                  30

Pro Thr Tyr Trp Ile Gly Thr Ala Gly Thr Pro Pro Glu Asp Asp Gly
        35                  40                  45

Pro Val Ser Gly Asp Ile Asp Ala Asp Val Val Val Val Gly Ser Gly
    50                  55                  60

Tyr Thr Gly Leu Ser Thr Ala Ile His Leu Ala Lys Asp His Gly Ile
65                  70                  75                  80

Lys Ala His Val Leu Glu Ala Asn Thr Val Ala Trp Gly Cys Ser Thr
                85                  90                  95

Arg Asn Gly Gly Gln Ala Gln Ile Ser Ser Gly Arg Leu Lys Arg Ser
            100                 105                 110

Glu Trp Ile Lys Arg Trp Gly Val Asp Val Ala Lys Gly Met His Ala
        115                 120                 125

Glu Val Cys Glu Ala Phe Glu Leu Phe Asn Asp Leu Ile Gly Ser Asp
    130                 135                 140

Asp Ile Asp Cys Asp Pro Gln Thr Gly Gly His Phe Tyr Ile Ala His
145                 150                 155                 160

Arg Glu Lys Val Met Ala Lys Leu Glu Lys Glu Cys Ala Val Leu Asn
```

```
                165                 170                 175

Asp Thr Phe Gly Tyr Gly Ser Arg Ile Leu Ser Arg Asp Glu Leu His
            180                 185                 190

Glu Lys Tyr Val Arg Asp Gln Glu Ala His Gly Ala Leu Trp Glu Pro
        195                 200                 205

Asp Gly Thr Ser Ile His Ala Ala Lys Leu Ala Phe Ser Tyr Val Arg
    210                 215                 220

Leu Ala Arg Lys Leu Gly Ala Lys Ile His Thr Ala Ser Pro Val Met
225                 230                 235                 240

Gly Trp Lys Thr Val Asn Gly Val His His Leu Thr Thr Pro Gly Gly
                245                 250                 255

Thr Val Arg Ala Arg Ala Val Ala Leu Ala Thr Ala Gly Tyr Thr Pro
            260                 265                 270

Pro Gly Leu Asn Glu Lys Thr Lys His Arg Leu Met Pro Ile Leu Ser
        275                 280                 285

Asn Ser Ile Val Thr Arg Pro Leu Ser Asp Glu Glu Lys Ala Gly Cys
    290                 295                 300

Gly Phe Gln Val Lys Ser Pro Leu Thr Asp Thr Arg Thr Leu Arg His
305                 310                 315                 320

Tyr Tyr Arg Tyr Leu Pro Asp Gly Arg Val Gln Ile Gly Ser Arg Ser
                325                 330                 335

Ala Ile Thr Gly Arg Asp Ala Glu Asn Pro Arg His Leu Glu Leu Leu
            340                 345                 350

Gln Lys Gly Leu Tyr Arg Lys Phe Pro Val Leu Glu Gly Ile Glu Leu
        355                 360                 365

Asp Tyr Ser Trp Trp Gly Trp Val Asp Val Ser His Asp Met Met Pro
    370                 375                 380

Arg Ile Phe Gln Pro Asn Pro Lys Gln Thr Ile Phe Tyr Ala Met Gly
385                 390                 395                 400

Tyr Gly Gly Asn Gly Val Met Tyr Ser Ala Gln Ala Gly Lys Arg Met
                405                 410                 415

Ala Gln Met Val Ala Gly Glu Gly Lys Asp Leu Lys Leu Pro Ile Phe
            420                 425                 430

Thr Ser Gln Leu Pro Ser His Gly Val Leu Thr Pro Phe Arg Arg Leu
        435                 440                 445

Gly Gln Arg Met Ala Tyr Pro Tyr Tyr Tyr Leu Arg Asp Glu Ile Leu
    450                 455                 460
```

<210> SEQ ID NO 25
<211> LENGTH: 852
<212> TYPE: DNA
<213> ORGANISM: E. coli
<220> FEATURE:
<223> OTHER INFORMATION: primer

<400> SEQUENCE: 25

```
atgagtgaac gtctgagcat taccccgctg ggccgtata tcggcgcaca aatttcgggt     60

gccgacctga cgcgcccgtt aagcgataat cagtttgaac agctttacca tgcggtgctg    120

cgccatcagg tggtgtttct acgcgatcaa gctattacgc cgcagcagca acgcgcgctg    180

gcccagcgtt ttggcgaatt gcatattcac cctgtttacc cgcatgccga aggggttgac    240

gagatcatcg tgctggatac ccataacgat aatccgccag ataacgacaa ctggcatacc    300

gatgtgacat ttattgaaac gccacccgca ggggcgattc tggcagctaa agagttacct    360

tcgaccggcg gtgatacgct ctggaccagc ggtattgcgg cctatgaggc gctctctgtt    420
```

```
cccttccgcc agctgctgag tgggctgcgt gcggagcatg atttccgtaa atcgttcccg    480

gaatacaaat accgcaaaac cgaggaggaa catcaacgct ggcgcgaggc ggtcgcgaaa    540

aacccgccgt tgctacatcc ggtggtgcga acgcatccgg tgagcggtaa acaggcgctg    600

tttgtgaatg aaggctttac tacgcgaatt gttgatgtga gcgagaaaga gagcgaagcc    660

ttgttaagtt ttttgtttgc ccatatcacc aaaccggagt ttcaggtgcg ctggcgctgg    720

caaccaaatg atattgcgat ttgggataac cgcgtgaccc agcactatgc caatgccgat    780

tacctgccac agcgacggat aatgcatcgg gcgacgatcc ttggggataa accgttttat    840

cgggcggggt aa                                                         852
```

```
<210> SEQ ID NO 26
<211> LENGTH: 283
<212> TYPE: PRT
<213> ORGANISM: E. coli
<220> FEATURE:
<223> OTHER INFORMATION: primer

<400> SEQUENCE: 26

Met Ser Glu Arg Leu Ser Ile Thr Pro Leu Gly Pro Tyr Ile Gly Ala
1               5                   10                  15

Gln Ile Ser Gly Ala Asp Leu Thr Arg Pro Leu Ser Asp Asn Gln Phe
            20                  25                  30

Glu Gln Leu Tyr His Ala Val Leu Arg His Gln Val Val Phe Leu Arg
        35                  40                  45

Asp Gln Ala Ile Thr Pro Gln Gln Gln Arg Ala Leu Ala Gln Arg Phe
    50                  55                  60

Gly Glu Leu His Ile His Pro Val Tyr Pro His Ala Glu Gly Val Asp
65                  70                  75                  80

Glu Ile Ile Val Leu Asp Thr His Asn Asp Asn Pro Pro Asp Asn Asp
                85                  90                  95

Asn Trp His Thr Asp Val Thr Phe Ile Glu Thr Pro Pro Ala Gly Ala
            100                 105                 110

Ile Leu Ala Ala Lys Glu Leu Pro Ser Thr Gly Gly Asp Thr Leu Trp
        115                 120                 125

Thr Ser Gly Ile Ala Ala Tyr Glu Ala Leu Ser Val Pro Phe Arg Gln
    130                 135                 140

Leu Leu Ser Gly Leu Arg Ala Glu His Asp Phe Arg Lys Ser Phe Pro
145                 150                 155                 160

Glu Tyr Lys Tyr Arg Lys Thr Glu Glu Glu His Gln Arg Trp Arg Glu
                165                 170                 175

Ala Val Ala Lys Asn Pro Pro Leu Leu His Pro Val Val Arg Thr His
            180                 185                 190

Pro Val Ser Gly Lys Gln Ala Leu Phe Val Asn Glu Gly Phe Thr Thr
        195                 200                 205

Arg Ile Val Asp Val Ser Glu Lys Glu Ser Glu Ala Leu Leu Ser Phe
    210                 215                 220

Leu Phe Ala His Ile Thr Lys Pro Glu Phe Gln Val Arg Trp Arg Trp
225                 230                 235                 240

Gln Pro Asn Asp Ile Ala Ile Trp Asp Asn Arg Val Thr Gln His Tyr
                245                 250                 255

Ala Asn Ala Asp Tyr Leu Pro Gln Arg Arg Ile Met His Arg Ala Thr
            260                 265                 270

Ile Leu Gly Asp Lys Pro Phe Tyr Arg Ala Gly
```

275 280

<210> SEQ ID NO 27
<211> LENGTH: 32
<212> TYPE: DNA
<213> ORGANISM: Artificial Sequence
<220> FEATURE:
<223> OTHER INFORMATION: primer

<400> SEQUENCE: 27
ttttggtacc cacatttgca aaatgatgaa tg 32

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
catgacttca gtctgctcca tccaatctgg ttaccgcatt g 41

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
atggagcaga ctgaagtcat g 21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
tcagttattc tcctgcgaga c 21

<210> SEQ ID NO 31
<211> LENGTH: 41
<212> TYPE: DNA
<213> ORGANISM: Artificial Sequence
<220> FEATURE:
<223> OTHER INFORMATION: primer

<400> SEQUENCE: 31
gtctcgcagg agaataactg agctaccgag ctcgaatttc c 41

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
cacgacgttg taaaacgacg gc 22

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
ttttggtacc gtttacatat ggagatgatg tc 32

<210> SEQ ID NO 34
<211> LENGTH: 35
<212> TYPE: DNA
<213> ORGANISM: Artificial Sequence
<220> FEATURE:
<223> OTHER INFORMATION: primer

<400> SEQUENCE: 34 tttttttct agagatctag taacatagat gacac 35

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
caatgcctaa taatgtctag c 21

<210> SEQ ID NO 36
<211> LENGTH: 43
<212> TYPE: DNA
<213> ORGANISM: Artificial Sequence
<220> FEATURE:
<223> OTHER INFORMATION: primer

<400> SEQUENCE: 36
catgacttca gtctgctcca tgccgtttga ttttgaattt gag 43

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
ttttcccggg attcttgaat tacgattgta cc 32

<210> SEQ ID NO 38
<211> LENGTH: 46
<212> TYPE: DNA
<213> ORGANISM: Artificial Sequence
<220> FEATURE:
<223> OTHER INFORMATION: primer

<400> SEQUENCE: 38
cagcttccca tcagactcgt ccatgccgtt tgattttgaa tttgag 46

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
atggacgagt ctgatgggaa gctg 24

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
tcatagatcc ttcccgagtt tc 22

<210> SEQ ID NO 41
<211> LENGTH: 42
<212> TYPE: DNA
<213> ORGANISM: Artificial Sequence
<220> FEATURE:
<223> OTHER INFORMATION: primer

<400> SEQUENCE: 41
gaaactcggg aaggatctat gagctaccga gctcgaattt cc 42

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
aaaaatctag aattcttgaa ttacgattgt acc 33

<210> SEQ ID NO 43
<211> LENGTH: 35
<212> TYPE: DNA
<213> ORGANISM: Artificial Sequence
<220> FEATURE:
<223> OTHER INFORMATION: primer

<400> SEQUENCE: 43 ttttttgtc gacgatctag taacatagat gacac 35

<210> SEQ ID NO 44
<211> LENGTH: 43
<212> TYPE: DNA
<213> ORGANISM: Artificial Sequence
<220> FEATURE:
<223> OTHER INFORMATION: primer

<400> SEQUENCE: 44
cgttacttgc ttcttatcca tgccgtttga ttttgaattt gag 43

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
atggataaga agcaagtaac g 21

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
tcaggtatgt ttaaagctgt tc 22

<210> SEQ ID NO 47
<211> LENGTH: 42
<212> TYPE: DNA
<213> ORGANISM: Artificial Sequence
<220> FEATURE:
<223> OTHER INFORMATION: primer

<400> SEQUENCE: 47
gaacagcttt aaacatacct gagctaccga gctcgaattt cc 42

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
accaaaggat accctgattt g 21

<210> SEQ ID NO 49
<211> LENGTH: 44
<212> TYPE: DNA
<213> ORGANISM: Artificial Sequence
<220> FEATURE:
<223> OTHER INFORMATION: primer

<400> SEQUENCE: 49
gattttctgg actgtggaag tcatcacgga gatgagagag agag 44

<210> SEQ ID NO 50
<211> LENGTH: 24
<212> TYPE: DNA
<213> ORGANISM: Artificial Sequence
<220> FEATURE:
<223> OTHER INFORMATION: primer

<400> SEQUENCE: 50
atgacttcca cagtccagaa aatc 24

<210> SEQ ID NO 51
<211> LENGTH: 19
<212> TYPE: DNA
<213> ORGANISM: Artificial Sequence
<220> FEATURE:
<223> OTHER INFORMATION: primer

<400> SEQUENCE: 51
tcagagggtc actttaggc 19

<210> SEQ ID NO 52
<211> LENGTH: 39
<212> TYPE: DNA
<213> ORGANISM: Artificial Sequence
<220> FEATURE:
<223> OTHER INFORMATION: primer

<400> SEQUENCE: 52
gcctaaagtg accctctgag ctaccgagct cgaatttcc 39

<210> SEQ ID NO 53

<211> LENGTH: 32
<212> TYPE: DNA
<213> ORGANISM: Artificial Sequence
<220> FEATURE:
<223> OTHER INFORMATION: primer

<400> SEQUENCE: 53
aaaaaggtac cgatatttga gcaaaactgt gg 32

<210> SEQ ID NO 54
<211> LENGTH: 22
<212> TYPE: DNA
<213> ORGANISM: Artificial Sequence
<220> FEATURE:
<223> OTHER INFORMATION: primer

<400> SEQUENCE: 54
tcttaccttg tcctgcaacg ag 22

<210> SEQ ID NO 55
<211> LENGTH: 41
<212> TYPE: DNA
<213> ORGANISM: Artificial Sequence
<220> FEATURE:
<223> OTHER INFORMATION: primer

<400> SEQUENCE: 55
cattgaaatt gccgtccatc tttgtttctg tttagtgaaa g 41

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
atggacggca atttcaatg 19

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
ttagccgaaa acgcgcgaca g 21

<210> SEQ ID NO 58
<211> LENGTH: 41
<212> TYPE: DNA
<213> ORGANISM: Artificial Sequence
<220> FEATURE:
<223> OTHER INFORMATION: primer

<400> SEQUENCE: 58
ctgtcgcgcg ttttcggcta agctaccgag ctcgaatttc c 41

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ttttggtacc ctctttcgga acgagcttca ac 32

<210> SEQ ID NO 60
<211> LENGTH: 41
<212> TYPE: DNA
<213> ORGANISM: Artificial Sequence
<220> FEATURE:
<223> OTHER INFORMATION: primer

<400> SEQUENCE: 60
cttcagtggt cattttcatc tttgtttctg tttagtgaaa g 41

<210> SEQ ID NO 61
<211> LENGTH: 19
<212> TYPE: DNA
<213> ORGANISM: Artificial Sequence
<220> FEATURE:
<223> OTHER INFORMATION: primer

<400> SEQUENCE: 61
atgaaaatga ccactgaag 19

<210> SEQ ID NO 62
<211> LENGTH: 19
<212> TYPE: DNA
<213> ORGANISM: Artificial Sequence
<220> FEATURE:
<223> OTHER INFORMATION: primer

<400> SEQUENCE: 62
tcagacagtc tgtggacgc 19

<210> SEQ ID NO 63
<211> LENGTH: 39
<212> TYPE: DNA
<213> ORGANISM: Artificial Sequence
<220> FEATURE:
<223> OTHER INFORMATION: primer

<400> SEQUENCE: 63
gcgtccacag actgtctgag ctaccgagct cgaatttcc 39

<210> SEQ ID NO 64
<211> LENGTH: 30
<212> TYPE: DNA
<213> ORGANISM: Artificial Sequence
<220> FEATURE:
<223> OTHER INFORMATION: primer

<400> SEQUENCE: 64
tttttctaga gaacgagctt caacgtagcc 30

<210> SEQ ID NO 65
<211> LENGTH: 33
<212> TYPE: DNA
<213> ORGANISM: Artificial Sequence
<220> FEATURE:
<223> OTHER INFORMATION: primer

<400> SEQUENCE: 65
aaaaaaagct tgatctagta acatagatga cac 33

<210> SEQ ID NO 66
<211> LENGTH: 24
<212> TYPE: DNA

<213> ORGANISM: Artificial Sequence
<220> FEATURE:
<223> OTHER INFORMATION: primer

<400> SEQUENCE: 66
gatcatacat attcatactt gatg 24

<210> SEQ ID NO 67
<211> LENGTH: 47
<212> TYPE: DNA
<213> ORGANISM: Artificial Sequence
<220> FEATURE:
<223> OTHER INFORMATION: primer

<400> SEQUENCE: 67
gagctgtcag tgttttggtc atataatttc ttgtatagct ctgtaac 47

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
atgaccaaaa cactgacagc tc 22

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ttaagccttg aagggcgggc 20

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
gcccgccctt caaggcttaa gctaccgagc tcgaatttcc 40

<210> SEQ ID NO 71
<211> LENGTH: 30
<212> TYPE: DNA
<213> ORGANISM: Artificial Sequence
<220> FEATURE:
<223> OTHER INFORMATION: primer

<400> SEQUENCE: 71
ttttggtacc cgaagctcaa tcgtctcgag 30

<210> SEQ ID NO 72
<211> LENGTH: 46
<212> TYPE: DNA
<213> ORGANISM: Artificial Sequence
<220> FEATURE:
<223> OTHER INFORMATION: primer

<400> SEQUENCE: 72
gtgctttggt ctatgtggca tataatttct tgtatagctc tgtaac 46

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
atgccacata gaccaaagca c 21

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
tcagagaatt tcatcgcgaa g 21

<210> SEQ ID NO 75
<211> LENGTH: 41
<212> TYPE: DNA
<213> ORGANISM: Artificial Sequence
<220> FEATURE:
<223> OTHER INFORMATION: primer

<400> SEQUENCE: 75
cttcgcgatg aaattctctg agctaccgag ctcgaatttc c 41

<210> SEQ ID NO 76
<211> LENGTH: 31
<212> TYPE: DNA
<213> ORGANISM: Artificial Sequence
<220> FEATURE:
<223> OTHER INFORMATION: primer

<400> SEQUENCE: 76
aaaaatctag acgaagctca atcgtctcga g 31

<210> SEQ ID NO 77
<211> LENGTH: 19
<212> TYPE: DNA
<213> ORGANISM: Artificial Sequence
<220> FEATURE:
<223> OTHER INFORMATION: primer

<400> SEQUENCE: 77
tcacaatcga tggactctc 19

<210> SEQ ID NO 78
<211> LENGTH: 43
<212> TYPE: DNA
<213> ORGANISM: Artificial Sequence
<220> FEATURE:
<223> OTHER INFORMATION: primer

<400> SEQUENCE: 78
gtaatgctca gacgttcact cattgctatg tgtgttttgt agc 43

<210> SEQ ID NO 79
<211> LENGTH: 23
<212> TYPE: DNA
<213> ORGANISM: Artificial Sequence
<220> FEATURE:

<223> OTHER INFORMATION: primer

<400> SEQUENCE: 79
atgagtgaac gtctgagcat tac 23

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
ttaccccgcc cgataaaacg 20

<210> SEQ ID NO 81
<211> LENGTH: 40
<212> TYPE: DNA
<213> ORGANISM: Artificial Sequence
<220> FEATURE:
<223> OTHER INFORMATION: primer

<400> SEQUENCE: 81
cgttttatcg ggcggggtaa gctaccgagc tcgaatttcc 40

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
ttttggtacc ctatattggt gtcattttgc c 31

<210> SEQ ID NO 83
<211> LENGTH: 46
<212> TYPE: DNA
<213> ORGANISM: Artificial Sequence
<220> FEATURE:
<223> OTHER INFORMATION: primer

<400> SEQUENCE: 83
gagcgtctcg caggagaata acatggacga gtctgatggg aagctg 46

<210> SEQ ID NO 84
<211> LENGTH: 85
<212> TYPE: DNA
<213> ORGANISM: Artificial Sequence
<220> FEATURE:
<223> OTHER INFORMATION: primer

<400> SEQUENCE: 84
gagcgtctcg caggagaata acagtactga aggcgaagtt aacgcggaag aagaaggctt 60
tatggacgag tctgatggga agctg 85

<210> SEQ ID NO 85
<211> LENGTH: 79
<212> TYPE: DNA
<213> ORGANISM: Artificial Sequence
<220> FEATURE:
<223> OTHER INFORMATION: primer

<400> SEQUENCE: 85
gaaactcggg aaggatctaa gtactgaagg cgaagttaac gcggaagaag aaggctttat 60
ggagcagact gaagtcatg 79

<210> SEQ ID NO 86
<211> LENGTH: 43
<212> TYPE: DNA
<213> ORGANISM: Artificial Sequence
<220> FEATURE:
<223> OTHER INFORMATION: primer

<400> SEQUENCE: 86
gagcgtctcg caggagaata acatggataa gaagcaagta acg 43

<210> SEQ ID NO 87
<211> LENGTH: 82
<212> TYPE: DNA
<213> ORGANISM: Artificial Sequence
<220> FEATURE:
<223> OTHER INFORMATION: primer

<400> SEQUENCE: 87
gagcgtctcg caggagaata acagtactga aggcgaagtt aacgcggaag aagaaggctt 60
tatggataag aagcaagtaa cg 82

<210> SEQ ID NO 88
<211> LENGTH: 79
<212> TYPE: DNA
<213> ORGANISM: Artificial Sequence
<220> FEATURE:
<223> OTHER INFORMATION: primer

<400> SEQUENCE: 88
gaacagcttt aaacatacca gtactgaagg cgaagttaac gcggaagaag aaggctttat 60
ggagcagact gaagtcatg 79

<210> SEQ ID NO 89
<211> LENGTH: 38
<212> TYPE: DNA
<213> ORGANISM: Artificial Sequence
<220> FEATURE:
<223> OTHER INFORMATION: primer

<400> SEQUENCE: 89
catgcgtcca cagactgtca tggacggcaa tttcaatg 38

<210> SEQ ID NO 90
<211> LENGTH: 77
<212> TYPE: DNA
<213> ORGANISM: Artificial Sequence
<220> FEATURE:
<223> OTHER INFORMATION: primer

<400> SEQUENCE: 90
catgcgtcca cagactgtca gtactgaagg cgaagttaac gcggaagaag aaggctttat 60
ggacggcaat ttcaatg 77

<210> SEQ ID NO 91
<211> LENGTH: 78
<212> TYPE: DNA
<213> ORGANISM: Artificial Sequence
<220> FEATURE:
<223> OTHER INFORMATION: primer

<400> SEQUENCE: 91

-continued

```
cgctgtcgcg cgttttcggc agtactgaag gcgaagttaa cgcggaagaa gaaggcttta     60

tgaaaatgac cactgaag                                                   78


<210> SEQ ID NO 92
<211> LENGTH: 38
<212> TYPE: DNA
<213> ORGANISM: Artificial Sequence
<220> FEATURE:
<223> OTHER INFORMATION: primer

<400> SEQUENCE: 92

gcccgccctt caaggctatg ccacatagac caaagcac                             38


<210> SEQ ID NO 93
<211> LENGTH: 77
<212> TYPE: DNA
<213> ORGANISM: Artificial Sequence
<220> FEATURE:
<223> OTHER INFORMATION: primer

<400> SEQUENCE: 93

gcccgccctt caaggctagt actgaaggcg aagttaacgc ggaagaagaa ggctttatgc     60

cacatagacc aaagcac                                                    77


<210> SEQ ID NO 94
<211> LENGTH: 79
<212> TYPE: DNA
<213> ORGANISM: Artificial Sequence
<220> FEATURE:
<223> OTHER INFORMATION: primer

<400> SEQUENCE: 94

cttcgcgatg aaattctcag tactgaaggc gaagttaacg cggaagaaga aggctttatg     60

accaaaacac tgacagctc                                                  79
```